US012319920B2

(12) United States Patent
Slade et al.

(10) Patent No.: US 12,319,920 B2
(45) Date of Patent: Jun. 3, 2025

(54) WHEAT WITH INCREASED RESISTANT STARCH LEVELS

(71) Applicant: Arcadia Biosciences, Inc., Dallas, TX (US)

(72) Inventors: Ann J. Slade, Bellevue, WA (US); Dayna L Loeffler, Seattle, WA (US); Aaron M. Holm, Shoreline, WA (US); Jessica C. Mullenberg, Lynnwood, WA (US)

(73) Assignee: ARCADIA BIOSCIENCES, INC., Dallas, TX (US)

( * ) Notice: Subject to any disclaimer, the term of this patent is extended or adjusted under 35 U.S.C. 154(b) by 0 days.

(21) Appl. No.: 18/298,041

(22) Filed: Apr. 10, 2023

(65) Prior Publication Data

US 2023/0287444 A1    Sep. 14, 2023

Related U.S. Application Data

(63) Continuation of application No. 17/147,281, filed on Jan. 12, 2021, now Pat. No. 11,649,464, which is a continuation of application No. 15/914,994, filed on Mar. 7, 2018, now Pat. No. 10,934,557, which is a continuation of application No. 14/825,369, filed on Aug. 13, 2015, now Pat. No. 10,563,217, which is a continuation of application No. 13/633,588, filed on Oct. 2, 2012, now Pat. No. 9,150,839.

(60) Provisional application No. 61/542,953, filed on Oct. 4, 2011.

(51) Int. Cl.
*A01H 6/46* (2018.01)
*C12N 9/10* (2006.01)
*C12N 15/82* (2006.01)

(52) U.S. Cl.
CPC ....... *C12N 15/8245* (2013.01); *A01H 6/4678* (2018.05); *C12N 9/107* (2013.01); *C12Y 204/01018* (2013.01)

(58) Field of Classification Search
None
See application file for complete search history.

(56) References Cited

U.S. PATENT DOCUMENTS

| | | | |
|---|---|---|---|
| 3,690,896 | A | 9/1972 | Maxwell et al. |
| 4,770,710 | A | 9/1988 | Friedman et al. |
| 5,051,271 | A | 9/1991 | Iyengar et al. |
| 5,994,075 | A | 11/1999 | Goodfellow |
| 6,013,861 | A | 1/2000 | Bird et al. |
| 6,303,174 | B1 | 10/2001 | McNaught et al. |
| 6,307,125 | B1 | 10/2001 | Block et al. |
| 6,376,749 | B1 | 4/2002 | Broglie et al. |
| 6,483,009 | B1 | 11/2002 | Poulsen et al. |
| 6,730,825 | B1 | 5/2004 | Goldsbrough et al. |
| 6,734,339 | B2 | 5/2004 | Block et al. |
| 6,897,354 | B1 | 5/2005 | Yamamori et al. |
| 6,903,255 | B2 | 6/2005 | Yamamori et al. |
| 6,916,976 | B1 | 7/2005 | Li et al. |
| 7,001,771 | B1 | 2/2006 | Morell et al. |
| 7,009,092 | B1 | 3/2006 | Jane et al. |
| 7,041,484 | B1 | 5/2006 | Baga et al. |
| 7,521,593 | B2 | 4/2009 | Regina et al. |
| 7,667,114 | B2 | 2/2010 | Morell et al. |
| 7,700,139 | B2 | 4/2010 | Bird et al. |
| 7,700,826 | B2 | 4/2010 | Morell et al. |
| 7,750,206 | B2 | 7/2010 | Li et al. |
| 7,790,955 | B2 | 9/2010 | Li et al. |
| 7,812,221 | B2 | 10/2010 | Regina et al. |
| 7,888,499 | B2 | 2/2011 | Morell et al. |
| 7,919,132 | B2 | 4/2011 | Regina et al. |
| 7,993,686 | B2 * | 8/2011 | Bird ............... A61K 36/899 800/284 |
| 8,115,087 | B2 | 2/2012 | Regina et al. |
| 8,178,759 | B2 | 5/2012 | Morell et al. |
| 8,188,336 | B2 | 5/2012 | Li et al. |
| 8,501,262 | B2 | 8/2013 | Bird et al. |
| 8,829,315 | B2 | 9/2014 | Regina et al. |
| 9,060,533 | B2 | 6/2015 | Regina et al. |
| 9,357,722 | B2 | 6/2016 | Regina et al. |
| 10,934,557 | B2 | 3/2021 | Slade et al. |

(Continued)

FOREIGN PATENT DOCUMENTS

| | | |
|---|---|---|
| CN | 1875105 A | 12/2006 |
| CN | 101663402 A | 3/2010 |

(Continued)

OTHER PUBLICATIONS

Nair et al, 1997, Plant Science, 122:153-163.*
Abel et al., GenBank Accession #Y10416, S. Tuberosum mRNA for Soluble Starch Synthase (Jan. 1997).
Abel et al., "Cloning and functional analysis of a cDNA encoding a novel 139 kDa Starch Synthase from Potato (*Solanum tuberosum* L.)," Plant J. 10(6):981-991 (1996).
Ainsworth et al., "Expression, organization and structure of the genes encoding the waxy protein (granule-bound starch synthase) in wheat," Plant Mol. Biol. 22:67-82 (1993).
Arnold, "Molecular pathogenesis of colorectal cancer", 2005, Cancer, vol. 104, pp. 2035-2047.

(Continued)

*Primary Examiner* — Jason Deveau Rosen
(74) *Attorney, Agent, or Firm* — Troutman Pepper Locke LLP (Rochester)

(57) ABSTRACT

A series of independent human-induced non-transgenic mutations found at one or more of the SBEII genes of wheat; wheat plants having these mutations in one or more of their SBEII genes; and a method of creating and finding similar and/or additional mutations of SBEII by screening pooled and/or individual wheat plants. The seeds and flour from the wheat plants of the present invention exhibit an increase in amylose and resistant starch without having the inclusion of foreign nucleic acids in their genomes. Additionally, the wheat plants of the present invention exhibit altered SBEII activity without having the inclusion of foreign nucleic acids in their genomes.

9 Claims, No Drawings

Specification includes a Sequence Listing.

(56) References Cited

U.S. PATENT DOCUMENTS

| | | |
|---|---|---|
| 2003/0035857 A1 | 2/2003 | Sroka et al. |
| 2004/0023236 A1 | 3/2004 | McCallum et al. |
| 2004/0060083 A1 | 3/2004 | Morell et al. |
| 2004/0199942 A1 | 10/2004 | Morell et al. |
| 2004/0204579 A1 | 10/2004 | Block et al. |
| 2005/0071896 A1 | 3/2005 | Regina et al. |
| 2005/0164178 A1 | 4/2005 | Morell et al. |
| 2006/0010517 A1 | 1/2006 | Li et al. |
| 2006/0035379 A1 | 2/2006 | Morell et al. |
| 2006/0204597 A1 | 9/2006 | Bird et al. |
| 2006/0286186 A1 | 12/2006 | Bird et al. |
| 2007/0104855 A1 | 5/2007 | Arndt et al. |
| 2007/0261136 A1 | 11/2007 | Singletary et al. |
| 2007/0300319 A1 | 12/2007 | Li et al. |
| 2009/0226592 A1 | 9/2009 | Regina et al. |
| 2010/0330253 A1 | 12/2010 | Morell et al. |
| 2011/0010807 A1 | 1/2011 | Morell et al. |
| 2011/0045127 A1 | 2/2011 | Ral et al. |
| 2011/0059225 A1 | 3/2011 | Li et al. |
| 2011/0070352 A1 | 3/2011 | Regina et al. |
| 2011/0212916 A1 | 9/2011 | Bird et al. |
| 2011/0281818 A1 | 11/2011 | Jenkins et al. |
| 2012/0074247 A1 | 3/2012 | Regina et al. |
| 2012/0114770 A1 | 5/2012 | Regina et al. |
| 2012/0129805 A1 | 5/2012 | Li et al. |
| 2012/0266267 A1 | 10/2012 | Li et al. |
| 2013/0115362 A1 | 5/2013 | Regina et al. |
| 2013/0156924 A1 | 6/2013 | Morell et al. |
| 2014/0044826 A1 | 2/2014 | Regina et al. |
| 2017/0367382 A1 | 12/2017 | Regina et al. |

FOREIGN PATENT DOCUMENTS

| | | |
|---|---|---|
| CN | 102150550 A | 8/2011 |
| EP | 2143797 A1 | 1/2010 |
| GB | 2 360 521 | 9/2001 |
| WO | WO 1997/022703 | 6/1997 |
| WO | WO 1999/014314 | 3/1999 |
| WO | WO 1999/0066050 | 12/1999 |
| WO | WO 2000/015810 | 3/2000 |
| WO | WO 2000/066745 | 9/2000 |
| WO | WO 2001/032886 | 5/2001 |
| WO | WO 2001/062934 | 8/2001 |
| WO | WO 2002/037955 | 5/2002 |
| WO | WO 2002/101059 | 12/2002 |
| WO | WO 2003/023024 | 3/2003 |
| WO | WO 2003/094600 | 11/2003 |
| WO | WO 2005/001098 | 6/2004 |
| WO | WO 2005/040381 | 6/2005 |
| WO | WO 2006/069422 | 7/2006 |
| WO | WO 2007124427 A2 | 11/2007 |
| WO | WO 2011/011833 | 2/2011 |
| WO | WO 2012058730 | 5/2012 |
| WO | WO 2012/103594 | 8/2012 |
| WO | WO 2013/052499 | 4/2013 |

OTHER PUBLICATIONS

Baba et al., "Identification, cDNA cloning and gene expression of soluble starch synthase in rice (Oryza stativa L.) Immature Seeds," Plant Physiol. 103:565-573 (1993).
Ball et al., "From glycogen to amylopectin: A model for the biogenesis of theplant starch granule," Cell 86:349-352, 1996.
Banks et al., "Studies on Starches of High Amylose Content," Starch 26:289-300 (1974).
Batey et al., "Measurement of Amylose/Amylopectin Ratio by High-Performance Liquid Chromatography," Starch 48:338-344 (1996).
Bernardo et al., North American study on essential derivation in maize: inbreds developed without and with selection from F2 populations, Theor Appl Genet (2001) 102:986-992, 7 pages.
Bhullar et al., GenBank Accession #CAB40374, Starch synthase isoform SS III (Vigna unguiculata) (Apr. 1999).

Blauth et al., "Identification of Mutator Insertional Mutants of Starch-Branching Enzyme 2a in Corn," Plant Physiology 125:1396-1405 (2001).
Block et al., GenBank Accession #U48227, Triticum aestivm soluble starch synthase mRNA, partial cds. (Jun. 1996).
Boyer et., "Evidence for Independent Genetic Control of the Multiple Forms of Maize Endosperm Branching Enzymes and Starch Synthases," Plant Physiology 67:1141-1145 (1981).
Buleon et al., "Starch Granules: Structure and Biosynthesis," International Journal of Biological Macromolecules 23:85-112 (1998).
Butardo et al., "Impact of down-regulation of starch branching enzyme IIb in rice by artificial microRNA- and hairpin RNA-mediated RNA silencing," J. Exp. Bot. 62:4927-4941, 2011.
Chen et al., "A rapid DNA minipreparation method suitable for AFLP and other PCR applications," Plant Molecular Biology Reporter 17:53-57, 1999.
Chinese Office Action and English translation for application No. 201280059762.8 dated Jun. 24, 2015, 10 pages.
Clarke et al., "Gene expression in a starch synthase IIa mutant of barley: changes in the level of gene transcription and grain composition." Functional Integrated Genomics, 2008, 8:211-221.
Colasuonno et al., "TILLING starch branching enzyme-IIa and IIb to produce high amylose wheat," Abstract P292 from the Plant & Animal Genomes XVII Conference, San Diego, CA, Jan. 10-14, 2009.
Colbert et al., "High-throughput screening for induced point mutations," Plant Physiology 126:480-484, 2001.
Craig et al., "Mutations in the Gene Encoding Starch Synthase II Profoundly Alter Amylopectin Structure in Pea Embroyos," The Plant Cell 10:413-426 (1998).
Denyer et al., "Identification of Multiple Isoforms of Soluble and Granule Bound Starch Synthase in Developing Wheat Endosperm." Planta 196:256-265 (1995).
D'Hulst et al., GenBank Accession #AAC17969, Granule-bound starch synthase I precursor [Chlamydomonas reinhardtii] (Nov. 2001).
Dry et al., "Characterization of cDNAs encoding two isoforms of granule-bound synthase which show differential expression in developing storage organs of pea and potato," Plant J. 2(2):193-202 (1992).
Edwards et al., "Biochemical and Molecular Characterization of a Novel Starch Synthase from Potato Tubers," Plant J. 8(2):283-294 (1995).
English language abstract of PCT International Patent Application Publication No. WO 2003/023024, published Mar. 20, 2003 (Japan Science and Technology Corporation).
European Office Action for application No. 12775107.1 dated Jun. 1, 2015,4 pages.
Feiz et al., "In planta mutagenesis determines the functional regions of the wheat puroindoline proteins," Genetic 183:853-860,2009.
Fujita et al., (2007) "Characterization of SSIIIa-Deficient Mutants of Rice: The Function of SSIIIa and Pleiotropic Effects by SSIIIa Deficiency in the Rice Endosperm" Plant Physiology , 144: 2009-2023.
Flipse et al., "Introduction of Sense and Antisense cDNA for Branching Enzyme inthe Amylose-Free Potato Mutant Leads to Physico-Chemical Changes in the Starch," Planta 198:340-347 (1996).
Fujita et al., "Antisense Inhibition of Isoamylase Alters the Structure of Amylopectin and the Physiochemical Properties of Starch in Rice Endosperm," Plant Cell Physiol. 44(6):607-618 (2003).
Fujita et al., "Grain and Starch Characteristics of the Double Recessive Lines for Amylose-free and High Amylose Gene in Barley," Breeding Science 49:217-219 (1999).
Gao et al., "Isolation, Characterization, and Expression Analysis of Starch Synthase IIa cDNA from wheat (Triticum aestivum L.)," Genome 43:768-775 (2000).
Gao et al., "Characterization of dull I, a Maize Gene Coding for a Novel Starch Synthase," Plant Cell 10:399-412 (1998).
Gao et al., Triticum aestivum mRNA for Starch Synthase IIa-2 (wSs2a-2), EMBL Abstract Accession No. AJ269503 (Jul. 6, 2000).
Gao et al., GenBank Accession #AAC14014, Starch synthase DULL 1 [Zea mays] (Apr. 1998).

(56) References Cited

OTHER PUBLICATIONS

Gao et al., GenBank Accession #AAC14015, Starch synthase DULL 1 [*Zea mays*] (Apr. 1998).
Gao et al., GenBank Accession #AJ26502, Triticum aestivum mRNA for starch synthase Iia-1 (wSs2a-1 gene) (Apr. 2002).
Gao et al., GenBank Accession #CAB86618, Starch synthase Iia-1 [Triticum aestivum] (Apr. 2002).
Gillespie, "Type 1 diabetes: pathogenesis and prevention", CMAJ, 2006, vol. 175, pp. 165-170.
Goering, et al., "A Comparison of the Properties of Large- and Small-Granule Starch Isolated from Several Isogenic Lines of Barley," Cereal Chemistry 51:573-578 (1974).
Harn et al., "Isolation and Characterization of the zSSIIA and zSSIIb Starch Synthase cDNA Clones from Maize Endosperm," Plant Mol. Biol. 37:639-649 (1998).
Henikoff et al., "Using substitution probabilities to improve position specific scoring matrices," Computer Applications in the Biosciences 12: 135-143, 1996.
Henikoff et al., "Amino acid substitution matrices from protein blocks," Proc. Natl. Acad. Sci. USA 89:10915-10919,1992.
Holmes et al., Henderson's Dictionary of Biological Terms, 9th Ed., Van Nostrand Reinhold Co., New York, 1979, p. 218.
Innis et al., "PCR protocols: A guide to methods and applications," Academic Press, San Diego, 1990.
International Search Report, issued Jan. 17, 2012 in connection with PCT International Application No. PCT/AU2011/01426.
International Search Report, issued May 14, 2012 in connection with PCT International Patent Application No. PCT/AU2012/000098.
Jansson et al., "Cloning, Characterization and Modification of Genes Encoding Starch Branching Enzymes In Barley," Starch: Structure and Functionality, Royal Society of Chemistry, London, pp. 196-203 (1997).
Jarvi et al., "Shrunken Endosperm Mutants in Barley," Crop Science 15:363-366 (1975).
Kim et al., "*Oryza minuta* genomic clone OM Ba0201cll 5", Database Embase Elsevier Science Publishers, Amsterdam, NL, Jul. 8, 2005.
Klosgen et al., "Molecular Analysis of the Waxy Locus of *Zea mays*," Mol. Gen.Genet. 203:237-244 (1986).
Knight et al., "Molecular Cloning of Starch Synthase I from Maize (w64) Endosperm and Expression in *Escherichia coli*," Plant J. 14(5):613-622 (1998).
Konovalov et al., An approach to DNA polymorphism screening in SBEIIa homeologous genes of polyploid wheat (*Triticum* L.) Euphytica 183(2), 173-184, 2011 (Abstract Only).
Konovalov et al., "The sequence polymorphism of SBEIIa gene in wheat (*Triticum* sp.) In: Appeals R, Eastwood R, LagudahE, Landridge P, Mackay M, McIntyre L, Sharp P (eds) Proc." IIthInt. Wheat Genet. Symp. pp. 418-420, 2008.
Kull et al., "Genetic Engineering of Potato Starch Composition: Inhibition of Amylose Biosynthesis in Tubers from Transgentic Potato Lines by the Expression of Antisense Sequences of the Gene for Granule-bound Starch Synthase," J. Genet. Breed. 49:69-76 (1995).
Li et al., "Integrated platform for detection of DNA sequence variants using capillary array electrophoresis," Electrophoresis 23(10): 1499-1511, 2002.
Li et al. (2011) "The barley amol locus is tightly linked to the starch synthase IIIa gene and negatively regulates expression of granule-bound starch synthetic genes" Journal of Experimental Botany 62: 5217-5231.
Li et al., "Cloning and Characterization of a Gene Encoding Wheat Starch Synthase I," Theor. AEEI. Genet. 98:1208-1216 (1999).
Li et al., "The Localization and Expression of the Class II Starch Synthases of Wheat," Plant Physiology 120:1147-1155 (1999).
Li et al., (2003) "The structural organisation of the gene endoding class II starch synthase of wheat and barley and the evolution of the genes encoding starch synthases in plants" Funct Integr Genomics 3:76-85.

Li et al., Triticum aestivum Starch Synthase IIA mRNA, complete cds., EMBL Abstract Accession No. AF155217 (Sep. 7, 1999).
Liu et al., "Stable Inheritance of the Antisense Waxy Gene in Transgenic Rice with Reduced Amylose Level and Improved Quality," Transgenic Research, 12:71-82, (2003).
Lorberth et al., "Inhibition of a starch-granule-bound protein leads to modified starch and repression of cold sweetening." Nature Biotechnology, (1998); 16(1):473-477.
Martin et al., "Starch biosynthesis, " The Plant Cell 7:971-985, 1995.
Mazzolini et al., "Assaying synthetic ribozymes in plants: high-level expression of a functional hammerhead structure fails to inhibit target gene activity in transiently transformed protoplasts," Plant Mol. Biol. 20:715-731 (1992).
Mccallum et al., "Target screening for induced mutations," Nature Biotechnology 18:455-457, 2000a.
Mccallum et al., "Targeting induced local lesions in genomes (TILLING) for plant functional genomics," Plant Physiology 123:439-442, 2000b.
Miao, Hongmei et al., "Evaluation and Characterization of an Endosperm-Specific sbella Promoter in Wheat II," Chinese Science Bulletin, vol. 49, No. 6, pp. 579-585 (2004).
Mizuno et al., "Alteration of the Structural Properties of Starch Components by the Lack of an Isoform of Starch Branching Enzyme in Rice Seeds," J. Biol. Chem. 268 (25):19084-19091 (1993).
Morell et al., "Barley sex6 Mutants Lack Starch Synthase iia Activity and Contain a Starch with Novel Properties," The Plant Journal 34:173-185 (2003).
Morell et al., "The Biochemistry and Molecular Biology of Starch Synthesis in Cereals," Aust. J. Plant. Physiol. 22:647-660 (1995).
Myers et al., "Recent Progress toward Understanding Biosynthesis of the Amylopection Crystal," Plant Physiology 122:989-997 (2000).
Nakamura Y., "Towards a Better Understanding of the Metabolic System for Amylopectin Biosynthesis in Plants: Rice Endoserm as s Model Tissue," Plant Cell Physiology 43(7):718-725 (2002).
Needleman, A general method applicable to the search for similarities in the amino acid sequences of two proteins. J. Mol. Biol. 48:443-453, 1970.
Newman et al. (1978) "Comparative Nutritive Value of Glacier and High Amyliose Glacier Barleys" Journal of Animal Science, 47:448-456.
Ng et al., "SIFT: Predicting amino acid changes that affect protein function," Nucleic Acids Research 31 (13):3812-3814, 2003.
Nishi et al., "Biochemical and Genetic Analysis of the Effects of Amylose-Extender Mutation in Rice Endosperm," Plant Physiology 127:459-472 (2001).
Okagaki R. J., "Nucleotide Sequence of a Long cDNA from the Rice Waxy Gene," Plant Molecular Biology 19:513-516 (1992).
Puchta, "Gene Replacement by Homologous Recombination in Plants," Plant Mol. Biol. 48:173-182 (2002).
Rahman et al., "Comparison of starch-branching enzyme genes reveals evolutionary relationships among isoforms. Characterization of a gene for starch branching enzyme IIa from the wheat D genome donor Aegilops tauschii," Plant Physiology 125(3), 1314-1324,2001.
Rahman et al., GenBank Accession #AF076680, Aegilops tauschii starch branching enzyme-I (SBE-1) gene, complete cds. (May 1999).
Rahman, S. et al., "Characterisation of a Gene Encoding Wheat Endosperm Starch Branching Enzyme-I," Theor. Appl. Genet. 98:156-163 (1999).
Rahman, S. et al., "The Major Proteins of Wheat Endosperm Starch Granules," Aust. J. Plant Physiol. 22:793-803 (1995).
Rahman, S. et al., A Complex Arrangement of Genes at a Starch Branching Enzyme I Locus in the D-genome Donor of wheat, Genome 40:465-474 (1997).
Regina et al., "Control of starch branching in barley defined through differential RNAi suppression of starch branching enzyme IIa and IIb," J. Exp. Bot. 61: 1469-1482 2010.
Regina et al., Starch branching enzyme IIb in wheat is expressed at low levels in the endosperm compared to other cereals and encoded at a non-syntenic locus, Planta 2005222:899-909, 11 pages.

(56) References Cited

OTHER PUBLICATIONS

Regina, (2006) "High-amylose wheat generated by RNA interference improves indices of large-bowel health in rats," PNAS, vol. 103, pp. 3546-3551.
Safford et al., "Consequences of Antisense RNA Inhibition of Starch Branching Enzyme Activity on Properties of Potato Starch," Carbohydrate Polymers 35:155-168 (1998).
Saika et al., Application of gene targeting to desigued mutation breeding of high-tryptophan rice. Plant Physiology 156:1269-1277, 2011.
Sathish et al., "Cloning and Anti-Sense RNA Constructs of a Starch Branching Enzyme Gene From Barley Endosperm," Photosynthesis: from Light to Biosphere vol. V. P. Mathis (ed.) pp. 313-316 (1995).
Schondelmaier et al., "Genetical Studies in the Mode of Inheritance and Localization of the amol (High Amylose) Gene in Barley," Plant Breeding 109:274-280 (1992).
Schwall, et al., "Production of Very-High-Amylose Potato Starch by Inhibition of SBE A and B," Nature Biotechnology 18:551-554 (2000).
Sestili et al., "Increasing the amylose content of durum wheat through silencing of the SBElla genes," BMC Plant Biology 2010 10: 144, 12 pages.
Shannon et al., "In Starch: Chemistry and Technology," Whistler et al., eds, Academic Press, Orlando, FL 25-86 (1984).
Siddiqui et al. (2008) "Germination Behavior of Wheat (*Triticum aestivum*) Varieties to Artificial Ageing Under Varying Temperature and Humidity" 40 (3) : 1121-1127.
Sidebottom et al., "Characterization of the Difference of Starch Branching Enzyme Activities in Normal and Low-Amylopectin Maize during Kernel Development," Journal of Cereal Science 27:279-287 (1998).
Slade et al., "Development of high amylose wheat through TILLING," BMC Plant Biology 201212:69, 17 pages.
Slade et al., A reverse genetic, nontransgenic approach to wheat crop improvement by TILLING, Nature Biotechnology, Jan. 2005, vol. 23 No. 1, 7 pages.
Stewart et al., "A rapid CTAB DNA isolation technique useful for rapid fingerprinting and other PCR applications," Bio Techniques 14(5):748-749, 1993.
Sun et al., "Identification of Four Starch-Branching Enzymes in Barley Endosperm: Partial Purification of Forms I, IIa and IIb," New Phytol. 137:215-222 (1997).
Sun et al., "The Two Genes Encoding Starch-Branching Enzymes IIa and IIb Are Differentially Expressed in Barley," Plant Physiology 118:37-49 (1998).
Sundberg et al., "Glycaemic Responses and Hypocholesterolaemic Effects of High-Amylose Barley Diets on Broiler Chicks," J. Sci. Food Agric. 76:457-463 (1998).
Takaoka, M. et al., "Structural characterization of high molecular weight starch granule-bound proteins in wheat (*Triticum aestivum* L.)," J. Agric. Food Chem. 45:2929-2934 (1997).
Taylor et al., PARSENSP: "A tool for the analysis of nucleotide polymorphisms," Nucleic Acids Research 31:3808-3811, 2003.
Terada at al., (2002) "Efficient Gene Targeting by Homologous Recombination in Rice," Nature Biotech. 20:1030-1034.
Tetlow IJ et al., (2004) "Recent developments in understanding the regulation of starch metabolism in higher plants," Journal of Experimental Botany 55(406):2131-2145.
Thomas, et al., "Size Constraints for Targeting Post-Transcriptional Gene Silencing and for RNA-directed Methylation in Nicotiana benthamiana Using a Potato Virus X Vector," Plant J. 25:417-425 (2001).
Topping et al., "Resistant Starch and Health—Himalaya 292, a Novel Barley Cultivar to Deliver Benefits to Consumers" Starch/Starke 55: 539-545, 2003.
Topping et al., (2001) "Short-Chain Fatty Acids and Human Colonic Function: Roles of Resistant Starch and Non-starch Polysaccharides" Physiological Review, vol. 81(3), pp. 1031-1064.
Uauy et al., "A modified TILLING approach to detect induced mutations in tetraploid and hexaploid wheat," BMC Plant Biology 9: 115,2009.
USDA, ARS, National Genetic Resources Program. Germplasm Resources Information Network (GRIN) [Online Database] National Germplasm Resources Laboratory, Beltsville, Maryland (http://www.ars-grin.gov/npgs/), GRIN System [Accession No. GSHO 2476, Jun. 23, 1997].
Van der Leij et al., "Sequence of the Structural Gene for Granule-Bound Starch Synthase of Potato (*Solanum Tuberosum* L.) and Evidence for a Single Point Deletion in the amf allele," Mol. Gen. Genet. 228:240-248 (1991).
Vrinten and Nakamura, "Wheat Granule-Bound Starch Synthase I and II Are Encoded by Separate Genes That Are Expressed in Different Tissues," Plant Physiology 122:255-263 (2000).
Walker and Merritt, "Genetic Control of Abnormal Starch Granules and High Amylose Content in a Mutant of Glacier Barley," Nature 221:482-484 (1969).
Walter et al., GenBank Accession #AAB17085, Starch Synthase (Oct. 1996).
Walter et al., GenBank Accession #U66377, Triticum aestivum soluble starch synthaese mRNA, partial cds. (Oct. 1996).
Wang et al., "Variance and marker estimates of parental contribution to F2 and BCl-derived inbreds," Crop Sci. 40:659-665, 2000.
Wang et al., (2009) "Simultaneous selectioin of major and minor genes: use of QLT to increase selection efficiency of coleoptile length of wheat (*Triticum aestivum* L.)," Theor Appl Genet, 119:65-74.
Wasserman et al., "Microstructure, Thermal properties and susceptibility of the high amylose wheat starch to enzymatic hydrolysis: A new material for resistant starch (SRIII) production," Polish Jounal of Food and Nutrition Sciences vol. 13-54, No. 2, pp. 151-156 (2004).
Wei et al., "C-Type Starch from High-Amylose Rice Resistant Starch Granules Modified by Antisense RNA Inhibition of Starch Branching Enzyme," Journal of Agricultural and Food Chemistry, 58:7383-7388 (2010).
Wesley SV et al., (2001) "Construct design for efficient, effective and high-throughput gene silencing in plants." Plant J. 27(6):581-90.
Wolters AM, Visser RG., (2000) "Gene silencing in potato: allelic differences and effect of ploidy" Plant Mol Biol. 43(2-3):377-86.
Yamamori and Endo, "Variation of Starch Granule Proteins and Chromosome Mapping of Their Coding Genes in Common Wheat," Theor. Appl. Genet. 93:275-181 (1996).
Yamamori et al., "Genetic Elimination of a Starch Granule Protein, SGP-1, of Wheat Generates an Altered Starch with Apparent High Amylose," Theor. AJ2, el. Genet. 101:21-29 (2000).
Yamamori, "Selection of a Wheat Lacking a Putative Enzyme for Starch Synthesis, SGP-1," Proc. 9th In Wheat Gen. Symp. 4:300-302 (1998).
Zhang et al., "High frequency targeted mutagenesis in *Arabidopsis* using zinc finger nucleases," Proc. Natl. Acad. Sci. USA 107(26): 12028-12033, 2010.
Zhang et al. (2008) "Overlapping functions of the starch synthases SSII and SSIII in amylopectin biosynthesis in *Arabidopsis*" BMC Plant Biology 8:96.
Zobel et al., Starch Gelatinization: An X-ray Diffraction Study. Cereal Chem, 1988, 65 (6):443-446.
Zobel, H.F., Starch Crystal Transformations and Their Industrial Importance. Starch, 1988, 40(1):1-7.
Zwar and Chandler, α-Amylose production and leave protein synthesis in a gibberellin-responsive dwarf mutant of 'Himalya' barley (*Hordeum vulgare* L.). Planta, 1995, 197:39-48.
Botticella et al., "High Resolution Melting Analysis for the Detection of EMS Induced Mutations in Wheat Sbella Genes," Plant Biology, vol. 11, 14 pp. (2011).
Hazard et al., "Induced Mutations in the Starch Branching Enzyme II (SBEII) Genes Increased Amylose and Resistant Starch Content in Durum Wheat," Crop Sci. 52(4):1754-66 (2012).
Office Action for U.S. Appl. No. 13/668,177 (Dec. 18, 2014).
Office Action for U.S. Appl. No. 13/668,177 (Jul. 21, 2015).

(56) References Cited

OTHER PUBLICATIONS

Declaration Under 37 C.F.R. § 1.132 of Ahmed Regina for U.S. Appl. No. 13/668,177, dated Dec. 5, 2014.
Examination Report No. 1 for Australian Patent Application No. 2012318814, Dated May 7, 2017.
Office Action for European Patent Application No. 12 775 107.1, Dated Apr. 20, 2016.
Office Summons to Attend Oral Proceedings for European Patent Application No. 12775107.1, Dated Oct. 4, 2017.
Stryer, "Biochemistry", 3rd ED., New York, W.H. Freeman and Company, pp. 106-107(1988).
Williams et al., "Genome-wide Prediction of Stop Codon Readthrough During Translation in the Yeast *Sacchararomyces cerevisiae*", Nucleic Acids Research, 32 (22). 6605-6616, (2004).
Ishikawa et al., "PCR-Based Landmark Unique Gene (PLUG) Markers Effectively Assign Homoeologous Wheat Genes to A, B, and D Genomes", BMC Genomics, (2007).
International Preliminary Report on Patentability and Written Opinion for Corresponding International Patent Application No. PCT/US2012/058481, Dated Apr. 8, 2014.
English Translation of Pertinent Portion of the First Office Action for China Patent Application No. 201280059762.8, Dated May 27, 2015.
English Translation of Pertinent Portion of the Second Office Action for China Patent Application No. 201280059762.8, Dated Apr. 7, 2016.
English Translation of Pertinent Portion of the Decision of Rejection for China Patent Application No. 201280059762.8, Dated Dec. 27, 2016.
English Translation of Pertinent Portion of the Notification of Reexamination for China Patent Application No. 201280059762.8, Dated Sep. 29, 2017.
International Search Report for PCT App. No. PCT/US2012/058481 mailed on Feb. 15, 2013.
NCBI GenBank Accession FM865435, Aug. 22, 2012.
NCBI GenBank Accession CAR95900, Aug. 27, 2012.
NCBI GenBank Accession AF338431, Mar. 27, 2001.
NCBI GenBank Accession AAK26821, Mar. 27, 2001.
NCBI GenBank Accession AY7 40398, Mar. 14, 2006.
NCBI GenBank Accession AAW80632, Mar. 14, 2006.
Fujisawa et al., "Suppression of the Heterotrimeric G Protein Causes Abnormal Morphology, Including Dwarfism, in Rice," Proc. Natl. Acad. Sci. USA 96:7575-7580 (1999).
Laby et al., "The *Arabidopsis* Sugar-Insensitive Mutants sis4 and sis5 are Defective in Abscisic Acid Synthesis and Response," The Plant Journal 23(5):587-596 (2000).
Salmeron et al., "Tomato Mutants Altered in Bacterial Disease Resistance Provide Evidence for a New Locus Controlling Pathogen Recognition," The Plant Cell 6:511-520 (1994).
Wu et al., "Chemical- and Irradiation-Induced Mutants of Indica Rice IR64 for Forward and Reverse Genetics," Plant Molecular Biology 59:85-97 (2005).
Declaration of Ann J. Slade, Ph.D., dated Oct. 18, 2018.
Hicks et al., "Early Flowering3 Encodes a Novel Protein that Regulates Circadian Clock Function and Flowering in *Arabidopsis*," Plant Cell 13:1281-92 (2001).
Oki et al., "Study of Novel dl Alleles, Defective Mutants of the Alpha Subunit of Heterotrimeric G-protein in Rice," Genes Genet. Syst. 84:35-42 (2009).
Fitzgerald et al., "A High-Throughput Method for the Detection of Homoeologous Gene Deletions in Hexaploid Wheat," BMC Plant Biology 10:264 (2010).
Sega, "A Review of the Genetic Effects of Ethyl Methanesulfonate," Mutation Res. 134:113-42 (1984).
Leung et al., "Deletion Mutants for Functional Genomics: Progress in Phenotyping, Sequence Assignment, and Database Development," In Rice Genetics IV, 239-51, (2001).
Comai et al., "Efficient Discovery of DNA Polymorphisms in Natural Populations by Ecotilling," Plant J. 37:778-86, (2004).

Extended European Search Report for 19151512.1 (mailed Jun. 13, 2019).
Declaration of Interference under 37 C.F.R. § 41.203(d), Patent Interference 106,110 between U.S. Pat. No. 10,246,716 to Slade et al. and U.S. Appl. No. 15/440,652 to Regina et al. (dated Apr. 24, 2019).
Corrected Brief For Appellants *Slade* et al. v. *Regina* et al. U.S. Interference No. 106,094, Dated Dec. 17, 2018.
Examination Report for India Application No. 706/KOLNP/2014 (Oct. 23, 2018) (with attached partial translation).
Examination Report for Canada Application No. 2,850,490 (Jul. 12, 2018).
Office Action for U.S. Appl. No. 14/825,369 (Aug. 27, 2018).
Interview Summary for U.S. Appl. No. 15/975,410 (Sep. 13, 2018).
Interview Summary for U.S. Appl. No. 15/649,231 (Sep. 13, 2018).
Decision Motions, Patent Interference 106,094 *Regina* v. *Slade*, Dated Aug. 14, 2018.
Office Action for U.S. Appl. No. 15/649,231 (Jul. 11, 2018).
Office Action for U.S. Appl. No. 15/975,410 (Jul. 18, 2018).
Wiersma et al., "Recurrent Selection for Kernel Weight in Spring Wheat," Crop Science 41:999-1005 (2001).
Regina Reply 1 Written Description, Patent Interference 106,094 *Regina* v. *Slade*, Dated Jul. 17, 2018.
Regina Motion 2 Benefit, Patent Interference 106,094 *Regina* v. *Slade*, Dated Jul. 17, 2018.
Office Action for European Patent Application No. 12 775 107.1, Dated Nov. 30, 2017.
Examination Report No. 2 for Australian Patent Application No. 2012318814, Dated Feb. 26, 2018.
English Translation of Pertinent Portion of the Decision of Reexamination for China Patent Application No. 201280059762.8, Dated Mar. 9, 2018.
Regina List of Proposed Motions, Patent Interference 106,094 *Regina* v. *Slade*, Dated Apr. 4, 2018.
Office Action for U.S. Appl. No. 15/615,555, Dated Feb. 2, 2018.
Regina Motion 1 Written Description 112 1st, Patent Interference 106,094 *Regina* v. *Slade*, Dated May 2, 2018.
Examination Report for Australian Patent Application No. 12018211346, Dated Dec. 6, 2019.
Office Action for U.S. Appl. No. 15/914,994 (mailed Nov. 21, 2019).
Office Action for Argentina Patent Application No. 20120103690, Dated Oct. 1, 2019.
Examination Report for Canada Application No., 2,850,490 (Sep. 18, 2019).
Mikulikova and Kraic, "Natural Sources of Health-Promoting Starch", J. Food Nutrition Res. 45:69-76 (2006).
Brazilian Office Action and English translation for application No. 11-2014-007928-5 dated Jun. 11, 20, 9 pages.
Examination Report for Canada Application No., 2,850,490 dated Dec. 7, 2020.
Monteiro de Souza and de Oliveira e Magalhaes, "Application of Microbial Alpha-Amylase in Industry—A Review", Brazilian J. of Microbiology, 41:850-861 (2010).
Final Office Action for U.S. Appl. No. 14/825,369, Dated Aug. 31, 2017.
Office Action for U.S. Appl. No. 14/825,369, Dated Dec. 28, 2016.
Office Action for U.S. Appl. No. 14/825,369 Dated Nov. 27, 2017.
Office Action for U.S. Appl. No. 14/825,369 (mailed Feb. 26, 2019).
Office Action for U.S. Appl. No. 15/914,994 (mailed Feb. 5, 2019).
Second Office Action for China Patent Application No. 201810613951.4 and Translation (Apr. 29, 2022).
Third Office Action for China Patent Application No. 201810613951.4 and Translation (Oct. 9, 2022).
Examination Report for Canadian Application No. 2850490 (Jan. 17, 2022).
Kaur et al., "Starch—A Potential Biomaterial for Biomedical Applications," Nanomaterials and Nanosystems for Biomedical Applications, pp. 83-98 (2007).
Cable, "Starch", Starch pp. 685-691, Feb. 20, 2009.
Third Office Action for Uruguayan Patent Application No. 34364 and Partial Translation (Oct. 13, 2021).

(56) References Cited

OTHER PUBLICATIONS

Office Action for China Patent Application No. 201810613951.4 and Translation (Sep. 14, 2021).
Examination Report for European Application No. 19151512.1 (Jun. 24, 2021).
First Written Opinion for Brazilian Patent Application No. BR122020015607-4 and Translation (Mar. 22, 2021).
Second Office Action for Uruguayan Patent Application No. 34364 and Translation (Jun. 23, 2021).
Office Action for Paraguayan Patent Application No. 46605-252/12 and Translation (Jul. 3, 2021).
Notice of Hearing for Indian Patent Application No. 706/KOLNP/2014 (Mar. 5, 2021).
Office Action for Uruguayan Patent Application No. 34364 and Partial Translation (Feb. 19, 2021).
Informal English Translation of the Written Opinion for Brazilian Patent Application No. BR112014007928-5 (Feb. 17, 2021).
Office Action for Paraguayan Patent Application No. 46605-252 12 and Partial Translation (Feb. 4, 2021).

* cited by examiner

```
                              SEQUENCE LISTING

Sequence total quantity: 58
SEQ ID NO: 1            moltype = DNA  length = 6114
FEATURE                 Location/Qualifiers
source                  1..6114
                        mol_type = unassigned DNA
                        organism = Triticum aestivum
SEQUENCE: 1
caattaatat cgtccatcac tcgggttccg cgctgcattt cggccggcgg gttgagtgag   60
atctgggcca ctgaccgact cactcgctcg ctgcgcgggg atggcgacgt ttgcggtgtc  120
cggcgcgacc ctcggtgtgg cgcggcccgc cggcgccggc ggcggactgc tgccgcgatc  180
cggctcggag cggaggggcg gggtggacct gccgtcgctg ctcctcagga agaaggactc  240
ctctcgtacg cctcgctcgc tcgctccaat ctcccgtcca tttttgcccc ccttctctct  300
ccctatctgc gcgcgcatgg cctgttcgat gctgttcccc agttgatctc catcaacgag  360
agagatagct ggattaggcg atcgcctgcg tcagtgtcac ccaggccctg gtgttatcac  420
ggctttgatc atctcctccc attctgatat tttctcactc tttcttctgt tcttgctgta  480
actgcaagtt gtagcattgt ctcactattg tagtcatcct tgcattgcag gcgccgtcct  540
gagccgcgcg gcctctccag ggaaggtcct ggtgcctgac ggtgagagcg acgacttggc  600
aagtccggcg caacctgaag aattacaggt acacaccatc gtgccgggaa atcttcatac  660
aatcgttatt cacttaccaa atgccggatg aaaccaagcc gcggaggcgt caggttttga  720
gcttcttcta tcagcattgt gcagtactgc actgccttgt gcattttgtt agccgtggcc  780
ccgtgctggc tcttgggcca ctgaaaactc agatggatgt gcattctagc aagaacttca  840
cgaaataatg cactgtttgt ggtttcgtta gtctgctcta caattgctat tttcgtgctg  900
tagataccta aagacatcga ggagcaaacg gctgaagtaa acatgacagg ggggactgca  960
gaaaaacttg aatcttcaga accgactcaa ggcattgtgg aaacaatcac tgatggtgta 1020
accaagggag ttaaggaact agtcgtgggg gagaaaccgc gagttgtccc aaaaccagga 1080
gatgggcaga aaatatacga gattgaccca acgctgaaag attttcggag ccatcttgac 1140
taccggtaat gcctacccgc tactttcgct cattttgaat taaggtcctt tcgtcatgca 1200
aatttgggga acatcaaaga gacaaagact agggaccact atttcttaca gttcccctca 1260
tggtctgaga atatgctggg acgtagatgt ataattgatg gctacaattt gctcataatt 1320
acgatacaaa taactgtctc tgatcattgc aattacagag tggcaaactg attaaaatgt 1380
gatagatggg ttatagattt tactttgcta attcctctac caaattcctg gggaaaaaaa 1440
tctaccagtt gggcaactta gtttcttatc tttgttgcct ctttgttttg gggaaaacac 1500
actgctaaat ttgaatgatt ttgggtatgc ctccgtggat tcaacagata cagcgaatac 1560
aggagaattc gtgctgctat tgaccaacat gaaggtggat tggaagcatt ttctcgtggt 1620
tatgaaaagc ttggatttac ccgcaggtaa atttaaagct tcagtattat gaagcgcctc 1680
cactagtcta cttgcatatc ttacaagaaa atttataatt cctgttttcg cctctctttt 1740
ttccagtgct gaaggtattg tctagttgca tatcttataa gaaaatttat gttcctgttt 1800
tcccctattt tccagtgctg aaggtatcac ttaccgagaa tgggctcctg gagcgcatgt 1860
acgtcttta  agtcttaaca gacaccttcc aattcattgt taatggtcac actattcacc 1920
aactagctta ctggacttac aacttagctt actgaatact gaccagttgc tctaaattta 1980
tgatctggct tttgcatcct attacagtct gcagcattag taggtgactt caacaattgg 2040
aatccgaatg cagatactat gaccagagta tgtctacagc ttggcaatct tccacctttg 2100
cttcataact actgatacat ctatttgtat ttattttgct gtttgcacat tccttaaagt 2160
tgagcctcaa ctatatcata tcaaaatggt ataatttgtc agtgtcttaa gcttcagcct 2220
aaagattcta ctcaaattgg tccatctttt tgagattgaa aatgagtata ttaaggatgg 2280
atgaataggt gcaacactcc cattctttgg tagaaccttc tgcattatgt gtgttttttc 2340
atctcaatg  agcatatttc catgctatca gtgaaggttt gctcctattg atgccgatat 2400
ttgatatgat cttttcagga tgattatggt gtttggaga  ttttcctccc taacaatgct 2460
gatggatccc cagctattcc tcatggctca cgtgtaaagg taagctggcc aattatttag 2520
ttgaggatgt agcattttcg aactctgccc actaagggtc cctttgcctt tctgtttttct 2580
agatacggat ggatactcca tctggtgtga aggattcaat ttctgcttgg atcaagttct 2640
ctgtgcaggc tccaggtgaa ataccattca atggcatata ttatgatcca cctgaagagg 2700
```

```
taagtatcga tctccattac attattaaat gaaatttcca gtgttacggt tttttaatac 2760
ccatttcgtg tctcactgac atgtgagtca agacaatact ttagaatttg gaagtgacat 2820
atgcattaat tcaccttcta agggctaagg ggcaagcaac catggtgatg tttgtatgct 2880
tgtgtgtgac ttaagatctt atagctcttt tatgtgttct ctgttggtta ggatattcca 2940
ttttgacctt ttgtgaccat ttactaagga tatttacatg caaatgcagg agaagtagt  3000
cttccaacat cctcaaccta aacgaccaga gtcactgagg atttatgaat cacacattgg 3060
aatgagcagc ccagtatgtc aataagttat ttcacctgtt tctggtctga tggtctattc 3120
tatgggattt tagttctgt tatgtattgt taacatataa catggtgcat tcacgtgaca 3180
acctcgattt tattttctaa tgttattgca atagctcggt ataatgtaac catgttacta 3240
gcttaagatg gttagggttt cccacttagg atgcatgaaa tatcgcattg gagcatctcc 3300
agcaagccat ttttttgacg gttaacagca ggagctctgc ttttcattat aggagaggga 3360
aatgctgtac agactgaagt cagtcagagc aaagtaactt agaatcattt atgggccacc 3420
ctgcacaggg cagaaggcag gcaggaacga tcctctacag ccgtcggatt gcctccatca 3480
gaggaatcct ggccgttaat catgctctgg cccagtgtc agaatgcatc aaccagactg 3540
aggtgcttgc ctccttattg gtaaaggatg cagcggtacg agcctattga acagatcctg 3600
ttcaagtaag gccgttctcc agcaagccat ttcctagctt attaatgaga gagagagaga 3660
gagggggggg ggtctgtatt ctgcgagcaa ttcaaaaact tccattgttc tgaggtgtac 3720
gcattgtagg gatctcccat tatgaagagg atatagttaa ttcttttgtaa cctacttgga 3780
aacttgagtc ttgcggcatc gctaatatat tctatcatca caatacttag aggatgcatc 3840
tgaatatttt agtgggatct tgcacaggaa ccgaagataa attcatatgc taattttagg 3900
gatgaggtgc tgccaagaat taaaaggctt ggatacaatg cagtgcagat aatggcaatc 3960
caggagcatt catactatgc gagctttggg tattcacaca atccattttt ttctgttctt 4020
tttctgtat gcgcctcttc acccatttgg agctattaca tcctaatgct tcgtgcacat 4080
agaatatttg gatataattc tttagtagac atatagtaca acaacagttg gtatttctga 4140
cttgtatgac cattttattg ttgttggctt gttccaggta ccatgttact aatttttttg 4200
caccaagtag ccgttttgga actccagagg acttaaaatc cctgatcgat agagcacatg 4260
agcttggttt gcttgttctt atggatattg ttcataggta agtagtccaa ttaatttag  4320
ctgctttact gtttatctgg tattctaaat ggcagggccg tatcgacgag tattttccca 4380
ttctatataa ttgtgctaca tgacttcttt tttctcagat gtattaaacc agttggacat 4440
caaatgtatt tggtacatct agtaaactga cagtttcaaa gaacatcgtt ttgtaatgcc 4500
aacatgattt gatgccatag atgtggactg agaagttcag atgctatcaa gaaaattaat 4560
caactggcca tgtactcgtg gcactacata gagtttgcaa gttggaaaac tgacagcaat 4620
acctcactga taagtagcta ggccccactt gccagcttca tattagatgt tacttccctg 4680
ttgaactcat ttgaacatat tacttaaagt tcttcatttg tcctaagtca aacttctta  4740
agtttgacca agtctactga aaaatatatc aacatctaca acaccatt ggcttcatta  4800
gattcacaat ttttatttg taatattagc acaccttga tgttgtagat atcagcacat  4860
ttttctacag acttggtcaa atatagaaa gtttgactta ggacaaatct agaacttcaa  4920
tcaatttgga tcagaggga tagtccatac tggttgatta tatccggtaa catcaaataa  4980
tatagataga tgtcaacact ttaacaaaaa aatcagacct tgtcaccaaa tatgtatcag 5040
accatctgtt tgctttagcc acttgttttc atatttatgt gtttgtacct aatctatttt 5100
tacttctact tggtttggtt gatttttttt cagttgcatt gcttcatcaa tgattttgtg 5160
taccctgcag tcattcatca aataaatacc ttgacggctt gaatggtttc gatggcactg 5220
atacacatta cttccacggt ggtccacgtg gccatcattg gatgtgggat tctcgtcgtg 5280
tcaactatgg gagttgggaa gtatgtagct ctgacttctg tcaccatatt tggctaactg 5340
ttcctgttaa atctgttctt acacatgtcg atattctatt cttatgtagg tattgagatt 5400
cttactgtca aacgcgagat ggtggcttga agaatataag tttgatggat ttcgatttga 5460
tggggtgacc tccatgatgt atactcacca tggattacaa gtaagtcatc aagtggtttc 5520
agtaactttt ttagggcact gaaataattg ctatgcatca taacatgtat catgatcagg 5580
acttgtgcta cggagtctta gatagttccc tagtacgctt gtacaatttt acctgatgag 5640
atcatggacg attcgaagtg attattattt attttcttc taagtttgct tcttgttcta 5700
gatgacattt actgggaact atggcgagta tttggattt gctactgatg ttgacgcgtg 5760
agtttacttg atgctggtca acgatctaat tcatggactt catcctgatg ctgtatccat 5820
tggtgaagat gtaagtgctt acagtattta tgattttaa ccagttaagt agttttattt 5880
tgggatcagg ctgttactct ttttgttagg ggtaagatct ctcttttcat aacaatgcta 5940
atttatacct tgtatgataa tgcatcactt aggtaatttg aaaagtgcaa ggccattcaa 6000
gcttacgagc atatttttg atggctgtaa tttatttgat agtagttcag ttgggttt   6060
tcagtaaatg ggagtgtgtg actaatgttg cattagaaat gggcaacctt gtca       6114

SEQ ID NO: 2           moltype = AA   length = 527
FEATURE                Location/Qualifiers
source                 1..527
                       mol_type = protein
                       organism = Triticum aestivum
SEQUENCE: 2
MATFAVSGAT LGVARPAGAG GGLLPRSGSE RRGGVDLPSL LLRKKDSSRA VLSRAASPGK   60
VLVPDGESDD LASPAQPEEL QIPEDIEEQT AEVNMTGGTA EKLESSEPTQ GIVETITDGV  120
TKGVKELVVG EKPRVVPKPG DGQKIYEIDP TLKDFRSHLD YRYSEYRRIR AAIDQHEGGL  180
EAFSRGYEKL GFTRSAEGIT YREWAPGAHS AALVGDFNNW NPNADTMTRD DYGVWEIFLP  240
NNADGSPAIP HGSRVKIRMD TPSGVKDSIS AWIKFSVQAP GEIPFNGIYY DPPEEEKYVF  300
QHPQPKRPES LRIYESHIGM SSPEPKINSY ANFRDEVLPR IKRLGYNAVQ IMAIQEHSYY  360
ASFGYHVTNF FAPSSRFGTP EDLKSLIDRA HELGLLVLMD IVHSHSSNNT LDGLNGFDGT  420
DTHYFHGGPR GHHWMWDSRL FNYGSWEVLR FLLSNARWWL EEYKFDGFRF DGVTSMMYTH  480
HGLQMTFTGN YGEYFGFATD VDAVVYLMLV NDLIHGLHPD AVSIGED             527

SEQ ID NO: 3           moltype = DNA   length = 10219
FEATURE                Location/Qualifiers
source                 1..10219
                       mol_type = unassigned DNA
                       organism = Triticum aestivum
```

SEQUENCE: 3

```
tgagatctgg gccactgacc gactcactcg ctgcgcgggg atggcgacgt tcgcggtgtc    60
cggcgcgacc ctcggtgtgg cgcggcccgc cagcgccggc ggcggactgc tgcgatccgg   120
ctcggagcgg aggggcgggg tggacttgcc gtcgctgctc ctcaggaaga aggactcctc   180
tcgtacgcct cgctccctcc aatctccccg tctgtttttg ggcccccttc tctctccctc   240
gcctctctgc cgcgcatgg cctgttcgat gctgttcccc agttgatctc catgaacgag    300
agagatagct ggattaggcg atcgcctcag gccctggtgt taccacggct ttgatcatct   360
cctcctttca tgctgatatt ttctcactct ttcttctgtt cttgctgtaa ctgcaagttg   420
tagcattttt ttggcgaata agttgtagca ttgtctcact attgtactca tccttgcatt   480
tgcaggcgcc gtcctgagcc gcgcggcctc tcccagggaag gtcctggtgc ctgacggtga   540
gagcgacgac ttggcggcca ctccagcgca acccgaagaa ttacaggtac acaccgtcgt   600
gccggaaaat cttcatgcac ccgttattca cttaccaaat atcggatgaa ccaagccgcg   660
gaggcatcag gtttcaagct tcttctatca gcattgtgca ctacttcact gccttgtgca   720
gtttgttagc tgtggccccg cgctggctct tgggccactg aaaactcaga tggatgtgca   780
ttctagcaag aacttcacaa aataatgcac tgtttgtggt ttcgttagtc tgctctacaa   840
ttgctatttt tcgtgtgctg tagatacctg aagatatcga ggagcaaacg gctgaagtga   900
acatgacagg ggggactgca gagaaacttc aatattcaga accgactcag ggcattgtgg   960
aaacaatcac tgatggtgta accaaaggag ttaaggaact agtcgtgggg agagaaaccgc  1020
gagttgtccc aaaaccagga gatgggcaga aaatatacga gattgaccca acgctgaaag  1080
atttttcggag ccatcttgac taccggtaat gcctacccgc taatttcgct cattttgaat  1140
taaggtcctt tcatcatgca aatttgggga acatcaaaga ggcaaagact agggaccact  1200
gtttcataca gttcccctca tggtctgaga atatgctggg aagtatatgt ataattgctg  1260
gctacaattg gctcataatt gcaatacaaa taactgtctc cgatcattac aattacagag  1320
tggcaaactg atgaaaatgt ggtggatggg ttatggattt tactttgcta attcctctac  1380
caaattcctg gggaaaaaat ctaccagttg ggcaacttag tttcttatct ttgttgcctt  1440
tttgttttgg ggaaaacaca ctgctaaatt tgaatgattt tgggtatgcc ttggtggatt  1500
caacagatac agcgaataca agagaattcg tgctgctatt gaccaacatg aaggtggatt  1560
ggaagcattt tctcgtggtt atgaaaagct tggatttacc cgcaggtaaa tttaaagctt  1620
tactatgaaa cgcctccact agtctaattg catatcttgt aagaaaattt ataattcctg  1680
ttttccccctc tctttttttcc agtgctgaag gtatcatcta attgcttatc ttataagaaa  1740
atttataatt cctgtttccc ccctcttttt tccagtgctg aaggtatcac ttaccgagaa  1800
tgggctcctg gagcgcatgt acgtcttaac agacaccttc taatctattg ttaatggtca  1860
ctattcacca actagcttac tgaacttaca aaatagctta ctgaatactg accagttact  1920
ctaaatttat gatctggctt ttgcatcctg ttacagtctg cagcattagt aggtgacttc  1980
aacaattgga atccaaatgc agatactatg accagagtag gtctacagct tggcaatctt  2040
ccacctttgc ttcgtaacta ctgatacatc tatttgtatt tatttaactg tttgcacgtt  2100
cgttaaagtt gagcctcaac tatatcatac caaaatggta taatttgtca gtgtcttaag  2160
cttcagccta aagatcctac tgaatttagt ccatcctttt gagattgaaa atgagtatat  2220
taagggtgat tgaatacttg caacactccc attttttggt agaaccttt tgcattatgtg  2280
tgcttttcca tccacaatga gcatatttcc atgttatcag tgaaggtttg ctcctattga  2340
tgccgatatt tgatatgatc tttcgatctt tcaggatga ttatggtgtt tgggagatct   2400
tcctcctaa caatgctgat ggatccccag ctattcctca tggctcacgt gtaaaggtaa   2460
tctgtgccaat tatttagtcg aggatgtaac attttcgaac tctgcctact aagggtccct  2520
tttcctctct attttctaga tacgatggaa tactccatct ggtgtgaagg attcgatttc  2580
tgcttggatc aagttctctg tgcaggctcc aggtgaaata ccattcaatg gcatatatta  2640
tgatccacct gaagagtaa gtatcaatct atgttacatt attaaatgga atttccagtg   2700
ttacagtttt ttgatatccca cttcatgtct cactgacatg tgagtcaaga caatactttc  2760
gaatttggaa gtgacatatg cattaattca ccttctaagg gctaagggc aaccaaccat   2820
ggtgatgtgt gtatgcttgt gtgacttaag atcttatagc tcttttatat gttctctgtt   2880
ggttaggaca ttccattttg acctttgtg accatttact aaggatattt tacatgcaaa   2940
tgcaggagaa gtatgtcttc caacatcctc aacctaaacg accagagtca ctaaggattt   3000
atgaatcaca cattggaatg agcagcccgg tatgtcaata agttatttca cctgtttccg  3060
gtctgatggt ttattctatg gattttctag ttctgttatg tactgttaac ataccacacg   3120
gtgcattcac gtgacaacct cgatttttat ttctaatgtc ttcatattgg aaaatgcaca  3180
actttgcttc ctctttttgct gatcgttttt ttgtctctaa gattccatt gcatttcgag  3240
gtagcgggca tgtgaaagtc gaatctgaat attttttgc agagcacagt tatattaaat   3300
gccattgttg ttgcaaatagc ttggtataat gtagccatgt tactagctta agaaatatcg  3360
cattggagca tctccagcaa gccatttcct accttattac tgagggggg ggggggggg   3420
agcggggttc tgtattctgc gagcgattca aaacttccac tgttctgagg tgtacgtact  3480
gtagggatct cccattatga agaggacata gttaacttt tgtaacctac ttggaaactt   3540
gagtcttgat gcatcgctac tatatactat catcacaata cttagaggat gcatctgaat  3600
atttagcgt gatcttgcac aggaaccgaa gataaattca tgctaatt ttagggatgg    3660
ggtgctgcca agaattaaaa ggcttggata caatgcagtg cagataatgg caatccagga  3720
gcattcatac atgcaagct ttgggtattc atacagtcca tcttttctg ttttttttt    3780
ctgtatgtgc ctcttcaccc atttcgagcc attcatcct aatgcttcgt gcacataaaa   3840
tacttggata taattctta ttagacatat agtacaacac cacttagtat ttctgacttg   3900
tatgatcatt ttattgttgt tggcttgtta caggtaccat gttactaatt tttttgcacc  3960
aagtagccgt tttggaactc cagaggactt aaaatccttg atcgatagag cagacacatg  4020
gcttgctgcctt gttcttatgg atattgttca taggtaatca gtccaattta atttagttg  4080
ctttactgtt tatctggtat tgtaaatggc agggccctat cgtcgaatat ttttccaatc  4140
tatataattg tgctacatga cttatttttt ctcagatgta ttaaaccagt tggatattaa  4200
atgtatttg tacatctagt aaaactgacag tttcatagaa ttgtgttgta atggcaacac  4260
aatttgatgg catagatgtg gactgagaag ttcagatgct atcagtaatt aattactgg   4320
ccatgtactc gtgaactac aactagtttg caagtggaa aactgacagc aatacctcac   4380
tgataagtgt ccaggccaca cttgccagct tcatattaga tgttacttcc ctgttgaact  4440
cctttgaaca tatcacttaa agttcttcaa ttgtcctaag tcaaacttct ttgactttgg   4500
ccaagtctat tgaaaatat gtcaacatct acagcaccaa attagtttca aatttttat    4560
tttgttatat tagcacgttt tttatgctgt agatatcagc acatttttct atagacttgg   4620
tcaaatatag agaagtttga cttaggacaa atcagaactt caagcaattt ggatcagagg  4680
```

```
gaatagtcca tactgcttga ttatattttc ccaaaggagg gagtgaggag cttgacttcg   4740
gtatcatcaa atgatattga tagatgtcaa cattttaaca aaaaatcaga ccttgtcacc   4800
aaatatgcat cagaccatct gttttgcttag gcacttgctt tcatatttat gtgtttgtaa   4860
ctaatctact tttccttcta cttggtttga ttgattctat ttcagttgca ttgcttcatc   4920
aatgattttg tgtaccctgc agtcattcgt caaataatac ccttgacggt ttgaatggtt   4980
tcgatggcac tgatacacat tacttccacg gtggtccacg tggccatcat ggatgtggg    5040
attctcgtct gttcaactat gggagttggg aagtatgtag ctgcgacttc tgtcaccatg   5100
tttggctaac tgttcctgcc aatctgttct tacacgtgtc aatattctat tcttatacag   5160
gtattaagat tcttactgtc aaacgcgaga tggtggcttg aagaatataa gtttgatgga   5220
tttcgatttg atggggtgac ctccatgatg tatactcacc atggattaca agtaagtcat   5280
caagtggttt cagtgaacttc ttcagggcac tgaaacaatt gctatgcatc ataacatgta   5340
tcatgatcag tacttatgct acggagtctt agatagttcc ctagtatgct tgtacaattt   5400
tacctgatga gatcatggaa gattggaagt gattgttatt atttttcctt ctaagtttgc   5460
ttcttgttct agatgacatt tactgggaac tatggcgagt attttggatt tgccactgat   5520
gttgatgcgg tggtatactt aatgctggtc aacgatctaa ttcatggact ttatcctgat   5580
gctgtatcca ttggtgaaga tgtaagtgct tacagtattt atgtttttta gtatttatt    5640
ttggggatca agctgttact actctttttg ttagggtaaa atctgtcttt tcataagaat   5700
gctaatttat actccctccg tctggaaata cttgtcggag gaatgaatgt atctagacgt   5760
attttagttc tagatacatc cattttttatg catttctccg tcaagtattt ccggacggag   5820
ggagtacctt gtatggtaat gcatcacata ggtaatttga gaagtgcaag ggcattcaag   5880
ctgacaagca tatttgttga tggctgtaat ttatttgata gtatgcttgt ttggatttt    5940
cagtaagtgt gagtgtgtga gtaatgttat attatttatt tacttgcgga agaaatgtgc   6000
aaccttgtca attgcttcag aagactaact tagattccat aaatgctgtg gaaatgagag   6060
gctattccca aggacacgaa attatacgtc agtgtgttac gcacatgtat ttgtaagagc   6120
aagagcaaca tggtttaact taaattcctg cactgctatg gaatctcact gtatgttgtt   6180
agtgtacgca tccacaaaca gtaatcctg agctttcaac tcacgagaaa ataggaggct    6240
ccacttctgc cagcattagc tgttcacagt tctaatttgt gtaactctga aattgttcag   6300
gtcagtggaa tgcctacatt ttgcatccct gttccagatg gtggtgttgg ttttgactat   6360
cgcctgcata tggctgtagc agataaatgg atcgaactcc tcaagtaagt gcaggaatat   6420
tggtgattac atgcgcacaa tgatctactc cctctgtccc attatgtaag atgttttttg   6480
acactagtgt agtgtcaaaa aacgtcctat attatgggaa ggagggagta gttcacaatt   6540
tctaaattgt aaaaagaaaa atatgtatgt gaatagctag acatttccct ggtatcagct   6600
tcaacacaag aagatttatc aaatacgatga tttaaatagc aaatttcgga aatgtaatgg   6660
ctagtgtctt tatgctggat attgtacatg gcgctgtagc aggtgagtca ataaagctag   6720
cgatatttc agaaacaaaaa taatcattta tatctgtata tggggaaagt gggggtatag   6780
atggtggtca ttaatcgtgt tcactttttg tcctgtataa gcacaggcag taggtaataa   6840
atttagccag ataaaataaa tcgttattag gtttacaaaa ggaatacaga gggtcatgta   6900
gcatatctag ttgtagttat tgtaaaggct gacaagaggt tcagtaaaaa aaactttatg   6960
ttgatcccgg gtatgcaaga acgcgagtaa agctcaaaca tttatagtgg ttgctgttgc   7020
ttgctgtata cttgtatctg cgcatatatg aaattactac tacacagctg ccaatctgcc   7080
atgatctgtg ttttgctttg tgctatttaa atttttaaatg ctaactcaat aaatgcaat    7140
aataaactaa ctattcaacc aatttgatgg atatcagaga tttcttccct cctttagtaa   7200
cattgtgctc ctgctgctgt tctctaccgt tacaaaagct gtttttccat ttttcgcatc   7260
attattttttg tgtgtgagta atttaagcat gtccttgaaa gctgtgagct gttggtactt   7320
agtacattct tggtagtgtc caaatatgct gcagtctaat ttagcatttc tataacacag   7380
gcaaagtgac gaatcttgga aaatgggtga tattgtgcac accctaacaa atagaaggtg   7440
gcttgagaag tgcgtcactt atgcagaaag tcatgatcaa gcactagttg gtgacaagac   7500
tattgcattc tggttgatgg ataaggtact agctcgttact tttggatcaa aagaatcaca   7560
taagatttgt ctcatcagat tgctcatgtt ttccttgtgat aaagatttgg ccccctcacc   7620
catcaccagc tatttcccaa ctgtcacttg agcaaaacgt gccatgtggc actgtggtgg   7680
cttgtgaact ttgacagtta atgttgcaaa tttctgttct tattttatttg attcttatgt   7740
tatcgttcat ttattcctca aaaaaatgtta tcgttcattt gctcattcct ttccgagacc   7800
agccgaagtc acgtgtagcc atgtgatctg ccatctgaat cttgagcaaa ttttatgaag   7860
aggctaaagt cgaacggatt atttgcttga atttataaat atacagacgt ataatcacct   7920
ggtgcttct gaaatgatta ccatagtgcc tgaaggctga aatagttttg gcgttttcctg   7980
gacgacgccc aaaggagtga attttattgg gtagatttct ggctgagccc tggttacaac   8040
atacattttg gagatatgct taataacaaa tctgggtgtt tggtcacgag tctgcatcta   8100
catgctcctt gggttttatt atggcgtcat cttttgtaact agtggcaccc ctaaggaaac   8160
attcaaaagg aaactgttac atcattctag tcaggaccac cgtactaaga gcaaaattct   8220
gttccaattt tatgagtttt tgagactcca aaatgaacat aagtgtctca tatttttgcta   8280
attaactaca gatgttttta tatcacttta gtttttattt caggacagtt gatacttggt   8340
actgtgctgt aagcattgat ccgacacaga acagcatgaa catttcgagc tctctttgtg   8400
caggatatgt atgatttcat ggctctggat agaccttgcaa ctcctcgcat tgatcgtggc   8460
atagcattac ataaaatgat caggcttgtc accatgggtt taggtggcga aggctatctt   8520
aacttcatgg gaaatgagtt tgggcatcct ggtcagtctt tacaacatta ttgcattctg   8580
catgttgtgc atttactgta atttgaacca tgctttgttt tcacattgta tgtattatgt   8640
aatctgttgc ttccaaggag gaagttaact tctatttact tggcagaatg gatagatttt   8700
ccaagaggtc cgcaaactct tccaaccggc aaagtttctc ctggaaataa caatagttat   8760
gataaatgcc gccgtagatt tgatcttgta agtttagct gtgctcttac gttccctcac    8820
tagatcttta ttggctattt atttcttgat gaaatcataa tgtttgttga tcaacattgc   8880
ttttgtagtt ttgtagacgt taacataaat atgtgttaag agttattgat cattaagaat   8940
atcatgattt tttttgtagg gagatgcaga ttttcttaga tatcgtggta tgcaagagtt   9000
cgaccaggca atgcagcatc ttgaggaaaa atatgggta tgtcagtatg tcactggttt    9060
gtctttgttg catgcaagt cacagtttga cgcagtctc ttcaaatggt caaaagtgt     9120
agaattaatt cctgtaatga gatgaaaact gcgcaaaggc gggagctgga attgcttttc   9180
accaattaaa actattttct taagcgattg tgtattgata cctataccaa cactgacaat   9240
gtaactgcag tttatgacat ctgagcacca gtatgtttca cggaaacatg aggaagataa   9300
ggtgatcatc ttcgaaagag gagattttggt atttgttttc aacttccact ggagcaatag   9360
ctttttttgac taccgtgttg ggtgttccaa gcctgggaag tacaaggtat gcttgccttt   9420
```

-continued

```
tcattgccca ccccttcacca gtagggttag tgggggcttc tacaacttttt aattccacat   9480
gtagagtttg ttgttcgtgc agctatcaat ataaagaata ggataatttg taaagaaaag   9540
aatttgttgc tcgagatgtt gtagtcatat aacatccccg aagcacatct actattcatt   9600
catattatct acttaagggt ttgttacaat ctttgtactc agttggactc actctaatac   9660
tggaactatt taccgaatct accctaatca tcctagcagt tttagagcag ccccatttgg   9720
acagtccact gggtttagtt ggtttgtgac agtttctgct atttcttaat caggtggcct   9780
tagactccga cgatgcactc tttggtggat tcagcaggct tgatcatgat gtcgactact   9840
tcacaaccgt aagtctgggc tcaagcgtca cttgactcgt ctagactcaa ctgcttacaa   9900
atctgaatca acctcccatt tgctgatgcc cttgcaggaa catccgcatg acaaatgggc   9960
gcgctctttc ttggtgtaca ctcctagcag aactggcgtc gtgtatgccc ttacagagta  10020
agaaccagca gcggcttgtt acaaggcaaa gagagaactc cagggagctc gtggattgtg  10080
agcgaagcga cgggcaactg cgtgaggctg ctctaagcgc catgactggg aggggatcgt  10140
gcctcttccc ctgatgccag gaggatcaga tggataggta gcttgttggg aaaaatatgg  10200
ggtatgtcag tatgtcact                                                10219
```

```
SEQ ID NO: 4            moltype = AA   length = 823
FEATURE                 Location/Qualifiers
source                  1..823
                        mol_type = protein
                        organism = Triticum aestivum
SEQUENCE: 4
MATFAVSGAT LGVARPASAG GGLLRSGSER RGGVDLPSLL LRKKDSSRAV LSRAASPGKV    60
LVPDGESDDL AATPAQPEEL QIPEDIEEQT AEVNMTGGTA EKLQYSEPTQ GIVETITDGV   120
TKGVKELVVG EKPRVVPKPG DGQKIYEIDP TLKDFRSHLD YRYSEYKRIR AAIDQHEGGL   180
EAFSRGYEKL GFTRSAEGIT YREWAPGAHS AALVGDFNNW NPNADTMTRD DYGVWEIFLP   240
NNADGSPAIP HGSRVKIRMD TPSGVKDSIS AWIKFSVQAP GEIPFNGIYY DPPEEEKYVF   300
QHPQPKRPES LRIYESHIGM SSPEPKINSY ANFRDGVLPR IKRLGYNAVQ IMAIQEHSYY   360
ASFGYHVTNF FAPSSRFGTP EDLKSLIDRA HELGLLVLMD IVHSHSSNNT LDGLNGFDGT   420
DTHYFHGGPR GHHWMWDSRL FNYGSWEVLR FLLSNARWWL EEYKFDGRRF DGVTSMMYTH   480
HGLQMTFTGN YGEYFGFATD VDAVVYLMLV NDLIHGLYPD AVSIGEDVSG MPTFCIPVPD   540
GGVGFDYRLH MAVADKWIEL LKQSDESWKM GDIVHTLTNR RWLEKCVTYA ESHDQALVGD   600
KTIAFWLMDK DMYDFMALDR PSTPRIDRGI ALHKMIRLVT MGLGGEGYLN FMGNEFGHPE   660
WIDFPRGPQT LPTGKVLPGN NNSYDKCRRR FDLGDADFLR YRGMQEFDQA MQHLEEKYGF   720
MTSEHQYVSR KHEEDKVIIF ERGDLVFVFN FHWSNSFFDY RVGCSKPGKY KVALDSDDAL   780
FGGFSRLDHD VDYFTTEHPH DNRPRSFLVY TPSRTAVVYA LTE                     823
```

```
SEQ ID NO: 5            moltype = DNA   length = 11475
FEATURE                 Location/Qualifiers
misc_feature            4795
                        note = n is a, c, g, or t
misc_feature            4973
                        note = n is a, c, g, or t
misc_feature            5078..5079
                        note = n is a, c, g, or t
misc_feature            5082
                        note = n is a, c, g, or t
misc_feature            7010
                        note = n is a, c, g, or t
misc_feature            7327
                        note = n is a, c, g, or t
misc_feature            7381
                        note = n is a, c, g, or t
misc_feature            7384
                        note = n is a, c, g, or t
misc_feature            7819
                        note = n is a, c, g, or t
misc_feature            8189
                        note = n is a, c, g, or t
source                  1..11475
                        mol_type = unassigned DNA
                        organism = Aegilops tauschii
SEQUENCE: 5
agaaacacct ccattttaga ttttttttttt gttctttttcg acggtgggt cgtggagaga     60
ttagcgtcta gttttcttaa aagaacaggc catttaggcc ctgctttaca aaggctcaa    120
ccagtccaaa acgtctgcta ggataccag ctgcaaagtt aagcgcgaga ccaccaaaac    180
aggcgcattc gaactggaca gacgctcacg caggagccca gcaccacagg cttgagcctg    240
acagcggacg tgagtgcgtg acacatgggg tcatctatgg gcgtcggagc aaggaagaga    300
gacgcacatg aacaccatga tgatgctatc aggcctgatg gagggagcaa ccatgcacct    360
tttccctct ggaaattcat agctcacact ttttttttaat ggaagcaaga gttggcaaac    420
acatgcattt tcaaacaagg aaaattaatt ctcaaaccac catgacatgc aattctcaaa    480
ccatgcaccg acgagtccat gcgaggtgga aacgaagaac tgaaaatcaa catcccagtt    540
gtcgagtcga aagaggatg acactgaaag tatgcgtatt acgatttcat ttacatacat    600
gtacaaatac ataatgtacc ctacaatttg ttttttggag cagagtggtg tggtcttttt    660
ttttacacg aaaatgccat agctggcccg catgcggtag tcggcgatga tcggtttgag    720
acgacggaca atcagacact caccaactgc ttttgtctgg gacacaataa atgtttttgt    780
aaacaaaata aatacttata aacgagggta ctagaggccg ctaacggcat ggccaggtaa    840
acgcgctccc agccgttggt ttgcgatctc gtcctcccgc acgcagcgtc gcctccaccg    900
tccgtccgtc gctgccacct ctgctgtgcg cgcgcacgaa gggaggaaga acgaacgccg    960
cacacacact cacacacggc acactccccg tgggtcccct ttccggcttg gcgtctatct   1020
```

```
cctctccccc gcccatcccc atgcactgca ccgtacccgc cagcttccac ccccgccgca   1080
cacgttgctc ccccttctca tcgcttctca attaatatct ccatcactcg ggttccgcgc   1140
tgcatttcgg ccggcgggtt gagtgagatc tgggcgactg gctgactcaa tcactacgcg   1200
gggatggcga cgttcgcggt gtccggcgcg actctcggtg tggcgcgggc cggcgtcgga   1260
gtggcgcggg ccggctcgga gcggaggggc ggggcggact tgccgtcgct gctcctcagg   1320
aagaaggact cctctcgtac gcctcgctct ctcgaatctc ccccgtctgg ctttggctcc   1380
ccttctctct cctctgcgcg cgcatggcct gttcgatgct gttccccaat tgatctccat   1440
gagtgagaga gatagctgga ttaggcgatc gcgcttcctg aacctgtatt ttttcccccg   1500
cggggaaatg cgttagtgtc acccaggccc tggtgttacc acggctttga tcattcctg   1560
tttcattctg atatatattt tctcattctt ttcttcctg ttcttgctgt aactgcaagt   1620
tgtggcgttt tttcactatt gtagtcatcc ttgcattttg caggcgccgt cctgagccgc   1680
gcggcctctc cagggaaggt cctggtgcct gacggcgaga gcgacgactt ggcaagtccg   1740
gcgcaacctg aagaattaca ggtacacaca ctcgtgccgg taaatcttca tacaatcgtt   1800
attcacttac caaatgccgg atgaaaccaa ccacgatgc gtcaggtttc gagcttcttc   1860
tatcagcatt gtgcagtact gcactgcctt gttcattttg ttagccttgg ccccgtgctg   1920
gctcttgggc cactgaaaaa atcagatgga tgtgcattct agcaagaact tcacaacata   1980
atgcaccgtt tggggtttcg tcagtctgct ctacaattgc tatttttcgt gctgtagata   2040
cctgaagata tcgaggagca aacggcgaa caggggggac tgcagagaaa   2100
cttcaatctt cagaaccgac tcagggcatt gtggaaacaa tcactgatgg tgtaaccaaa   2160
ggagttaagg aactagtcgt gggggagaaa ccgcgagttg tcccaaaacc aggagatggg   2220
cagaaaatat acgagattga cccaacactg aaagattttc ggagccatct tgactaccgg   2280
taatgcctac ccgctgcttt cgctcatttt gaattaaggt cctttcatca tgcaaatttg   2340
gggaacatca aagagacaaa gactagggac caccatttca tacagatccc ttcgtggtct   2400
gagaatatgc tgggaagtaa atgtataatt gatggctaca atttgctcaa aattgcaata   2460
cgaataactg tctccgatca ttacaattaa agagtggcaa actgatgaaa atgtggtgga   2520
tgggttatag atttttacttt gctaattcct taccaaaatt cctaggggg aaatctacca   2580
gttgggaaac ttagtttctt atctttgtgg ccttttgtt ttggggaaaa cacattgcta   2640
aattcgaatg attttgggta tacctcgtgt gattcaacag atacagcgaa tacaagagaa   2700
ttcgtgctgc tattgaccaa catgaaggtg gattggaagc attttctcgt ggttatgaaa   2760
agcttggatt tacccgcagg taaatttaaa gcttattat tatgaaacgc ctccactagt   2820
ctaattgcat atcttataag aaaatttata attcctgttt tcccctctct tttttccagt   2880
gctgaaggta tcgtcaatt gcatatctta aagaaaatt tatattcctg ttttccccta   2940
ttttccagtg ctgaaggtat cacttaccga gaatgggctc ctggagcgca tgttatgttc   3000
ttttaagttc cttaacgaga caccttccaa tttattgtta atggtcacta ttcaccaact   3060
agcttactgg acttacaaat tagcttactg aatactgacc agttactata aatttatgat   3120
ctggcttttg caccctgtta cagtctgcag cattagtagg tgacttcaac aattggaatc   3180
caaatgcaga tactatgacc agagtatgtc tacagcttgg caattttcca cctttgcttc   3240
ataactactg atacatctat ttgtatttat ttagctgttt gcacattcct taaagttgag   3300
cctcaactac atcatatcaa aatgtataa tttgtcagtg tcttaagctt cagcccaaag   3360
attctactga atttagtcca tcttttgag attgaaaatg agtatattaa ggatgaatga   3420
atacgtgcaa cactcccatc tgcattatgt gtgcttttcc atctacaatg agcatatttc   3480
catgctatca gtgaaggttt gctccattg atgcagatat ttgatatggt cttttcagga   3540
tgattatggt gtttgggaga ttttcctccc taacaacgct gatggatcct cagctattcc   3600
tcatggctca cgtgtaaagg taagctggcc aattatttag tcgaggatgt agcattttcg   3660
aactctgcct actaagggtc ccttttcctc tctgttttt agatacggat ggatactcca   3720
tccggtgtga aggattcaat ttctgcttgg atcaagttct ctgtgcaggc tccaggtgaa   3780
ataccttttca atggcatata ttatgatcca cctgaagagg taagtatcga tctacattac   3840
attattaaat gaaatttcca gtgttacagt ttttaatac ccacttctta ctgacatgtg   3900
agtcaagaca atacttttga atttggaagt gacatatgca ttaattcacc ttctaagggc   3960
taaggggcaa ccaaccttgg tgatgtgtgt atgcttgtgt gtgacataag atcttatagc   4020
tcttttatgt gttctctgtt ggttaggata ttccattttg gccttttgtg accatttact   4080
aaggatattt acatgcaaat gcaggagaag tatgtcttcc aacatcctca acgtaaacga   4140
ccagagtcac taaggattta tgaatcacac attggaatga gcagcccggt atgtcaataa   4200
gttatttcac ctgtttctgg tctgatggtt tattctatgg attttctagt tctgttatgt   4260
actgttaaca tattacatgg tgcattcact tgacaacctc gatttattt tctaatgtct   4320
tcatattggc aagtgcaaaa cttgcttcc tctttgtctg cttgttcttt tgtcttctgt   4380
aagatttcca ttgcatttgg aggcagtggg catgtgaaag tcatatctat tttttttttg   4440
tcagagcata gttatatgaa ttccattgtt gttgcaatag ctcggtataa tgtaaccatg   4500
ttactagctt aagatttccc acttaggatg taagaaatat tgcattggag cgtctccaga   4560
aagccatttc ctaccttatt aatgagatgag agacaagggg gcatggggggg gggggttcc   4620
cttcattatt ctgcgagcga ttcaaaaact tccattgttc tgaggtgtac gtactgcagg   4680
gatctcccat tatgaagagg atatagttaa ttctttgtaa cctacttgga aacttgagtc   4740
ttgaggcatc gctaatatat actatcatca caatactag aggatgcatc tgaanatttt   4800
agtgtgatct tgcacaggaa ccgaagataa attcatatgc taattttagg gatgaggtgt   4860
tgccaagaat taaaaggctt ggatacaatg cagtgcagat aatggcaatc caggagcatt   4920
catactatgc aagctttggg tattcacaca atccattttt ttctgtatac acntcttcac   4980
ccatttggag ctattacatc ctaatgcttc atgcacataa aatatttgga tataatccttt  5040
tattagatat atagtacaac tacacttagt attctganna anaagatcat tttattgttg   5100
ttggcttgtt ccaggtacca tgttactaat tttttgcac caagtagccg ttttggaact   5160
ccagaggact taaaatcctt gatcgataga gcacatgagc ttggtttgct tgttcttatg   5220
gatattgttc ataggtaatt agtccaattt aattttagct gttttactgt ttatctggta   5280
ttctaaaggg aaattcaggc aattatgata cattgtcaaa agctaagagt ggcgaaagtg   5340
aaatgtcaaa atctagagtg gcataaggaa aattggcaaa aactgagtg gcaaaaataa   5400
aattttccca tcctaaatgg caggggccta tcgccgaata tttccatt ctatataatt   5460
gtgctacgtg acttcttttt tctcagatgt attaaaccag ttggacatga aatgtatttg   5520
gtacatgtag taaactgaca gttccataga atatcgtttt gtaatggcaa cacaatttga   5580
tgccatagat gtggattgag aagttcagat gctatcaata gaattaatca actggccatg   5640
tactcgtggc actacatata gtttgcaagt tggaaaactg acagcaatac ctcactgata   5700
agtggccagg ccccacttgc cagcttcata ctagatgtta cttccctgtt gaattcattt   5760
```

```
gaacatatta cttaaagttc ttcatttgtc ctaagtcaaa cttctttaag tttgaccaag   5820
tctattggaa aatatatcaa catctacaac accaaattac tttgatcaga ttaacaattt   5880
ttatttattt atattagcac atctttgatg ttgtagatat cagcacattt ttctatagac   5940
ttggtcaaat atagagaagt ttgacttagg acaaatctag aacttcaatc aatttggatc   6000
agagggaaca tcaaataata tagatagatg tcaacacttc aacaaaaaaa tcagaccttg   6060
tcaccatata tgcatcagac catctgtttg cttttagccac ttgctttcat atttatgtgt   6120
ttgtacctaa tctactttc cttctacttg gtttggttga ttctatttca gttgcattgc   6180
ttcatcaatg attttgtgta ccctgcagtc attcgtcaaa taataccctt gacggtttga   6240
atggtttcga tggcactgat acacattact tccacggtgg tccacgcggc catcattgga   6300
tgtgggattc tcgtctattc aactatggga gttgggaagt atgtagctct ggcttctgtc   6360
accatatttg gctaactgtt cctgttaatc tgttcttaca catgttgata ttctattctt   6420
atgcaggtat tgagattctt actgtcaaac gcgagatggt ggcttgaaga atataagttt   6480
gatggatttc gatttgatgg ggtgacctcc atgatgtata ctcaccatgg attacaagta   6540
agtcatcaag tggtttcagt aacttttta gggcactgaa acaattgcta tgcatcataa   6600
catgtatcat gatcaggact tgtgctacgg agtcttagat agttccctag tatgcttgta   6660
caattttacc tgatgagatc atggaagatt ggaagtgatt attatttatt ttcttttctaa   6720
gtttgttct tgttctagat gacatttact gggaactatg gcgaatattt tggatttgct   6780
actgatgttg atgcggtagt ttacttgatg ctggtcaacg atctaattca tggacttat   6840
cctgatgctg tatccattgg tgaagatgta agtgcttaca gtatttatga ttttaacta   6900
gttaagtagt tttattttgg ggatcagtct gttacacttt ttgttagggg taaaatctct   6960
cttttcataa caatgctaat ttatacctg tatgataatg catccacttan gtaatttgaa   7020
aagtgcaagg gcattcaagc ttacgagcat attttttgat ggctgtaatt tatttgatag   7080
tatgcttgtt tgggttttc aataagtggg agtgtgtgac taatgttgta ttatttattt   7140
aattgcggaa gaaatgggca accttgtcaa ttgcttcaga aggctaactt tgattccata   7200
aacgctttgg aaatgagagg ctattcccaa ggacatgaat tatacttcag tgtgttctgt   7260
acatgtattt gtaatagtgg tttaacttaa attcctgcac tgctatggaa tctcactgta   7320
tgttgtaagt gtacacatcc acaaacaagt aatcctgagc tttcaactca tgagaaaata   7380
ngangtccgc ttctgccagc attaactgtt cacagttcta atttgtgtaa ctgtgaaatt   7440
gttcaggtca gtgaatgcc tacattttgc atccctgttc cagatggtgg tgttggtttt   7500
gactaccgcc tgcatatggc tgtagcagat aaatggattg aactcctcaa gtaagtgcag   7560
gaatattggt gattacatgc gcacaatgat ctagattaca ttttctaaat ggtaaaaagg   7620
aaaatatgta tgtgaatatc tagacatttg cctgttatca gcttgaatac gagaagtcaa   7680
atacatgatt taaatagcaa atctcggaaa tgtaatggct agtgtctta tgctgggcag   7740
tgtacattgc gctgtagcag gccagtcaac acagttgaca atattttcag aaacaatatt   7800
atttatatcc gtatatgang aaagttagta tataaactgt ggtcattaat tgtgttcacc   7860
ttttgtcctg tttaaggatg ggcagtaggg aataaaattta gccagataaa ataaatcgtt   7920
attaggttta caaaaggaat atacagggtc atgtagcata tctagttgta attaatgaaa   7980
aggctgacaa aaggctcggt aaaaaaaact ttatgatgat ccagatagat atgcaggaac   8040
gcgactaaag ctcaaatact tattgctact acacagctgc caatctgtca tgatctgtgt   8100
tctgctttgt gctatttaga tttaaatact aactcgatac attggcaata ataaacttaa   8160
ctattcaacc aatttggtgg ataccagana ttttctgccct cttgttagta atgatgtgct   8220
ccctgctgct gttctctgcc gttacaaaag ctgttttcag tttttttgcat cattatttt   8280
gtgtgtgagt agtttaagca tgttttttga agctgtgagc tgttggtact taatacattc   8340
ttggaagtgt ccaaatatgc tgcagtgtaa tttagcattt cttaacaca ggcaaagtga   8400
cgaatcttgg aaaatgggcg atattgtgca caccctaaca aatagaaggt ggcttgagaa   8460
gtgtgtaact tatgcagaaa gtcatgatca agcactagtt ggtgacaaga ctattgcatt   8520
ctggttgatg gataaggtac tagctgttac ttttggacaa aagaattact ccctccgttc   8580
ctaaatataa gtcttttgtag agattccact atggaccaca tagtatatag atgcatttta   8640
gagtgtagat tcactcattt tgcttcgtat gtagtccata gtgaaatctc tacagagact   8700
tatatttagg aacggaggga gtacataatt gatttgtctc atcagattgc tagtgttttc   8760
ttgtgataaa gattggctgc ctcaccccatc accagctatt tcccaactgt tacttgacga   8820
gaatttgctg aaaacgtacc atgtggtact gtggcggctt gtgaactttg acagttatgt   8880
tgcaattttc tgttcttatt tatttgattg cttatgttac cgttcatttg ctcattcctt   8940
tccgagacca gccaaagtca cgtgttagct gtgtgatctg ttatctgaat cttgagcaaa   9000
ttttattaat aggctaaat ccaacgaatt atttgcttga atttaaatat acagacgtat   9060
agtcacctgg ctcttttctta gatgattacc atagtgcctg aaggctgaaa tagttttggt   9120
gtttcttgga tgccgcctaa aggagtgatt tttattggat agattcctgg ccgagtcttc   9180
gttacaacat aacattttgg agatatgctt agtaacagct ctgggaagtt tggtcacaag   9240
tctgcatcta cacgctcctt gaggttttat tatggcgcca tcttttgtaac tagtggcacc   9300
tgtaaggaaa cacattcaaa aggaaacggt cacatcattc taatcaggac caccatacta   9360
agagcaagat tctgttccaa ttttatgagt ttttgggact ccaaagggaa caaaagtgtc   9420
tcatattgtg cttataacta cagttgtttt tataccagtg tagttttatt ccaggacagt   9480
tgatacttgg tactgtgctg taaattattt atccgacata gaacagcatg aacatatcaa   9540
gctctctttg tgcaggatat gtatgatttc atggctctgg ataggccttc aactcttcgc   9600
attgatcgtg gcatagcatt acataaaatg atcaggcttg tcaccatggg tttaggtggt   9660
gaaggctatc ttaacttcat gggaaatgag tttgggcatc ctggtcagtc tttacaacat   9720
tattgcattc tgcatgattg tgatttactg taatttgaac catgctttc tttcacattg   9780
tatgtattat gtaatctgtt gcttccaagg aggaagttaa cttctattta cttggcagaa   9840
tggatagatt ttccaagagg cccacaaact cttccaaccg gcaaagtct ccctgggaaat   9900
aacaatagtt atgataaatg ccgccgtaga tttgatcttg taagttttag ctgtgctatt   9960
acattccctc actagatctt tattggccat ttatttcttg atgaaatcat aatgtttgtt  10020
aggaaagatc aacattgctt ttgtagtttt gtagacgtta acataagtat gtgttgagag  10080
ttgttgatca ttaaaaatat catgattttt tgcaggagga tgcagatttt cttagatatc  10140
gtgtatgca agagttcgat caggcaatgc agcatcttga ggaaaaatat ggggtatgtc  10200
actggtttgt ctttgttgca taacaagtca cagtttaacg tcagtctctt caagtgtaa  10260
aaaaagtgta gaattaattc ctgtaatgag atgaaaactg tgcaaaggcg gagctggaat  10320
tgcttttcac caaaactatt ttcttaagtg cttgtgtatt gatacatata ccagcactga  10380
caatgtaact gcagtttatg acatctgagc accagtatgt ttcacggaaa catgaggaag  10440
ataaggtgat catcctcaaa agaggagatt tggtattgt tttcaacttc cactggagca  10500
```

```
atagcttttt tgactaccgt gttgggtgtt ccaagcctgg gaagtacaag gtatgcttgc    10560
cttttcattg tccacccttc accagtaggg ttagtggggg cttctacaac ttttaattcc    10620
acatggatag agtttgttgg tcgtgcagct atcaatataa agaatagggt aatttgtaaa    10680
gaaaagaatt tgctcgagct gttgtagcca taggaaggtt gttcttaaca gccccgaagc    10740
acataccatt cattcatatt atctacttaa gtgtttgttt caatctttat gctcagttgg    10800
actcggtcta atactagaac tattttccga atctacccta accatcctag cagttttaga    10860
gcagccccat ttggacaatt ggctgggttt tgttagttg tgacagtttc tgctatttct     10920
taatcaggtg gccttggact ctgacgatgc actctttggt ggattcagca ggcttgatca    10980
tgatgtcgac tacttcacaa ccgtaagtct gggctcaagc gtcacttgac tcgtcttgac    11040
tcaactgctt acaaatctga atcaacttcc caattgctga tgcccttgca ggaacatccg    11100
catgacaaca ggccgcgctc tttctcggtt tacactccga gcagaactgc ggtcgtgtat    11160
gcccttacag agtaagaacc agcagcggct tgttacaagg caaagagaga actccagaga    11220
gctcgtggat cgtgagcgaa gcgacgggca acggcgcgag gctgctccaa gcgccatgac    11280
tgggagggga tcgtgcctct tccccagatg ccaggaggga cagatggata ggtagcttgt    11340
tggtgagcgc tcgaaagaaa atggacgggc ctgggtgttt gttgtgctgc actgaaccct    11400
cctcctatct tgcacattcc cggttgtttt tgtacatata actaataatt gcccgtgcgc    11460
tcaacgtgaa aatcc                                                      11475

SEQ ID NO: 6          moltype = AA   length = 819
FEATURE               Location/Qualifiers
source                1..819
                      mol_type = protein
                      organism = Aegilops tauschii
SEQUENCE: 6
MATFAVSGAT LGVARAGVGV ARAGSERRGG ADLPSLLLRK KDSSRAVLSR AASPGKVLVP    60
DGESDDLASP AQPEELQIPE DIEEQTAEVN MTGGTAEKLQ SSEPTQGIVE TITDGVTKGV    120
KELVVGEKPR VVPKPGDGQK IYEIDPTLKD FRSHLDYRYS EYKRIRAAID QHEGGLEAFS    180
RGYEKLGFTR SAEGITYREW APGAHSAALV GDFNNWNPNA DTMTRDDYGV WEIFLPNNAD    240
GSSAIPHGSR VKIRMDTPSG VKDSISAWIK FSVQAPGEIP FNGIYYDPPE EEKYVFQHPQ    300
RKRPESLRIY ESHIGMSSPE PKINSYANFR DEVLPRIKRL GYNAVQIMAI QEHSYYASFG    360
YHVTNFFAPS SRFGTPEDLK SLIDRAHELG LLVLMDIVHS HSSNNTLDGL NGFDGTDTHY    420
FHGGPRGHHW MWDSRLFNYG SWEVLRFLLS NARWWLEEYK FDGFRFDGVT SMMYTHHGLQ    480
MTFTGNYEGY FGFATDVDAV VYLMLVNDLI HGLYPDAVSI GEDVSGMPTF CIPVPDGGVG    540
FDYRLHMAVA DKWIELLKQS DESWKMGDIV HTLTNRRWLE KCVTYAESHD QALVGDKTIA    600
FWLMDKDMYD FMALDRPSTL RIDRGIALHK MIRLVTMGLG GEGYLNFMGN EFGHPEWIDF    660
PRGPQTLPTG KVLPGNNNSY DKCRRRFDLG DADFLRYRGM QEFDQAMQHL EEKYGFMTSE    720
HQYVSRKHEE DKVIILKRGD LVFVFNFHWS NSFFDYRVGC SKPGKYKVAL DSDDALFGGF    780
SRLDHDVDYF TTEHPHDNRP RSFSVYTPSR TAVVYALTE                             819

SEQ ID NO: 7          moltype = DNA   length = 4431
FEATURE               Location/Qualifiers
source                1..4431
                      mol_type = unassigned DNA
                      organism = Triticum aestivum
SEQUENCE: 7
atggcgtcgc cggcattcgc agtttccgcg gcgggcctcg cccggccgtc ggctcctcga    60
tccggcgaca cagagcggag ggggcgcggg gtggagctga agtcgccatc gctgctcttc    120
ggccgcaaca agggcacccg ttcaccccgt aattattggc gctaccttcc tcactcccat    180
tctcgtttat tcgtagcggg ctgcggttca gcgaccttac gttccctcct ggtgtggtga    240
tgtctgtagg tgccgtcggc gtcggaggtt ctggatggcg cgtggtcatg cgcgcgggtg    300
ggccgtccgg ggaggtgatg atccctgacg gcggtagtgg cggaacaccg ccttccatcg    360
acggtcccgt tcagttcgac tctgatgatc tgaaggtagt ttttatttct ttccttgcta    420
gtaccttcct gcatgacaat tgaaatctaa gacaaaaaca ccatatgcga agcctacacg    480
gtaggttggt ttacaactat gtgtgccaca gttcgtctga acttttttgtc cttcacatcg    540
tgttaggttc cattcatcga tgatgaaaca agcctacagg atggaggtga agatactatt    600
tggtcttcag agacaaatca ggttactgaa gaaattgatg ctgaaggcac gagcagaatg    660
gacaaagaat catctacggg agagaaatta cgcattctgc caccaccggg aaatggacag    720
caaatatacg agattgaccc aacgctccga gactttaagt accatcttga gtatcggtat    780
gcttcgttc tattgtgtgc actttaaact ttaaatacaa tttacagtct ttgataaagat    840
gtgaatggct gcttgctgtg acacaaaact cttgaagttc gtagtcactc ttgtgtgttc    900
atggctctga ggtgacatgg taaccgaaca aaaataggaa agtggcaaga actgcaatgt    960
gagctaccga taagcaccca ttgtaattgg gtacactgat taatatatgt cttgatgggt    1020
tctatgtttt ttcagtatct atgccaattg aacaacaatg ccacttcatt tccccctgtgt    1080
tgcttttgta aggatgaaac ccatatgtcc agatcaaact gtactagcag tctcactgtg    1140
ccttaatgga tcaaaaacag atacagccta tataggagaa tacgttcaga cattgatgaa    1200
cacaaaggag gcatggatgt attttcccgc ggttacgaga gtttggatt tgtgcgcagg     1260
tgaaatttct tgactagata agtatgtatc taccttttt ctgtatcgta tctacattcc    1320
tcttcccatg cagcgctgaa ggtatccttc accgagaatg ggctcctgga gcagatgtat    1380
gttcttctga ctgtctgatc gtttacctaa gtatactagt tctatcttc aactgcttgt    1440
gaataattag tgctcatctg ctatcctaag gttgggattt tgcacttcc cagatgaaca     1500
gcatattaag ttgcacaact agctttattt agaactaact cttgcttcca attgcagtct    1560
gcagcattag ttggcgactt caacaattgg gatccaaatg cagaccatat gagcaaagta    1620
tgcatgtagt ttcacaaata tataatttttt tctttgtaaa tttgttcttt aagatctgct    1680
tactattaa atgtggttga atatcacct tatatgtatt ccggagttga gctgtgaata    1740
tagttggaag tgtttaggag tattaaagtc actagactct attctttcac ttgcctgttg    1800
cacgagccca ttaattacta gatatcaatg ttgatgatgc tttcgttgta taacgtcaaa    1860
ttgacaacat gcatgttacc cttttatata agtaatgctg cacaaatatt tttgatgatt    1920
tagacatgat ttaatgattt tggttattgc aagacactga gcggttttac atagtaatgg    1980
tattggagta ggctgactgg ataacccgtg aactgtagct ccatgtggtt gatatggatt    2040
```

```
tacaaatgct catattcaat ttaattgttt tcagaatgac ttgggtattt gggagatttt  2100
tctgccaaac aatgcagacg gttcgccacc aattcctcac ggctcacggg tgaaggttgt  2160
tttcttctcc tcgccaactg tgttaggctc aggaacatgt tctgtattac tcacaagctc  2220
ttttgaacat ctaggtgcga atgggtactc catctgggac aaaggattca attcctgctt  2280
ggatcaagta ctccgtgcag actccaggag atataccata caatggaata tattatgatc  2340
ctcccgaaga ggtattttac ttcgtcttct gtgcttttag atttcagata ttttttaattg  2400
gaaagaaaat tatgatttgt ttttctcacg aagcttccca agtgttattt caagttgttc  2460
tacttcttat ttgttgttgg catcttagtt ttctattcac taaccagtta tgaaattctt  2520
acatgcatgt gcaggagaag tatgtattca agcatcctca acctaaacga ccaaaatcat  2580
tgcggatata tgaaacacat gttggcatga gtagcccggt atttcatctt taccctgtat  2640
tccataaatg aagttagcta tatgcaattc aagttaattt acaatttgtt acaatgtat  2700
ttttgtgttg ttggccttct ttcgttttat aagtaaaaag cttatcataa atttatgtgt  2760
tatgccactt ggttaataca atctgaaaaa tgtaactgtg gacaatctag aactagataa  2820
tacaaatctg aaaaaacatg ctggaaatagt gtcatttcag tcaaataga tgttttgaat  2880
gctcgagaga agtactagat tgtgtagcat caaaagctgg tgtccatttg ttcgaacgtt  2940
ttacttgatg taactgtgaa tgttacatct tttgctacta aagttcattt tttcactata  3000
ttacatgttt catcaacaac ttaattaacc tcattcctta caaacatttg tatttacatt  3060
tgttcctaca taaatggtta ttttatatat caacttatga atcctgaacg ttataattaa  3120
gaccgatggt atatcaacga ttgagataat ttggcatatg cggatgaatt ttgtggcttg  3180
ttatgctctt gttttaataa tataataaat agattatgct tgttggtagc cttttttacat  3240
taacacatgg gcaattactt gtttctttgt gcaaccagga accaaagatc aacacatatg  3300
caaactttcg ggatgaggtg cttccaagaa ttaaaagact tgggtacaat gcagtgcaaa  3360
taatggcaat ccaagagcac tcatactatg gaagctttgg gtagttctct gggtcgattt  3420
ctgattcttt tagttatttt ttgtccatgg aacatatttc aacttagca actatactat  3480
tatattaact tttcagctat tctcttcctt ttcttactag taaagtatgt gtgtgcaatg  3540
cacgtattag gtaggatatt agtggcacgt tatattagt aaaatatatt tatggcacat  3600
tgatatttgc taagatatta attgcttct tcgcgggaat ggtaaaatat taattacatg  3660
acagatttca tgggatagcg ttgagtctaa acatgtttat aaccaatgat agtgatgggt  3720
aattagagcg ttaaacatgt ttggtgctca acattggagc gatttgaact gctagattac  3780
atgattttgac ggttgagatg gttttggatct gcccctttgg gtcttttttgt attggtatag  3840
atgtgagaga ctgctgcttc ttgctacttc ctgtgttctc attctgagta gatatcttat  3900
gagtggacaa ctctatgtcg acattctgga agtatcactg gttgatttgg tctaaaataa  3960
catactgcac agatagccac ataacagtgc gattacacac ataatgacca tgtttgcata  4020
gagtggcggt agtatgttcc tcaccatact agcatatga tttgttatat aggagtatat  4080
catattaact tcttttccaa tgacatgaa gctgtaacaa ctttcaaatc atatttgtct  4140
tttaagtgct gcttttttcc tgtttgacaa ttaatacaat accacttta tgtgttttta  4200
cttctattgc aggtaccatg ttaccaattt ctttgcacca agtagccgtt ttgggtcccc  4260
agaagattta aatctttga ttgatagagc tcacagcct ggcttggttg tcctcatgga  4320
tgttgttcac aggtacttaa tgtaatttgc cgttggcgtg ttaggttcac attaatctta  4380
attctttatt tcaattccta tggcctctct cctagatgga acagtaaaag c             4431

SEQ ID NO: 8           moltype = AA  length = 416
FEATURE                Location/Qualifiers
source                 1..416
                       mol_type = protein
                       organism = Triticum aestivum
SEQUENCE: 8
MASPAFAVSA AGLARPSAPR SGGPERRGRG VELQSPSLLF GRNKGTRSPR AVGVGGSGWR   60
VVMRAGGPSG EVMIPDGGSG GTPPSIDGPV QFDSDDLKVP FIDDETSLQD GGEDTIWSSE  120
TNQVTEEIDA EGTSRMDKES STGEKLRILP PPGNGQQIYE IDPTLRDFKY HLEYRYSLYR  180
RIRSDIDEHK GGMDVFSRGY EKFGFVRSAE GITYREWAPG ADSAALVGDF NNWDPNADHM  240
SKNDLGIWEI FLPNNADGSP PIPHGSRVKV RMGTPSGTKD SIPAWIKYSV QTPGDIPYNG  300
IYYDPPEEEK YVFKHPQPKR PKSLRIYETH VGMSSPEPKI NTYANFRDEV LPRIKRLGYN  360
AVQIMAIQEH SYYGSFGYHV TNFFAPSSRF GSPEDLKSLI DRAHELGLVV LMDVVH      416

SEQ ID NO: 9           moltype = DNA  length = 4727
FEATURE                Location/Qualifiers
source                 1..4727
                       mol_type = unassigned DNA
                       organism = Triticum aestivum
SEQUENCE: 9
gcctcctcat ttcgctcgcg tgggtttaag caggagacga ggcggggtca gttgggcagt   60
taggttggat ccgatccggc tgcggcggca gcgacgagat ggcgtcgccg gcattcgcag  120
tttccggggc gggctgcc cggccgtcga ctcctcggca cggggggca gagcggaggg  180
ggcgcgggt ggagctgcag tcgccatcgc tgctcttcgg ccgcaacaag gcacccgtt  240
caccccgtaa tttttggcgc caccttcctc actccattc tcgtttattc gcagcgggct  300
gcggttcagc gatcttacgt tccctactgg tgtggtgatg tctgtaggtg ccgtcagcgt  360
cggaggttct ggatggcgcg tggtcatgcg cgcgggtggg ccgtccgggg aggtgatgat  420
ccctgacggc ggtagtggcg gaacaccgcc ttccatcgac ggtcccgttc agttcgactc  480
tgatgatctg aaggtagttt ttctttttcct ttttttgcat cgatctgaag gtagttgaca  540
tatattaccc tgactaaact attactgcca ccgtattttt atggttcgct tgaaatacct  600
gtttacttgc tacggtttgc actttcattg agacgtcaga agaaattcac tgaattccta  660
taatttggta gacaccgaaa tatgtacctt ttaggtcaaa atattccggc agttaagttt  720
cagttgtata caagaattca aatatatata tttctcaata aattggttta  780
gtttcaagtg aacgttttgg tcctttggtc gagaagtaaa ccgaaatcac tgaaattcac  840
tgaatttcag tagtggccga aactttatata gaactgaaat tcaaaatctg ctattcggcg  900
aaattatata ctaagatttt gcttatttca cacgtaggtt gcggaatatc ctcttctaa  960
tttgttgggg aatggttctt attatcttgt cagtacctgc ctgcatgaca attgaaatcc 1020
aagacaaaac accatatgcg aggcctacac gctaggttgg ttttacaact atgtgtgcca 1080
```

```
cagttcttct gaacttttg tcttgcacat tgtgttaggt tgcattcatc gatgatgaac   1140
caagcctaca ggatgaaggt gaagatagta tttggtcttc agagacaaat caggttactg   1200
aagaaattga tgttgaaggc acgaacataa tggacaaaga atcatctacg ggggagaaat   1260
tacgcattgt gccaccacca ggaaatggac agcaaatata cgagattgac ccaacgctcc   1320
gagacttcaa gtaccatctt gagtatcggt atgattcgct tctattgtgt gcactttaaa   1380
agaatttaca gtcttcgcta agatgtgaat ggctgcttga tgtatcacga aattcttgaa   1440
gttcatagtc actcttgtgt gttcatggtt ctgaggtaac ttggtaaccg aacaaaataa   1500
ggaaagtgca agcactgcaa tgtgagctac tgataaccac ccattgtaat tgggtagact   1560
gattaatata tatgtcttca tgggctctat gtttcttttc aatatctatg ccaattgaac   1620
aacaatgctt tgtggacggg tgttcttta ccctctcctt ctatcaatag atgatacgaa   1680
tactcatgcg tattctacaa aaaattgaac aacgatgcca cttcatttcc cccgtgttgc   1740
ttttgtaagg atgaaacaca tatgtccaga tcaaactgta ctagcagtct cactgtgcct   1800
taatggatca aaaacagata cagcctatat aggagaaatac gttcagacat tgatgaacac   1860
gaaggaggca tggatgtatt ttcccgcggt tacgagaagt ttggatttat gcgcaggtga   1920
aatttcttga ctaaataact atgtatctac cttttctttg tattgtatca acattcctct   1980
tctcatgcag cgctgaaggt atcacttacc gagaatgggc tcctggagca gatgtatgtt   2040
cttctaacca tctgatcgtt tacctaacta tactagttcc atcttcaac tacttgtgaa   2100
taattactgc tcatcagcta tcctaaggtt ggggatttg cacctcccag atgaacagca   2160
tattaagtcg cacaactagc attattaaga actaactcct gcttccaatt gcagtctgca   2220
gcattagttg gcgacttcaa caattgggat ccaaatgcag accatatgag caaagtatgc   2280
atgtagtttc acaataata ttttcttgt agattagttt ttttttagat tggcctatct   2340
atttaaatgt ggttgaatat acaccttata tgtattccag agttgagctg taaatatagt   2400
tggttggaag tgtttaggag tttaaattca ctggactcta ttctttcact tgcctgttgc   2460
gcgagcccat tactagatat caatgttgat gatgcttttg ttgtatgagg tcgaagtgaa   2520
acatgcatgt tacccttta tataagtaag gttgcacatg tattttta gatctaaaca   2580
tcattactg attttgttct tgcaagacat tcagcagttt tacataataa tggtattgga   2640
gtaggccgac tgcatacctg aactgtagct ccatgtggtt gatatagatt tacaaatgct   2700
catattcaat gtaactgttt tcagaatgac ctcggtgttt gggagattt tctgccaaac   2760
aatgcagatg gttcgccacc aattcctcac ggctcacggg tgaaggttgt ttttttctcc   2820
ttgccaaccg tgttaggctc cagaacatgt cttgcattac cagaagctc ttttgaaaat   2880
ctaggtgaga atggatactc catctgggat aaaaggattca attcctgctt ggatcaagta   2940
ctccgtgcag actccaggag atataccata caatggaata tattatgatc ctcccgaaga   3000
ggtatttac ttcatttct gtgcttttag atttcagata ttttttaattg gaaagaaaat   3060
tatgattttt tttctcacga agcttcccaa ttgctatttc aagctgtcct acttctattt   3120
gctgttggca tcttatttt ctattcacta accagttatg aaattcctta catgcatatg   3180
caggagaagt atgtattcaa gcatcctcaa cctaagcgac caaaatcatt gcggatatat   3240
gaaacacatg ttggcatgag tagcccggta tttcatcttt accctgtatt ccataaatga   3300
aagttagcta tatgcagttt aagttaattt acaggttgtt acaatggtat ttttgtgttg   3360
ttgcccttct ttcgttttat aagtaaaaaa cttatcataa atttatttgt tatgccactt   3420
ggttaataca atctgaaaaa tgtaactgtg gacaatctag aactagataa tacaaatctg   3480
aaaaaacaag ctggaatagt gtcatttcag tcaaatagga tgttttgaat gctcgagaga   3540
agtactagat tgtgtagcat caaaagctgg tgtccatttg gtcaaatgtt taacttgatg   3600
taactgtgaa tgttacatct tttgctacta taagttcata ttttttcac tattacat   3660
gtttcatcaa caatttagtt aacctaattc cttacaaaca tttgtattta aatttgttcc   3720
tacatgtata tttattttat atatcaactt ataaatcctg accgttataa ttaagaccaa   3780
tggtatatca atgattgaga taatttggca tatgtggatg aattttgtgg cttgttatgc   3840
tcttgtttta ataataat aaatagatta tgcttgttgg tagccttta acattaacac   3900
atgggcaatt acttgtttct ttgtgcaacc aggaaccaaa gatcaacaca tatgcaaact   3960
tcagggatga ggtgcttcca agaattaaaa gacttggata taatgcagtg caaataatgg   4020
caatccaaga gcactcatac tatggaagct ttgggtagtt ctctgggtcg atttctggtt   4080
cttttagtta tttttttgtcc atagaaacata tttcaactt agcaactata ctagtatatt   4140
aactttttcag ctattgtctt cctttttctt atgtgagaga ctgctgcttc ttgctacttt   4200
ctgtgttctc attcagagta gacatcttat gagtggacaa ctctatgttg acattctgga   4260
agtatcactg gttggttttgg tctaaaataaa catactgctc agatagccac ataacagtat   4320
gattacacac acaatgacca tgtttgcata gagtggcggt agtatgttcc tcaccatact   4380
agcataatga tttgttatat aagagtatat catattaact tctttttccaa taacatggaa   4440
gccttaacaa ctttcaaatc gttttttgtct tttaagtgct gcttttttcc tgtttgacaa   4500
ttaatacaat accactttta tgtgtttcta cttctattgc aggtaccatg ttaccaattt   4560
ctttgcacca agtagccgtt ttgggtcccc agaagatttta aaatcattga ttgatagagc   4620
tcacgagctt ggcttggttg tcctcatgga tgttgttcac gatgacttaa tgtaatttgc   4680
ggttggcgtg ttaggttcac attaatctta attctttatt tcaattc              4727

SEQ ID NO: 10            moltype = AA  length = 415
FEATURE                  Location/Qualifiers
source                   1..415
                         mol_type = protein
                         organism = Triticum aestivum
SEQUENCE: 10
MASPAFAVSA AGLARPSTPR SGGAERRGRG VELQSPSLLF GRNKGTRSPR AVSVGGSGWR   60
VVMRAGGPSG EVMIPDGGSG GTPPSIDGPV QFDSDDLKVA FIDDEPSLQD EGEDSIWSSE  120
TNQVTEEIDV EGTNIMDKES STGEKLRIVP PPGNGQQIYE IDPTLRDFKY HLEYRYSLYR  180
RIRSDIDEHE GGMDVFSRGY EKFGFMRSAE GITYREWAPG ADSAALVGDF NNWDPNADHM  240
SKNDLGVWEI FLPNNADGSP PIPHGSRVKV RMDTPSGIKD SIPAWIKYSV QTPGDIPYNG  300
IYYDPPEEEK YVFKHPQPKR PKSLRIYETH VGMSSPEPKI NTANFRDEVL PRIKRLGYNA  360
VQIMAIQEHS YYGSFGYHVT NFFAPSSRFG SPEDLKSLID RAHELGLVVL MDVVH       415

SEQ ID NO: 11            moltype = DNA  length = 14896
FEATURE                  Location/Qualifiers
misc_feature             5
```

-continued

| | | |
|---|---|---|
| misc_feature | 35 | note = n is a, c, g, or t |
| misc_feature | 45 | note = n is a, c, g, or t |
| misc_feature | 66 | note = n is a, c, g, or t |
| misc_feature | 88 | note = n is a, c, g, or t |
| misc_feature | 103 | note = n is a, c, g, or t |
| misc_feature | 107 | note = n is a, c, g, or t |
| misc_feature | 137 | note = n is a, c, g, or t |
| misc_feature | 146 | note = n is a, c, g, or t |
| misc_feature | 154 | note = n is a, c, g, or t |
| misc_feature | 156 | note = n is a, c, g, or t |
| misc_feature | 168 | note = n is a, c, g, or t |
| misc_feature | 172 | note = n is a, c, g, or t |
| misc_feature | 206 | note = n is a, c, g, or t |
| misc_feature | 210 | note = n is a, c, g, or t |
| misc_feature | 230 | note = n is a, c, g, or t |
| misc_feature | 272 | note = n is a, c, g, or t |
| misc_feature | 274 | note = n is a, c, g, or t |
| misc_feature | 313 | note = n is a, c, g, or t |
| misc_feature | 374 | note = n is a, c, g, or t |
| misc_feature | 5514 | note = n is a, c, g, or t |
| misc_feature | 5541 | note = n is a, c, g, or t |
| misc_feature | 5574 | note = n is a, c, g, or t |
| misc_feature | 5586 | note = n is a, c, g, or t |
| misc_feature | 5602 | note = n is a, c, g, or t |
| misc_feature | 5619 | note = n is a, c, g, or t |
| misc_feature | 6366 | note = n is a, c, g, or t |
| misc_feature | 6596 | note = n is a, c, g, or t |
| misc_feature | 6604 | note = n is a, c, g, or t |
| misc_feature | 6623 | note = n is a, c, g, or t |
| misc_feature | 6676 | note = n is a, c, g, or t |
| misc_feature | 6746 | note = n is a, c, g, or t |
| misc_feature | 6787 | note = n is a, c, g, or t |
| misc_feature | 6803 | note = n is a, c, g, or t |
| misc_feature | 6845 | note = n is a, c, g, or t |
| misc_feature | 6864 | note = n is a, c, g, or t |
| misc_feature | 6877 | note = n is a, c, g, or t |
| misc_feature | 6963 | note = n is a, c, g, or t |
| misc_feature | 7055 | note = n is a, c, g, or t |
| misc_feature | 7123 | note = n is a, c, g, or t |

| | |
|---|---|
| misc_feature | 9161 |
| | note = n is a, c, g, or t |
| misc_feature | 9206 |
| | note = n is a, c, g, or t |
| misc_feature | 9284 |
| | note = n is a, c, g, or t |
| misc_feature | 10857 |
| | note = n is a, c, g, or t |
| misc_feature | 10861 |
| | note = n is a, c, g, or t |
| misc_feature | 10926 |
| | note = n is a, c, g, or t |
| misc_feature | 11177 |
| | note = n is a, c, g, or t |
| misc_feature | 11224 |
| | note = n is a, c, g, or t |
| misc_feature | 11336 |
| | note = n is a, c, g, or t |
| misc_feature | 12749 |
| | note = n is a, c, g, or t |
| misc_feature | 12771 |
| | note = n is a, c, g, or t |
| misc_feature | 12964 |
| | note = n is a, c, g, or t |
| misc_feature | 12984 |
| | note = n is a, c, g, or t |
| misc_feature | 12986 |
| | note = n is a, c, g, or t |
| misc_feature | 13126 |
| | note = n is a, c, g, or t |
| misc_feature | 13893 |
| | note = n is a, c, g, or t |
| misc_feature | 14086 |
| | note = n is a, c, g, or t |
| misc_feature | 14109 |
| | note = n is a, c, g, or t |
| misc_feature | 14156 |
| | note = n is a, c, g, or t |
| misc_feature | 14173 |
| | note = n is a, c, g, or t |
| misc_feature | 14517 |
| | note = n is a, c, g, or t |
| misc_feature | 14591 |
| | note = n is a, c, g, or t |
| source | 1..14896 |
| | mol_type = unassigned DNA |
| | organism = Aegilops tauschii |

SEQUENCE: 11

```
ttttncgggg ttgcttcttc cagattcata ttcgnaaaat ttcanatgga gcttaaaaat    60
aatgtngttg agctttttg agggtttnca aatggccaat tanaacnttg ggttttgaat   120
taattgaatc caatttngac caattnattt aagnantttt aaattgggat gnaaaacttt   180
tatttgaact attgtcgcct tggaantttn attttttgag tttaaaaggn cttgcgatat   240
ttttcttttg attgttttcc aacccatgta ananagtgcg ttaaaagagc aaaggtatac   300
gccaaagaag gcncacccat tacaaagcca cataggcatg acccaactaa agaacccaaa   360
ccattgatga ttcncaatta ataaacccac caaaatcagc ttaaattaga gcaagggcat   420
tacacatgca acaaagtagg caacattttc agtgcataag actacaatag acaacaacac   480
tatctcaaca cgaccacgac aacggacaac atcgaataaa acccaaagaa cacatgaaga   540
aggcatgacg tcactgagca aggaggctac aaatccacca ccgccgggcc gacttgccac   600
caaggccata gaaggaccgt ggggtgcata ggcataaacc agagcaggag gcacatgacc   660
aacaaagaca acatcaacca cgatcaagta ccacaacagg ggaggagtga gggaaaatgc   720
catcggagac tcgaagtgga cgttggagta ttttctttg attatttca atattcaaac   780
tacacaaagat caacaacaga tgagagacca aaacatttga taactacagt tggataatat   840
tggccatgat gtctgtttga tgatccgccc gagatgccaa gctttgtagc cttgcacggg   900
ctccccaaca aactgcctca ctcgattgtc aaaaaagtaa aaatgattgt agaaaaaaaa   960
actgactcac tcgtcactac cctaccgtcc tacatgacac ctggccgcaa gacgacgccg  1020
tcctcctgcc gcgcgcgtcc gcgatcacac caccgcaaaa accaaaacct cttcgccggt  1080
gcgtccacg ctaccatcca tgcagccgtc cgcccgcgcg cgcgttgccc gcaccacccg  1140
ctggcggcca ccacgccgcc actctcgcgt gaaggctccg tccgcttcct cctagttcca  1200
ctctctctcc gtgctagcag tatatagcat ccgccctccg ccccctccca atcttagaac  1260
accctccct ttgcctcctc atttcgctcg cgtgggttta agcaggagac gaggcggggt  1320
cagtgggca gttaggttgg atccgatccg gctgcggcgg cggcgacggg atggctgcgc  1380
cggcattcgc agtttccgcg gcggggctgg cccggccgtc ggctcctcga tccggcgggg  1440
cagagcggag ggggcgcggg gtggagctgc agtcgccatc gctgctcttc ggccgcaaca  1500
agggcacccg aattattgc gccacctttc tcactcacat tctctccgtgt  1560
attctgtcgt gctcgccctt cgccgacgac gcgtgccgat tccgtatcgg gctgcggtgt  1620
tcagcgatct tacgtcggtt ccctcctggt gtggtgatgt ctgtaggtgc cgtcggcgtc  1680
ggaggttctg gatggcgcgt ggtcatgcgc gcggggggc cgtccgggga ggtgatgatc  1740
cctgacggcg gtagtggcgg aacaccgcct tccatcgacg gtcccgttca gttcgattct  1800
gatgatctga aggtagtttt tttttgcat cgatctgaag gtacttgaca tatactactg  1860
```

```
tattaccctg agtaaatact gccaccatat ttttatggtt cgcttgaaat acctgtttac 1920
ttgctacggt tttcactttc attgagacgt cggacgaaat tcactgaatt cctataattt 1980
ggtagacacc gaaatatata ctactccttc cgtcccataa tataagagcg tttttggcac 2040
cttatattat agggcggagg gagtaccttt taggtcaaaa tattgtggta gtttcaattg 2100
tatacaagaa ttcaaatatt ttttttaaaa aaaaatcaac taattggttg agtttcaagt 2160
gaagcgtttt ggtcctttgg ctgagatgta aaccgaaatc actgaaattc atagtagccg 2220
aaactttaat agaactgaaa ctcaaaatct gctatccggc gaaattctaa agatttgctt 2280
atttcacacg taggttgcag tacaccctct ttctaattta ttggggaagg ggtattatta 2340
tcttgttagt acctgcctgc atgacaattg aaatctaaga caaaacacca tatgcgaggc 2400
ctacacacgg taggttggtt tacaactatg tgtgccacag ttcgtctgaa cttttttgtcc 2460
ttcacatcgt gttaggttcc attcattgat gatgaaacaa gcctacagga tggaggtgaa 2520
gatagtattt ggtcttcaga gacaaatcag gttagtgaag aaattgatgc tgaagacacg 2580
agcagaatgg acaaagaatc atctacgagg gagaaattac gcattctgcc accaccggga 2640
aatggacagc aaaatatacga gattgaccca acgctccgag actttaagta ccatcttgag 2700
tatcggtatg cttcgcttct attgtgtgca ctttaaaaac aatttacagt ctttgataag 2760
atgtgaatgc ctgcttgctg tgacacgaaa ctccttgaagt tcgtagtcac tcttgtgtgt 2820
tcatggttct gaggtaacat ggtaaccgaa caaaaatagg aaagtggcaa gcactgcaat 2880
gtgagctact gataaccacc cattgtaatt gggtacactg attaatatat atgtcttcat 2940
gggctctatt ttttttcaat atctatgcca attgaacaac aatgctttgt ggacgggtgt 3000
tcttttaccc tcttcttcta tcaatagatg atatgcatac tcatgcgtat cctacaaaaa 3060
attgaacaac aatgccactt tccccgtgt tgcttttgta aggatgaaac acatatgtcc 3120
agatcaaact atactagcag tctaactgtg ccttaatgga tcaaaaacag atatagccta 3180
tacaggagaa tacgttcaga cattgatgaa cacgaaggag gcatggatgt attttcccgc 3240
ggttacgaga agtttggatt tatgcgcagg tgaaatttct tgactaaata actatgtatc 3300
tacctttct ttgtactcta tcaacattcc tcttcccatg cagcgctgaa ggtatcactt 3360
accgagaatg ggctcctgga gcagatgtac gttcttctaa ccatctgatc gtttacctga 3420
ctatactaat tctatctttc aactaattgt gaataaattac tgctcatcag ctatcctaag 3480
gttgggatt ttgcacctcc cagatgaaca gcatattaag tcgcacaact agcattatta 3540
agaactaact cctgcttcca attgcagtct gcagcattag ttggcgactt caacaattgg 3600
gatccaaatg cagaccatat gagcaaagta tgcatgtagt ttcacaaata tatcatattt 3660
tctttgtaga tttttttttt tagatcggct tatctatttta aatgtggttg aatatacacc 3720
ttatatgtac gttgagctgt aaatatagtt ggaagtgttt aggagtatta aattcactgg 3780
actctattct ttcacttgcc tgttgcacga gcccattact agatatcaat gttgatgatg 3840
cttttgttgt atgaggtcga agtgaaacat gcatgttacc ctttttatata agtaaggttg 3900
cacatgtatt tttatgatc taaacattat ttactgattt tgttcttgca agacactaag 3960
cagttttaca taataatggc gttggagcag gccgactgca catctgaact gtagctccat 4020
gtggttgata tagattacaa atgctcatat tcaatgtaac tgttttcaga atgaccttgg 4080
tgtttgggag atttttctgc caaacaatgc agatggttcg ccaccaattc ctcacggctc 4140
acgggtgaag gttgttttct tctccttgcc aacggtgtta ggctcaggaa catgtcctgt 4200
attactcaga agctcttttg aacatctagg tgagaatgga tactccatct gggataaagg 4260
attcaattcc tgcttggatc aagtactccg tgcagactcc aggagatata ccatacaatg 4320
gaatatatta tgatcctccc gaagaggtat tttacttcat cttctgtgct tttagatttc 4380
agatatttt attagaagaa aattatgatt ttttccctca cgaaccttcc caattgctat 4440
ttcaagctgt cctacttatt tgctgctggc atcttatttt tctattctct aaccagttat 4500
gaaattcctt acatgcatat gcaggagaag tatgtattca agcatcctca acctaaacga 4560
ccaaaatcat tgcggatata tgaaacacat gttggcatga gtagcccggt atttcatctt 4620
taccatgtat tccataaatg aagttagcta tatgcagttc aaatttattt acaggttgtt 4680
acaatggtat ttttgtgttg gtgcccttct ttcgttttat aagtaaaaaa cttatcataa 4740
atttatttgt tatgccgctt ggttaataca atctgaaaaa tgtaactgtg gacaatctag 4800
aactagataa tacaaatctg aaaaaacatg ctggaatagt gtcatttcag tcaactagga 4860
tgttttgaat gctcaagaga agtactagtg tgtagcatca aaagctggtg tccatttgtt 4920
caaatgtttta attaacacta tagtgaaaac aagtaattgc acaaagaaac aagtaattgc 4980
ccaagttcat atgttttttc actatattac atgtttcatc aacaatttaa ttaacctcat 5040
tccttacaaa catttgtatt tacatttgtt cctacatata tagttatttt atatatcaac 5100
tttataaatc ttgactgtta taattaaaac cgatggtata tcaacgattg agataatttg 5160
gcatatgtgg atgaatttgt tggcttgtta tgctcttgtt ttaataacat aataaataga 5220
ttatgcttgt tggtagcctt tttacattaa cacatgggca attacttgtt tctttgtgca 5280
accaggaacc aaagatcgac acatatgcaa acttcaggga tgaggtgctt ccaagaatta 5340
aaagacttgg ataacatgca gtgcaaataa tggcaatcca agagcactca tactatggaa 5400
gctttgggta gttctctggg tcgatttctg gttcttttag ttatcttttg tccatagaac 5460
atatttcaac tttagcaact atactattat attaacttttt cagctattgt cttnctttt 5520
cttatgtgag agactgctgc ntcttgctac ttcctgtgtt ctcattcaga gtanacatct 5580
tatgantaga caactctatg tngacattcc ggaagtatnc actggctgat tcggtctaaa 5640
ataacatact gctcagatag ccacataaca gtacgattac acacataatg accatgtttg 5700
catagagtgg cggtagtatg ttcctcacca tactagcata atgacttgtt atataagagt 5760
atatcatatt aacttctttt ccaatgacat ggaagctgta acaactttca aatcattttt 5820
gtcttttaag tgctgctttt ttcctgtttg acaattaata caataccact tttatgtgtt 5880
tttacttcta ttgcaggtac catgttacca atttcttttgc accaagtagc cgttttgggt 5940
ccccagaaga tttaaaatct ttgattgata gagctcagga gcttggcttg gttgtcctca 6000
tggatgttgt tcacaggtac ttaatgtaat ttgaggttgg cgtgttaagt tcacattaat 6060
cttaattctt tatttcaatt cctatggcct ctctcctaga ttggaacagt aaaagcatca 6120
tccagtttgt ataaattgct aaaagaacat tttacatgtt aagtatttc aattactatg 6180
aaacatataa atttacatat ttattgattt tacgacagaa gtaccgatct cacaagatga 6240
acaattggtt gatcacatat cattcatac tacaataaca gaaaatgaat agagaacgag 6300
ttaatattag ccttggtaaa atcagcaact tgtttggaaa taaagtatag tgatgccagt 6360
gcaaanaaca aggcatcaag ttggtttcag ctcccacggt cggtgctagc tgtcaagggt 6420
aatttgcacg tagtcgcaca tagatttgtg tgggagtgga aagtaaccac agattgtccg 6480
aggaacacgg gacacacgtc ttagccacag gtttgggctc cccttgatgc gggtagtagc 6540
tttactcctt atatgaaatt atctcaagat agatttcaat ttggggttac acttangaac 6600
```

```
tcancaagtt aaggatcaac tcnctgagtt ctatacgact gatctttgac cgagatatct  6660
tgatcaggct aagtancaaa atccaggcct tgagatgttg aacatgtcct tcattttggg  6720
ctgggtgccc ttgggcataa ggtgtngtcc ttccttcatg tgcttcttgc agcgtatgac  6780
ataaacntcc tctgagttgg tanatgcacg gttcccttg aggaaatcag gggtagtcgc  6840
atctngggaa agttggtcac ccangcatgg atcctcngcg cacaccgggc aaacacggtg  6900
aaaccacttc tcctcgacac tagctaactt gacattcaag caaactaaga atataacttt  6960
atntctaaat gaaccggaca ccctccttgt gcctgcacct acagagtaca atgccagttt  7020
tggactgaac tcttgtgttc atgtatgtgc taatnacata ggttctaacc atgattctaa  7080
atagcgcgtt ataactccac tatagtaatg ctatagcgtt tanaagatcc cgcactaagg  7140
gaccttagtc caaatacatg atcaaacatt ttacatacg cgctatagct atttaaaact  7200
atggtcaccc gctaagaggc ataactcgct atttaaaact atggttctaa cttttaatct  7260
attttatgtc ttggtccaaa gccccttttt gttctatagc tttacctttg ggttgagatc  7320
acccttaacc cattggtaat cctggttgat ttactccatc ctttcttgcg tagcttttact 7380
tttggttttt tgtttctcac agtcacgcgt caaataatac cttggacggg ttgaatggtt  7440
ttgatggcac ggatacacat tacttccatg gcggttcacg gggccatcac tggatgtggg  7500
attcccgtgt gtttaactat gggaataagg aagtatggga ctatagaatt tctattgcca  7560
tttgttatgt atttatccat taattaatcc tccaaccgat attccaacat tgttatcttt  7620
atacaggtta taaggtttct actttccaat gcaaagatgt ggctagagga gtataagttt  7680
gatggtttcc gattcgatgg cgcgacctcc atgatgtata cccatcatgg attacaagta  7740
attcattgct tgattgtctt tgttctatct tgactacctg tgcaactta ataagattac   7800
gcctagctaa tattttcttt tatgttatag tatcaattt tatttgagct tgaaacctaa   7860
attacttttt ttttgaattg ctgcgctcta ttttaggtaa ccttacagg agctaccat   7920
gaatatttg gctttgccac tgatgtagat gcggtcgttt acttgatgct gatgaatgat  7980
ctaattcatg ggttttatcc tgaagccgta actatcggtg aagatgtaag tgtttctata  8040
gtcatctttc aatatgaatt tgttagaact attggtactt atcttttg tagtttaggc   8100
tattctgttc attcttacag gaggtgcata cagaagttgc tttagatttt gaaacgcagt  8160
gcacattgtg ccattacttt gtagctatat cgagttgaga cttgagagcc atggtaatca  8220
agttcctgac gtggcattgc attagatagt tgcatgtcta agttcctgac gtggagatag  8280
aagaaagaac gcacccccg cgtcgctcct ctcagggcga cacgggcgga gccctcaccc   8340
ccgccgccac agggagcatc cacccttctc gccgccgccg gagggcaaag   8400
accgcgcggc gtcgcggcgg tgggtgcggc ctgggctggc atctggcagc ggcgatttgg  8460
cctccctgc ccagaactgt gctgccgcg tttgtggcag cttgggcatc ggcagtggcc    8520
cgagtctgcg gtgcggcgt gtctggcgtc cggaggtgca gcgattgtgc ggttgtgtgg   8580
ctcaggctcg gagggcgtgc gggctgccag gtccggccag atctggcctc gagtggcttc  8640
gtacggggcg gtgctgttg cgggtccgtg ggccgaggtt cgggtgtggc tgctgcttgc   8700
ccggaccggt ggtgcgtaac gatgccgag cagcgtcctc gggtcgttga agtgggcgct   8760
cctccggcag cttcaggtgg tgattcgtcg cagcgggtgg tgcactgggg gtctcggctg  8820
attgtggtgc catggtggtg gtggttgttg gcggtagcaa agtgcctggt gcacacggct   8880
aggggtttgg cggatggaca gacttgatgc aatgccttag ggcatagtga atttcagcta  8940
agtacctagc accgaccttg gtcaatgccg ccgccgctgg tgtcttagga cgttgttgcc  9000
cttgttggag gcgtgttgtg gagccccttc acctccatgg gcatttagat ctcgagctct  9060
ctgggtgaaa acgccggctt tggctttggc cggagtgggc ggtggcggcg taaccgtcgc  9120
tccccccatg gggctgtagt cttggaggtc tagacttcgtg ntaagcgtca ggtggttggtg 9180
tggtcctgaa ggttcgtatc ggctangcag gagcacggtc tcagggccgg tgtggaagcc  9240
agagcagcag ctccggagag cgcatttgtt ttgcatggtg cccnagtctg gtcgcttggg  9300
tggcttgaac ccatccggtt cagtgggtac acagccttgg ggctggtgtg tggagaacgc  9360
ctttatgtta tagggtatca attttgttca cttgggtttac ggagtcgtcg actcgtctgg  9420
tacacgccct cagggccgat atgtgtctct ctgtgtgtgt ctgttgtgt gttgttgagg   9480
tttgtacgcc agggcggcgg ctccaagtcg tgttgtatgg tatcgactct ggtcgttaga  9540
gcgactgagt cgccggctca tttggggcgc agcctcggaa ctggtgtgtg tgtcacaggc  9600
tcacaactgt attagttttg agctagtttt ccttgttaac cggtcaatta aaattctctg  9660
gtatgaaaag gcagagctac tgtcagttac tagggaaaaa atgtttctgg catgaaaac   9720
tattttctat ccatttcatg tagtgacaac ttttcttttt cttgagtgag actactaact  9780
ttccatgaaa gtcagatgaa aatcaacaac ttctataaac aaacagaact ttccagaaat  9840
aaggaacaaa ttgttggata tatcagcaat ttttcaattt atttatttaa tacgaaagca  9900
tgatgatagt gctggcaaga tttaatccta attgtaatct aaacatgtga gtgcgtcat   9960
aaaacatgca tatctcttaa catagtgagt actggaaact catgaaccaa gcagaagtgg  10020
gatgaatgga tcatacccct cagtagcaaa agtaaggggt tagggccgtg caacagcag  10080
cattggcatt ggtggcctc tcaaggaac cattgttccc acccatggt ttggttgggg    10140
aagtcaagaa agtagtcgaa gtcgtggatg caaaaggaca gaagggagcc gtcagggtga  10200
catgctcccc aataaccta ttgatctcca cctggtgcat ggtctgttg cgtgccgcag    10260
agaaggtgcg cacatgtacc cactcctctt ctcatgctcc caatgggtca tgaagagagt  10320
tcttatatat tggtccaaat tctcctccac tccttgggtc ggactaaatt tccaaccatt  10380
tcatgaaacc actaatgggt ctttgagatt atgcaggaat tattaattat ataatattgc  10440
ccaaggccca tctaacttc aacaataata acttaattgt tcaactgagg tgttggtttt   10500
tcatttgaat tctcaggtta gtggaatgcc tacatttgcc cttcctgttc aagttggtgg  10560
ggttggtttt gactatcgct tacatatggc tgttccgac aaatggattg aacttctcaa   10620
gtaagtgttt caaaattggt atgacatatgt taatattta ctggacagaa gatttgattg   10680
tcagtgtata ttaatgcaat taaaatgttc ctttgcgtaa cactattgca catatggact  10740
tccacatgaa tgtccaaaaa catgtatcgt tattagtgta tttgattggg ccacaatgtg  10800
attatagttg tgatttcgta gtttatacag tataacaaca aaagtaggat acatgtncca  10860
nctttgggaa attcttataa tgatattaca cttttttaat cttgcatccc tcatcatttc  10920
tattgnctca gttgttctcaa gttctataaa aagtttggtt tcgtgttctg gttattgatg  10980
tggagtatct tgtatctgaa acatgaattg caacttttta ttctaaacag aggaaacgat  11040
gaagcttggg agatgggtaa tattgtgcac acactaacaa acagaaggtg gctgaaaaag  11100
tgtgttactt atgctgaaag tcacgatcaa gcacttgttg gagacaagac tattgcattc  11160
tggttgatgg acaaggnaac aacacattat ttctccagac tttaaatact aacattatt  11220
ttgnttcgca atttccttat atctatgatt tttaattata cttatctctc ttgatttcc   11280
tcccacaaa aatgcaagct agaatttttt tcctcatgaa agtatgcaaa gcttgngcct   11340
```

```
atgcattgat aaagtattta caagcctaag aataggcgac aaccgaccac tcaagcgaag    11400
tccacaatca aatggttgtc agacacgtta ccgaactact tttagcctaa atgacaacca    11460
cacaaacaca ctgggttgcc cttgctttgg ataaatcgat ggcccctaga ctgccggtcg    11520
cacctcggaa ctgccaaccg ccatggccgc ttgaatagtg aaccatcaca cattgccata    11580
tcctctacat gttgaaactt agtacgcaac cgtagtcgat cgtgccccca agatgccaca    11640
tcacgggatt ggcacatggc tgatgcaagt aggaaccact gaaaaagcca aggcttgtgt    11700
tcataccaat cgaaggaaaa ccttgaagaa caaagccatt agaaaggtat caacatcaac    11760
tggctacctc gtctgatcta ggtctgaatc gacaaaccng atttggcttt tcactctaag    11820
gattagacaa caggggatgg ggtaaattgg tattccttga caatgccccc aaggtggaaa    11880
cggtgttagg aaggcgtcac tagtccttt atacagactg ctaagtgcgg agacgggaat    11940
cgaacccgtg acctcaaggt tatgagcctc gtcggcattg acagtgggaa tatcaagtgc    12000
ccctaacact taggtgttcc catgtctaga aaaatcaatt ttaaatgttt caaaaaaaat    12060
cttttttgt gaatcttcat aaaacatgtg tttgcaaccc ctaaaaagta caaatccaaa    12120
ctcagaatac atataggaca acacaaaaga caatctaga tgtgaacatt gccattttg    12180
tttttttgatt ctattcatga tgatttgtct ttttcgttcc tccaagtatt ttgattttaa    12240
tttttagag gtcgtagaca catcctatga actttcacaa ctcttttttct agaatcgttt    12300
gaaacgttta aaaatgaatc tctagatatg gggaatgaca acgcccaagt gttgggagca    12360
ctattttttt ttcccacacc tacctggtgg ggatgggttt cgtttgaagc cgcatgacca    12420
ccactcatgc catgggtgca gccccatgaa ggctcctcaa caaaatgtat caccacccgc    12480
aatcacacta gctcgacagc ctgattgcca tgccatccca caacaaggaa ctaccatgca    12540
ttgcacatca ggaccaacat agactgactg caaggagctg aacatggtt taggagccta    12600
tgtacttgaa acctatacct gcagtagagat gcccgaccct acgacaacac actagaagca    12660
cacatcagca accctgggca aagcatgaca aatgatgcca ggtacatcca tccgtagatg    12720
ttgcaagatg acgccggacg ggaactaana gcatcttcaa taacttgtgg natgttagtt    12780
tgttacaaaa tatagtaatc tcttcaccaa taagccattc tacaaatact ccaatggagt    12840
gtatttagct tgtcgaatag gaggtgagag aatatatagg attgctctta ggtatcgtca    12900
agtgatgtaa gcgcaagccc tatggttgtc ccaatcttca taatttgtag gtggcaaagg    12960
ggancatcac aaagaacaca tagncntaaa gaggaaacac ccaaacaata ttctcatcac    13020
acatgtcctc tttagtttaa tgctttgcta accctaattt gagtccatgg tacagtttat    13080
acagcatagg gacgaagctg gtaggtagga gagggataca tggccncttg actcgatttc    13140
cacgcaggca tgggacgggc agtccaggtt gcaagcctga cagtctggtc gttgtagctc    13200
gtccggatca gggcttcccc atgcgccgct cgaagggctc actccaggtg tcgatagtct    13260
aggctccaag ttggacagcc ggcttcacca atttagcttt tgttgcctag cgtgtggtag    13320
ccggactaag gaccagacgg tgttctagag aaggtttttg tctggttgtt ggattccagt    13380
agcccatctc cttcgtcgtg cacttcctcc ttcgcttcca cgctccttc gcagatggtg    13440
taggcgtact cttgtgcttg ccttggtaaa ttcgctctca tgttcaatat ggacgaactc    13500
attgccacac gccgccatgt ttgaagggta agtccatgc tcaaccatct catcaccgtt    13560
gccaaggatg aaggccatat ggtgtggctc atcatcatca tccgcctcca tgactgaagg    13620
gaatatccca tgctcaacca tctcacttga ggtgcctccg aagatggagc ggtcacactt    13680
gcttgttgtt ggtgatcgac gtgatgtagt cgccggagcg tcagagcttg aaggagtatc    13740
acttatttgt aactcgagga agaaaatgt tgcttgatgt agcattgtgt ccattgttgg    13800
tgtagattct tcaaggaatg ttttcttgta ggctttatgc atcgttttct tgatgtcgtg    13860
gccattcctc ttcatgatgc gtttggagtg tgnaagcgct cttcttgttg atgatgttca    13920
cggtcaaggg tgtggccttg aatccatcg ttgcgaagaa ggttgtagct tgatgttgct    13980
cttgtacttt gaggtgtcaa tgccggtgtg atcctgaaga cttgtggtgg ttgagcacgt    14040
tttgaaagag ttgtgcgtca atcttggcgt cccaatggtc catctggcg tcaaagtttt    14100
tggtgtagnc ctagaccgga ggtgatgtgc ctttctctatt catattgaca ctcgancaaa    14160
gtgtgagtgg acnaagggaa agaacaatac caaagttacc tctttccgat gttggtgaag    14220
gatcaagcga tctcacacta tggaatatta agagagaaca ataccaaagt tacctcttc    14280
cgatacattc gtcaacacaa tacctttgtc gaggttggag gcaaccggcc ttgatttcgg    14340
ttgtggtgtc aaaggatgga gtggttgttg ttgttacgag aaccaaagcg gaagaacaac    14400
cacaaatcaa aaaaggggcg aagatgaca aatttcagca gattcggaag aggtcggaca    14460
gtcgagtgg tggcccctt ttcgactcga gcaaagtgtg agtggcaagg gaaagancaa    14520
taccaaagtt acctctttcc gatgttggtg aaggatcaag cgatctcaca ctatggaata    14580
ttaagagaga ncaataccaa agttacctct tcccgataca ttggtcaaca caatacctct    14640
gtcgaggtca gaggcaaccg gccttgcttt cggttgtggt gtcaaaggat ggagtggttg    14700
ttgttgttac gagaaccaaa gcggaagaac aaccacaaat cgaaaaaggg gcgaagatg    14760
aacaaatttc agcagattca agagaggtcg gacagtccga gttggtggcc ggacggggt    14820
tggctggaca gtccggttg gaagctgaca gttcgggtag gtcaactcgg ctgttcttca    14880
ggggaaattg gatcga                                                   14896

SEQ ID NO: 12         moltype = AA  length = 623
FEATURE               Location/Qualifiers
source                1..623
                      mol_type = protein
                      organism = Aegilops tauschii
SEQUENCE: 12
MAAPAFAVSA AGLARPSAPR SGGAERRGRG VELQSPSLLF GRNKGTRSPR AVGVGGSGWR    60
VVMRAGGPSG EVMIPDGGSG GTPPSIDGPV QFDSDDLKVP FIDDETSLQD GGEDSIWSSE   120
TNQVSEEIDA EDTSRMDKES STREKLRILP PPGNGQQIYE IDPTLRDFKY HLEYRYSLYR   180
RIRSDIDEHE GGMDVFSRGY EKFGFMRSAE GITYREWAPG ADSAALVGDF NNWDPNADHM   240
SKNDLGVWEI FLPNNADGSP PIPHGSRVKV RMDTPSGIKD SIPAWIKYSV QTPGDIPYNG   300
IYYDPPEEEK YVFKHPQPKR PKSLRIYETH VGMSSPEPKI DTYANFRDEV LPRIKRLGYN   360
AVQIMAIQEH SYYGSFGYHV TNFFAPSSRF GSPEDLKSLI DRAHELGLVV LMDVVHSHAS   420
NNTLDGLNGF DGTDTHYFHG GSRGHHWMWD SRVFNYGNKE VIRFLLSNAR WWLEEYKFDG   480
FRFDGATSMM YTHHGLQVTF TGSYHEYFGF ATDVDAVVYL MLMNDLIHGF YPEAVTIGED   540
VSGMPTFALP VQVGGVGFDY RLHMAVADKW IELLKGNDEA WEMGNIVHTL TNRRWLEKCV   600
TYAESHDQAL VGDKTIAFWL MDK                                          623
```

```
SEQ ID NO: 13            moltype = DNA   length = 23
FEATURE                  Location/Qualifiers
misc_feature             1..23
                         note = Synthetic Construct
source                   1..23
                         mol_type = other DNA
                         organism = synthetic construct
SEQUENCE: 13
acggctttga tcatctcctc cca                                                 23

SEQ ID NO: 14            moltype = DNA   length = 25
FEATURE                  Location/Qualifiers
misc_feature             1..25
                         note = Synthetic Construct
source                   1..25
                         mol_type = other DNA
                         organism = synthetic construct
SEQUENCE: 14
tttgtctctt tgatgttccc caaat                                               25

SEQ ID NO: 15            moltype = DNA   length = 31
FEATURE                  Location/Qualifiers
misc_feature             1..31
                         note = Synthetic Construct
source                   1..31
                         mol_type = other DNA
                         organism = synthetic construct
SEQUENCE: 15
tatgaccaga gtatgtctac agcttggcaa t                                        31

SEQ ID NO: 16            moltype = DNA   length = 27
FEATURE                  Location/Qualifiers
misc_feature             1..27
                         note = Synthetic Construct
source                   1..27
                         mol_type = other DNA
                         organism = synthetic construct
SEQUENCE: 16
tgcatcctaa gtgggaaacc ctaacca                                             27

SEQ ID NO: 17            moltype = DNA   length = 27
FEATURE                  Location/Qualifiers
misc_feature             1..27
                         note = Synthetic Construct
source                   1..27
                         mol_type = other DNA
                         organism = synthetic construct
SEQUENCE: 17
tcaatttgga tcagagggga tagtcca                                             27

SEQ ID NO: 18            moltype = DNA   length = 27
FEATURE                  Location/Qualifiers
misc_feature             1..27
                         note = Synthetic Construct
source                   1..27
                         mol_type = other DNA
                         organism = synthetic construct
SEQUENCE: 18
tgacaaggtt gcccatttct aatgcaa                                             27

SEQ ID NO: 19            moltype = DNA   length = 28
FEATURE                  Location/Qualifiers
misc_feature             1..28
                         note = Synthetic Construct
source                   1..28
                         mol_type = other DNA
                         organism = synthetic construct
SEQUENCE: 19
gatagctgga ttaggcgatc gcctcagg                                            28

SEQ ID NO: 20            moltype = DNA   length = 30
FEATURE                  Location/Qualifiers
misc_feature             1..30
                         note = Synthetic Construct
source                   1..30
                         mol_type = other DNA
                         organism = synthetic construct
SEQUENCE: 20
ttggtagagg aattagcaaa gtaaaatcca                                          30
```

```
SEQ ID NO: 21          moltype = DNA   length = 32
FEATURE                Location/Qualifiers
misc_feature           1..32
                       note = Synthetic Construct
source                 1..32
                       mol_type = other DNA
                       organism = synthetic construct
SEQUENCE: 21
ggtagaacct tttgcattat gtgtgctttt cc                                    32

SEQ ID NO: 22          moltype = DNA   length = 33
FEATURE                Location/Qualifiers
misc_feature           1..33
                       note = Synthetic Construct
source                 1..33
                       mol_type = other DNA
                       organism = synthetic construct
SEQUENCE: 22
gctacctcga aatgcaatgg aaatcttaga gac                                   33

SEQ ID NO: 23          moltype = DNA   length = 27
FEATURE                Location/Qualifiers
misc_feature           1..27
                       note = Synthetic Construct
source                 1..27
                       mol_type = other DNA
                       organism = synthetic construct
SEQUENCE: 23
ccaaggaggg agtgaggagc ttgactt                                          27

SEQ ID NO: 24          moltype = DNA   length = 27
FEATURE                Location/Qualifiers
misc_feature           1..27
                       note = Synthetic Construct
source                 1..27
                       mol_type = other DNA
                       organism = synthetic construct
SEQUENCE: 24
tgtcagcttg aatgcccttg cacttct                                          27

SEQ ID NO: 25          moltype = DNA   length = 23
FEATURE                Location/Qualifiers
misc_feature           1..23
                       note = Synthetic Construct
source                 1..23
                       mol_type = other DNA
                       organism = synthetic construct
SEQUENCE: 25
gatcgcgctt cctgaacctg tat                                              23

SEQ ID NO: 26          moltype = DNA   length = 25
FEATURE                Location/Qualifiers
misc_feature           1..25
                       note = Synthetic Construct
source                 1..25
                       mol_type = other DNA
                       organism = synthetic construct
SEQUENCE: 26
ctcagaccac gaagggatct gtatg                                            25

SEQ ID NO: 27          moltype = DNA   length = 27
FEATURE                Location/Qualifiers
misc_feature           1..27
                       note = Synthetic Construct
source                 1..27
                       mol_type = other DNA
                       organism = synthetic construct
SEQUENCE: 27
atgaatacgt gcaacactcc catctgc                                          27

SEQ ID NO: 28          moltype = DNA   length = 29
FEATURE                Location/Qualifiers
misc_feature           1..29
                       note = Synthetic construct
source                 1..29
                       mol_type = other DNA
                       organism = synthetic construct
SEQUENCE: 28
```

```
ggaagcaaag ttttgcactt gccaatatg                                         29

SEQ ID NO: 29          moltype = DNA   length = 28
FEATURE                Location/Qualifiers
misc_feature           1..28
                       note = Synthetic Construct
source                 1..28
                       mol_type = other DNA
                       organism = synthetic construct
SEQUENCE: 29
cgtctccagc aagccatttc ctaccttta                                         28

SEQ ID NO: 30          moltype = DNA   length = 28
FEATURE                Location/Qualifiers
misc_feature           1..28
                       note = Synthetic Construct
source                 1..28
                       mol_type = other DNA
                       organism = synthetic construct
SEQUENCE: 30
ttttgccact agtttttgcc aattttcc                                          28

SEQ ID NO: 31          moltype = DNA   length = 29
FEATURE                Location/Qualifiers
misc_feature           1..29
                       note = Synthetic Construct
source                 1..29
                       mol_type = other DNA
                       organism = synthetic construct
SEQUENCE: 31
tcaatcaatt tggatcagag ggaacatca                                         29

SEQ ID NO: 32          moltype = DNA   length = 36
FEATURE                Location/Qualifiers
misc_feature           1..36
                       note = Synthetic Construct
source                 1..36
                       mol_type = other DNA
                       organism = synthetic construct
SEQUENCE: 32
tagcagtgca ggaatttaag ttaaaccact attaca                                 36

SEQ ID NO: 33          moltype = DNA   length = 24
FEATURE                Location/Qualifiers
misc_feature           1..24
                       note = Synthetic Construct
source                 1..24
                       mol_type = other DNA
                       organism = synthetic construct
SEQUENCE: 33
ctcccattct cgtttattcg tagc                                              24

SEQ ID NO: 34          moltype = DNA   length = 26
FEATURE                Location/Qualifiers
misc_feature           1..26
                       note = Synthetic Construct
source                 1..26
                       mol_type = other DNA
                       organism = synthetic construct
SEQUENCE: 34
gttcggttac catgtcacct cagagc                                            26

SEQ ID NO: 35          moltype = DNA   length = 28
FEATURE                Location/Qualifiers
misc_feature           1..28
                       note = Synthetic Construct
source                 1..28
                       mol_type = other DNA
                       organism = synthetic construct
SEQUENCE: 35
gccaattgaa caacaatgcc acttcatt                                          28

SEQ ID NO: 36          moltype = DNA   length = 24
FEATURE                Location/Qualifiers
misc_feature           1..24
                       note = Synthetic Construct
source                 1..24
                       mol_type = other DNA
                       organism = synthetic construct
```

```
SEQUENCE: 36
gagtacccat tcgcacctag atgt                                              24

SEQ ID NO: 37           moltype = DNA   length = 27
FEATURE                 Location/Qualifiers
misc_feature            1..27
                        note = Synthetic Construct
source                  1..27
                        mol_type = other DNA
                        organism = synthetic construct
SEQUENCE: 37
gcctgttgca cgagcccatt aattact                                           27

SEQ ID NO: 38           moltype = DNA   length = 28
FEATURE                 Location/Qualifiers
misc_feature            1..28
                        note = Synthetic Construct
source                  1..28
                        mol_type = other DNA
                        organism = synthetic construct
SEQUENCE: 38
ttcgaacaaa tggacaccag cttttgat                                          28

SEQ ID NO: 39           moltype = DNA   length = 28
FEATURE                 Location/Qualifiers
misc_feature            1..28
                        note = Synthetic Construct
source                  1..28
                        mol_type = other DNA
                        organism = synthetic construct
SEQUENCE: 39
ttatatatca acttatgaat cctgaacg                                          28

SEQ ID NO: 40           moltype = DNA   length = 31
FEATURE                 Location/Qualifiers
misc_feature            1..31
                        note = Synthetic Construct
source                  1..31
                        mol_type = other DNA
                        organism = synthetic construct
SEQUENCE: 40
gtaaagtgtt cttttagcaa tttatacaaa c                                      31

SEQ ID NO: 41           moltype = DNA   length = 30
FEATURE                 Location/Qualifiers
misc_feature            1..30
                        note = Synthetic Construct
source                  1..30
                        mol_type = other DNA
                        organism = synthetic construct
SEQUENCE: 41
gcctcctcat ttcgctcgcg tgggtttaag                                        30

SEQ ID NO: 42           moltype = DNA   length = 36
FEATURE                 Location/Qualifiers
misc_feature            1..36
                        note = Synthetic Construct
source                  1..36
                        mol_type = other DNA
                        organism = synthetic construct
SEQUENCE: 42
agtgactatg aacttcaaga atttcgtgat acatca                                 36

SEQ ID NO: 43           moltype = DNA   length = 32
FEATURE                 Location/Qualifiers
misc_feature            1..32
                        note = Synthetic Construct
source                  1..32
                        mol_type = other DNA
                        organism = synthetic construct
SEQUENCE: 43
ctacaaaaaa ttgaacaacg atgccacttc at                                     32

SEQ ID NO: 44           moltype = DNA   length = 27
FEATURE                 Location/Qualifiers
misc_feature            1..27
                        note = Synthetic Construct
source                  1..27
                        mol_type = other DNA
```

-continued

```
                          organism = synthetic construct
SEQUENCE: 44
ccaactatat ttacagctca actctgg                                          27

SEQ ID NO: 45             moltype = DNA   length = 27
FEATURE                   Location/Qualifiers
misc_feature              1..27
                          note = Synthetic Construct
source                    1..27
                          mol_type = other DNA
                          organism = synthetic construct
SEQUENCE: 45
actgattttg ttcttgcaag acattca                                          27

SEQ ID NO: 46             moltype = DNA   length = 24
FEATURE                   Location/Qualifiers
misc_feature              1..24
                          note = Synthetic Construct
source                    1..24
                          mol_type = other DNA
                          organism = synthetic construct
SEQUENCE: 46
caaatggaca ccagcttttg atgc                                             24

SEQ ID NO: 47             moltype = DNA   length = 37
FEATURE                   Location/Qualifiers
misc_feature              1..37
                          note = Synthetic Construct
source                    1..37
                          mol_type = other DNA
                          organism = synthetic construct
SEQUENCE: 47
aaagttagct atatgcagtt taagttaatt tacaggt                               37

SEQ ID NO: 48             moltype = DNA   length = 30
FEATURE                   Location/Qualifiers
misc_feature              1..30
                          note = Synthetic Construct
source                    1..30
                          mol_type = other DNA
                          organism = synthetic construct
SEQUENCE: 48
tgtaagatgt tctttcagca atttatacta                                       30

SEQ ID NO: 49             moltype = DNA   length = 22
FEATURE                   Location/Qualifiers
misc_feature              1..22
                          note = Synthetic Construct
source                    1..22
                          mol_type = other DNA
                          organism = synthetic construct
SEQUENCE: 49
acgacgcgtg ccgattccgt at                                               22

SEQ ID NO: 50             moltype = DNA   length = 35
FEATURE                   Location/Qualifiers
misc_feature              1..35
                          note = Synthetic Construct
source                    1..35
                          mol_type = other DNA
                          organism = synthetic construct
SEQUENCE: 50
gccattcaca tcttatcaaa gactgtaaat tgttt                                 35

SEQ ID NO: 51             moltype = DNA   length = 34
FEATURE                   Location/Qualifiers
misc_feature              1..34
                          note = Synthetic Construct
source                    1..34
                          mol_type = other DNA
                          organism = synthetic construct
SEQUENCE: 51
atcctacaaa aaattgaaca acaatgccac tttc                                  34

SEQ ID NO: 52             moltype = DNA   length = 25
FEATURE                   Location/Qualifiers
misc_feature              1..25
                          note = Synthetic Construct
source                    1..25
```

```
                        mol_type = other DNA
                        organism = synthetic construct
SEQUENCE: 52
acatggagct acagttcaga tgtgc                                              25

SEQ ID NO: 53           moltype = DNA   length = 27
FEATURE                 Location/Qualifiers
misc_feature            1..27
                        note = Synthetic Construct
source                  1..27
                        mol_type = other DNA
                        organism = synthetic construct
SEQUENCE: 53
gcctgttgca cgagcccatt actagat                                            27

SEQ ID NO: 54           moltype = DNA   length = 34
FEATURE                 Location/Qualifiers
misc_feature            1..34
                        note = Synthetic Construct
source                  1..34
                        mol_type = other DNA
                        organism = synthetic construct
SEQUENCE: 54
ggcaattact tgtttctttg tgcaattact tgtt                                    34

SEQ ID NO: 55           moltype = DNA   length = 28
FEATURE                 Location/Qualifiers
misc_feature            1..28
                        note = Synthetic Construct
source                  1..28
                        mol_type = other DNA
                        organism = synthetic construct
SEQUENCE: 55
gttttgaatg ctcaagagaa gtactagt                                           28

SEQ ID NO: 56           moltype = DNA   length = 30
FEATURE                 Location/Qualifiers
misc_feature            1..30
                        note = Synthetic Construct
source                  1..30
                        mol_type = other DNA
                        organism = synthetic construct
SEQUENCE: 56
tgtaagatgt tctttcagca atttatacta                                         30

SEQ ID NO: 57           moltype = DNA   length = 28
FEATURE                 Location/Qualifiers
misc_feature            1..28
                        note = Synthetic Construct
source                  1..28
                        mol_type = other DNA
                        organism = synthetic construct
SEQUENCE: 57
ttatgtcttg gtccaaagcc ccttttg                                            28

SEQ ID NO: 58           moltype = DNA   length = 30
FEATURE                 Location/Qualifiers
misc_feature            1..30
                        note = Synthetic Construct
source                  1..30
                        mol_type = other DNA
                        organism = synthetic construct
SEQUENCE: 58
tccacgtcag gaacttagac atgcaactat                                         30
```

WHEAT WITH INCREASED RESISTANT STARCH LEVELS

CROSS-REFERENCE TO RELATED APPLICATIONS

This application is a continuation of U.S. patent application Ser. No. 17/147,281, filed Jan. 12, 2021, which is a continuation of U.S. patent application Ser. No. 15/914,994, filed Mar. 7, 2018, now U.S. Pat. No. 10,934,557 issued Mar. 2, 2021, which is a continuation of U.S. patent application Ser. No. 14/825,369, filed Aug. 13, 2015, now U.S. Pat. No. 10,563,217 issued Feb. 18, 2020, which is a continuation of U.S. patent application Ser. No. 13/633,588, filed Oct. 2, 2012, now U.S. Pat. No. 9,150,839, issued Oct. 6, 2015, which claims the benefit of U.S. Provisional Application No. 61/542,953, entitled "WHEAT WITH INCREASED RESISTANT STARCH LEVELS," filed Oct. 4, 2011; all of which are incorporated herein by reference.

STATEMENT REGARDING FEDERALLY SPONSORED RESEARCH OR DEVELOPMENT

This invention was made with government support under grant DK085811 awarded by National Institutes of Health. The government has certain rights in the invention.

SEQUENCE LISTING

The Sequence Listing is being submitted electronically in XML format and is hereby incorporated by reference in its entirety. Said XML copy, created on Apr. 7, 2023, is named 147411_000136_Seq_Listing.xml and is 152,771 bytes in size.

FIELD

This invention relates to human-induced non-transgenic mutations in one or more starch branching enzyme II (SBEII) genes. In one embodiment, the invention relates to human-induced non-transgenic mutations in one or more SBEII genes of wheat and wheat plants. In still another embodiment, human-induced non-transgenic mutations are in the SBEIIa and/or SBEIIb gene sequences, more particularly, combined mutations in SBEIIa and in both SBEIIa and SBEIIb.

This invention further relates to wheat plants having wheat seeds and wheat flour with increased levels of amylose and increased levels of resistant starch as a result of non-transgenic mutations in at least one of their SBEII genes. This invention also relates to a method that utilizes non-transgenic means to create wheat plants having mutations in at least one of their SBEII genes. In addition, this invention concerns wheat flour and wheat-based food products made from the seeds of these wheat plants having mutations in at least one of their SBEII genes.

BACKGROUND

An alarming number of adults and children in the United States are either overweight or obese. Healthier food choices, including foods that are high in resistant starch, can help people to better manage their blood sugar levels and their weight. Resistant starch is defined as starch that is not digested in the small intestine of healthy individuals but is fermented in the large intestine. Due to its slow digestion, resistant starch does not have the same caloric load as readily digestible starch, nor does it cause as rapid a rise in blood glucose levels after ingestion. Instead, resistant starch results in a more controlled glucose release over a longer period of time after digestion. This results in a decreased glycemic response, increased insulin sensitivity, and greater feelings of satiety. As a form of dietary fiber, resistant starch contributes to better colon health due to its fermentation by probiotic organisms in the lower gastrointestinal tract into short chain fatty acids, such as butyrate.

In the United States, the majority of dietary starch is consumed in the form of wheat based foods, such as bread, cereals, pastas, and tortillas, which contain very low levels of resistant starch. Cereal starches typically contain less slowly digested amylose (about 25% of total starch) and more highly branched, rapidly digested amylopectin (about 75% of total starch). The amount of amylose in starch positively correlates with the levels of dietary fiber and resistant starch. In corn and barley, loss-of-function mutations of SBEIIb, one of several enzymes in the starch synthesis pathway, have been identified. SBEIIb is the predominant isoform of SBEII expressed in the endosperm of these crops and its loss results in increased amylose and resistant starch levels. In contrast, both SBEIIa and SBEIIb are expressed in the wheat endosperm, but SBEIIa is the major isoform that is expressed in this crop. Though there has been great interest in finding mutations that increase amylose content (and therefore resistant starch content) in wheat, wheat lines with increased amylose levels are not commercially available. Preferred mutations would be single nucleotide polymorphisms (SNPs) that reduce or eliminate SBEII enzyme activity (and, in turn, increase amylose levels) without having significant negative pleiotropic effects.

Identification of SNPs in wheat SBEII genes has proceeded slowly because, among other possible reasons, there is limited genetic diversity in today's commercial wheat cultivars and bread wheat is a polyploid, with a complement of 7 chromosomes from each of three ancestors called the A, B and D genomes, resulting in a total of 21 chromosomes. Typically, the bread wheat genome has three functionally redundant copies of each gene (called homoeologs), and therefore, single gene alterations usually do not produce any readily visible phenotype such as those that have been found in diploid corn. Often in wheat, altered variants of all three homoeologs must be combined genetically in order to evaluate their effects. Pasta (durum) wheat is a tetraploid, consisting of A and B genomes, so only two altered copies of each homoeolog must be combined to obtain a phenotype.

To further compound these challenges, SBEIIa and SBEIIb are closely located on the same chromosome in wheat, making it difficult for alleles in these genes to be inherited independently unless through a rare recombination event. Thus, it would be useful to have knock-down or knock-out mutations, resulting from SNPs, of both SBEIIa and SBEIIb of each genome of wheat. The availability of multiple allelic mutations within each SBEII locus, particularly within each SBEII locus of the same genome, would allow for the breeding of new, non-genetically modified wheat lines with a spectrum of increased amylose and resistant starch levels in seeds. Seeds from these lines could be used to produce healthier wheat-based food products, including flour, bread, cereals, pastas, and tortillas.

SUMMARY

In one embodiment, the invention relates to non-transgenic mutations in one or more SBEII genes. In one embodiment, one or more mutations are in the SBEIIa gene. In another embodiment, one or more mutations are in the SBEIIb gene. In another embodiment, one or more mutations are in each of the SBEIIa and SBEIIb genes.

In one embodiment, the invention relates to multiple non-transgenic mutations in the SBEIIa gene including but not limited to 1, 2, 3, 4, 5, 6, 7, 8, 9, 10, and greater than 10 mutations.

In another embodiment, the invention relates to multiple non-transgenic mutations in the SBEIIb gene including but not limited to 1, 2, 3, 4, 5, 6, 7, 8, 9, 10, and greater than 10 mutations.

In another embodiment, the invention relates to multiple non-transgenic mutations in the SBEIIa gene including but not limited to 1, 2, 3, 4, 5, 6, 7, 8, 9, 10, and greater than 10 mutations and multiple mutations in the SBEIIb gene including but not limited to 1, 2, 3, 4, 5, 6, 7, 8, 9, 10, and greater than 10 mutations.

In another embodiment, this invention relates to a wheat plant, wheat seeds, wheat plant parts, and progeny thereof with increased amylose content and increased resistant starch levels compared to wild type wheat plant, wheat seeds, wheat plant parts, and progeny thereof.

In another embodiment, this invention relates to a wheat plant, wheat seeds, wheat plant parts, and progeny thereof having reduced activity of one or more SBEII enzymes compared to the wild type wheat plant, wherein the reduction in SBEII enzyme activity is caused by a human-induced non-transgenic mutation in one or more of the wheat plant's SBEII genes. In another embodiment, the SBEIIa enzyme has reduced activity. In yet another embodiment, the SBEIIb enzyme has reduced activity. In still another embodiment, the SBEIIa and SBEIIb enzymes have reduced activity.

In another embodiment, this invention includes a wheat plant containing one or more mutated SBEII genes, as well as seeds, pollen, plant parts and progeny of that plant.

In another embodiment, this invention includes food and food products incorporating wheat seeds and wheat flour having reduced SBEII enzyme activity caused by a human-induced non-transgenic mutation in one or more SBEII genes.

In another embodiment, this invention includes a wheat plant having reduced activity of one or more SBEII enzymes compared to the wild type wheat plants, created by the steps of obtaining plant material from a parent wheat plant, inducing at least one mutation in at least one copy of an SBEII gene of the plant material by treating the plant material with a mutagen to create mutagenized plant material (e.g., seeds or pollen), analyzing progeny wheat plants to detect at least one mutation in at least one copy of a SBEII gene, selecting progeny wheat plants that have at least one mutation in at least one copy of an SBEII gene, crossing progeny wheat plants that have at least one mutation in at least one copy of an SBEII gene with other progeny wheat plants that have at least one mutation in a different copy of an SBEII gene, and repeating the cycle of identifying progeny wheat plants having mutations and crossing the progeny wheat plants having mutations with other progeny wheat plants having mutations to produce progeny wheat plants with reduced SBEII enzyme activity. In another embodiment, the method comprises growing or using the mutagenized plant material to produce progeny wheat plants.

BRIEF DESCRIPTION OF THE SEQUENCE LISTING

SEQ ID NO: 1 shows a partial *Triticum aestivum* gene for starch branching enzyme IIa, A genome, exons 1-14.

SEQ ID NO: 2 shows the partial protein sequence encoded by SEQ ID NO: 1.

SEQ ID NO: 3 shows the *Triticum aestivum* SBEIIa gene for starch branching enzyme IIa, B genome, exons 1-22 (GenBank Accession FM865435).

SEQ ID NO: 4 shows the protein encoded by SEQ ID NO: 3 (GenBank Accession CAR95900).

SEQ ID NO: 5 shows the *Aegilops tauschii* gene for starch branching enzyme IIa, D genome, complete sequence exons 1-22 (GenBank Accession AF338431).

SEQ ID NO: 6 shows the protein encoded by SEQ ID NO: 5 (GenBank Accession AAK26821).

SEQ ID NO: 7 shows a partial *Triticum aestivum* gene for starch branching enzyme IIb, A genome, exons 1-11.

SEQ ID NO: 8 shows the partial protein encoded by SEQ ID NO: 7.

SEQ ID NO: 9 shows the partial *Triticum aestivum* gene for starch branching enzyme IIb, B genome, exons 1-11.

SEQ ID NO: 10 shows the partial protein encoded by SEQ ID NO: 9.

SEQ ID NO: 11 shows the partial *Aegilops tauschii* gene for starch branching enzyme IIb, D genome, exons 1-16 (GenBank Accession AY740398).

SEQ ID NO: 12 shows the partial protein encoded by SEQ ID NO: 11 (GenBank Accession AAW80632).

SEQ ID NOs: 13-58 show exemplary homoeolog specific primers that have proven useful in identifying useful mutations within the SBEIIa and SBEIIb gene sequences.

DETAILED DESCRIPTION

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "allele" is any of one or more alternative forms of a gene, all of which relate to one trait or characteristic. In a diploid cell or organism, the two alleles of a given gene occupy corresponding loci on a pair of homologous chromosomes.

As used herein, amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). Sequences may also be aligned using algorithms known in the art including but not limited to CLUSTAL V algorithm or the Blastn or BLAST 2 sequence programs.

"Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the Blosum62 substitution matrix (Hentikoff and Hentikoff, 1992, Proc. Natl. Acad. Sci. USA 89: 10915-10919).

By the statement "sequence A is n % similar to sequence B," it is meant that n % of the positions of an optimal global alignment between sequences A and B consists of identical residues or nucleotides and conservative substitutions. By the statement "sequence A is n identical to sequence B," it is meant that n % of the positions of an optimal global alignment between sequences A and B consists of identical residues or nucleotides.

As used herein, the term "plant" includes reference to an immature or mature whole plant, including a plant from which seed or grain or anthers have been removed. A seed or embryo that will produce the plant is also considered to be the plant.

As used herein, the term "plant parts" includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

As used herein, an "SBEII derivative" refers to a SBEII protein/peptide/polypeptide sequence that possesses biological activity that is substantially reduced as compared to the biological activity of the whole SBEII protein/peptide/polypeptide sequence. In other words, it refers to a polypeptide of a modified SBEII protein of the invention that has reduced SBEII enzymatic activity. The term "SBEII derivative" encompasses the "fragments" or "chemical derivatives" of a modified SBEII protein/peptide.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides," that due to mutagenesis are not 100% identical but nevertheless code for the same amino acid sequence.

A "reduced or non-functional fragment," as is used herein, refers to a nucleic acid sequence that encodes for a SBEII protein that has reduced biological activity as compared the protein coding of the whole nucleic acid sequence. In other words, it refers to a nucleic acid or fragment(s) thereof that substantially retains the capacity of encoding an SBEII polypeptide of the invention, but the encoded SBEII polypeptide has reduced activity.

The term "fragment," as used herein, refers to a polynucleotide sequence, (e.g., a PCR fragment) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the invention, the term "isolated polynucleotide" is sometimes used. This term, when applied to DNA, refers to a DNA molecule that is separated from sequences with which it is immediately contiguous (in the 5' and 3'directions) in the naturally occurring genome of the organism from which it was derived. For example, the "isolated polynucleotide" may comprise a PCR fragment. In another embodiment, the "isolated polynucleotide" may comprise a DNA molecule inserted into a vector, such as a plasmid or virus vector, or integrated into the genomic DNA of a prokaryote or eukaryote. An "isolated polynucleotide molecule" may also comprise a cDNA molecule.

In one embodiment, the invention relates to non-transgenic mutations in one or more SBEII genes. In another embodiment, the invention describes wheat plants exhibiting seeds with increased amylose content and increased resistant starch levels compared to wild type wheat seeds, without the inclusion of foreign nucleic acids in the wheat plants' genomes.

In still another embodiment, the invention relates to a series of independent human-induced non-transgenic mutations in one or more SBEII genes; wheat plants having one or more of these mutations in at least one SBEII gene thereof; and a method of creating and identifying similar and/or additional mutations in at least one SBEII gene of wheat. Additionally, the invention relates to wheat plants exhibiting seed with increased amylose and resistant starch content compared to wild type wheat seed, without the inclusion of foreign nucleic acids in the plants' genomes.

SBEII Mutations

A. SBEII Genes

In one embodiment, the invention relates to one or more non-transgenic mutations in the SBEII gene. In another embodiment, the SBEII gene may contain one or more non-transgenic mutations recited in Tables 1-6 and 8-12 and corresponding mutations in homoeologues and combinations thereof.

In another embodiment, the invention comprises corresponding mutations to the one or more non-transgenic mutations disclosed herein in the SBEII gene in a corresponding homoeologue. By way of example, an identified mutation in the SBEIIa gene of the A genome may be a beneficial mutation in the SBEIIa gene of the B and/or D genome. One of ordinary skill in the art will understand that the mutation in the homoeologue may not be in the exact location.

One of ordinary skill in the art understands there is natural variation in the genetic sequences of the SBEII genes in different wheat varieties. The degree of sequence identity between homologous SBEIIa genes or the proteins is believed to be about 90%. This is true for SBEIIb genes and proteins as well.

The inventors have determined that to achieve a high amylose phenotype in wheat plants, mutations that reduce SBEII gene function are desirable. Preferred mutations include missense and nonsense changes, including mutations that prematurely truncate the translation of one or more SBEII proteins from messenger RNA, such as those mutations that create a stop codon within the coding region of an SBEII messenger RNA. Such mutations include insertions, repeat sequences, splice junction mutations, modified open reading frames (ORFs) and point mutations.

1. SBEIIa Genes

In another embodiment, the invention relates to one or more mutations in the SBEIIa gene. In one embodiment, the invention relates to multiple non-transgenic mutations in the SBEIIa gene including but not limited to 1, 2, 3, 4, 5, 6, 7, 8, 9, 10, and greater than 10 mutations.

In still another embodiment, one or more mutations are in the SBEIIa gene of the A genome. In another embodiment, one or more mutations are in the SBEIIa gene of the B genome. In still another embodiment, one or more mutations are in the SBEIIa gene of the D genome. In yet another embodiment, one or more mutations are in the SBEIIa genes of the A and B genomes. In still another embodiment, one or more mutations are in the SBEIIa genes of the A and D genomes. In another embodiment, one or more mutations are in the SBEIIa genes of the B and D genomes. In yet another embodiment, one or more mutations are in the SBEIIa genes of the A, B, and D genomes.

In one embodiment, one or more non-transgenic mutations are in both alleles of the SBEIIa gene in the A genome. In another embodiment, the non-transgenic mutations are identical in both alleles of the SBEIIa gene of the A genome.

In one embodiment, one or more non-transgenic mutations are in both alleles of the SBEIIa gene in the B genome. In another embodiment, the non-transgenic mutations are identical in both alleles of the SBEIIa gene of the B genome.

In one embodiment, one or more non-transgenic mutations are in both alleles of the SBEIIa gene in the D genome. In another embodiment, the non-transgenic mutations are identical in both alleles of the SBEIIa gene of the D genome.

The following mutations are exemplary of the mutations created and identified according to various embodiments of the invention. SEQ ID NOs 1-6 are reference sequences for SBEIIa. SEQ ID NOs 7-12 are reference sequences for SBEIIb.

The following mutations identified in Tables 1-6 are exemplary of the mutations created and identified according to various embodiments of the invention. They are offered by way of illustration, not limitation. It is to be understood that the mutations below are merely exemplary and that similar mutations are also contemplated.

The nomenclature used in Tables 1-6 and 8-12 indicates the wild type nucleotide or amino acid, followed by its position according to the referenced sequence, followed by the changed nucleotide or amino acid (A.A.) at that position using standard genetic code terminology. An asterisk is used to designate a stop codon, also called a truncation mutation.

One exemplary mutation is G5267A, resulting in a change from guanine to adenine at nucleotide position 5267 identified according to its position in the sequence of SEQ ID NO: 1. This mutation results in a change from tryptophan to a stop mutation at amino acid position 436 identified according to its position in the expressed protein (SEQ ID NO: 2).

TABLE 1

Examples of mutations created and identified in SBEIIa in the A genome of wheat plants. Nucleotide and amino acid changes are identified according to their positions in SEQ ID NOs: 1 and 2, respectively.

| Variety | Primer SEQ IDs. | Nucleotide Mutation | A.A. Mutation | PSSM | SIFT |
|---|---|---|---|---|---|
| Express | 13, 14 | C538T | V51= | | |
| Express | 13, 14 | G586A | E67= | | |
| Express | 13, 14 | C605T | P74S | | 0.89 |
| Express | 13, 14 | G608A | A75T | | 0.67 |
| Express | 13, 14 | C644T | Intron | | |
| Express | 13, 14 | G648A | Intron | | |
| Express | 13, 14 | C853T | Intron | | |
| Express | 13, 14 | G951A | G97= | | |
| Express | 13, 14 | G952A | G98R | | 0.44 |
| Express | 13, 14 | G1036A | E126K | | 0.86 |
| Express | 13, 14 | G1059A | P133= | | |
| Express | 15, 16 | C2384T | Intron | | |
| Express | 15, 16 | C2384T | Intron | | |
| Express | 15, 16 | C2394T | Intron | | |
| Express | 15, 16 | G2574A | Intron | | |
| Express | 15, 16 | G2582A | Splice Junction | | |
| Express | 15, 16 | G2592A | D260N | 10.4 | 0.3 |
| Express | 15, 16 | G2605A | G264D | 22 | 0 |
| Express | 15, 16 | G2612A | K266= | | |
| Express | 15, 16 | G2625A | A271T | 10.8 | 0.04 |
| Express | 15, 16 | C2664T | P284S | 20.3 | 0.01 |
| Express | 15, 16 | G2674A | G287D | 19.4 | 0 |
| Express | 15, 16 | C2857T | Intron | | |
| Express | 15, 16 | C2861T | Intron | | |
| Express | 15, 16 | C2921T | Intron | | |
| Express | 15, 16 | G2990A | E296K | | 0.03 |
| Express | 15, 16 | C3004T | F300= | | |
| Express | 15, 16 | G3039A | R312K | 8.2 | 0.08 |
| Express | 15, 16 | A3155T | Intron | | |
| Express | 17, 18 | C5164T | Intron | | |
| Express | 17, 18 | C5164T | Intron | | |
| Express | 17, 18 | G5196A | G413S | 13.8 | 0 |
| Kronos | 17, 18 | G5239A | G427D | 6.6 | 0.09 |
| Kronos | 17, 18 | C5256T | H433Y | 22.3 | 0 |
| Express | 17, 18 | G5267A | W436* | | |
| Kronos | 17, 18 | G5267A | W436* | | |
| Express | 17, 18 | G5268A | D437N | 7.9 | 0.04 |
| Express | 17, 18 | G5268A | D437N | 7.9 | 0.04 |
| Kronos | 17, 18 | G5268A | D437N | 7.9 | 0.04 |
| Express | 17, 18 | G5289A | G444R | 19 | 0 |
| Kronos | 17, 18 | G5289A | G444R | 19 | 0 |
| Express | 17, 18 | G5298A | E447K | 8.9 | 0.02 |
| Express | 17, 18 | G5301A | Splice Junction | | |
| Express | 17, 18 | G5301A | Splice Junction | | |
| Express | 17, 18 | G5305A | Intron | | |
| Kronos | 17, 18 | G5308A | Intron | | |
| Express | 17, 18 | C5315T | Intron | | |
| Express | 17, 18 | C5315T | Intron | | |
| Express | 17, 18 | C5315T | Intron | | |
| Express | 17, 18 | C5324T | Intron | | |
| Kronos | 17, 18 | C5325T | Intron | | |
| Kronos | 17, 18 | G5332A | Intron | | |
| Express | 17, 18 | G5386A | Intron | | |
| Express | 17, 18 | C5405T | L453= | | |
| Express | 17, 18 | C5405T | L453= | | |
| Express | 17, 18 | G5418A | R457K | 18.3 | 0.01 |
| Express | 17, 18 | G5422A | W458* | | |

TABLE 1-continued

Examples of mutations created and identified in SBEIIa in the A genome of wheat plants. Nucleotide and amino acid changes are identified according to their positions in SEQ ID NOs: 1 and 2, respectively.

| Variety | Primer SEQ IDs. | Nucleotide Mutation | A.A. Mutation | PSSM | SIFT |
|---|---|---|---|---|---|
| Kronos | 17, 18 | G5429A | E461K | 17.1 | 0.01 |
| Kronos | 17, 18 | G5429A | E461K | 17.1 | 0.01 |
| Express | 17, 18 | G5432A | E462K | 17.6 | 0.01 |
| Express | 17, 18 | G5432A | E462K | 17.6 | 0.01 |
| Express | 17, 18 | G5448A | G467E | 27.1 | 0 |
| Express | 17, 18 | G5463A | G472E | 27.1 | 0 |
| Express | 17, 18 | G5463A | G472E | 27.1 | 0 |
| Express | 17, 18 | G5463A | G472E | 27.1 | 0 |
| Express | 17, 18 | G5464A | G472= | | |
| Express | 17, 18 | G5465A | V473M | 17.1 | 0 |
| Express | 17, 18 | C5470T | T474= | | |
| Kronos | 17, 18 | C5470T | T474= | | |
| Express | 17, 18 | C5484T | T479I | 10.3 | 0.4 |
| Kronos | 17, 18 | G5493A | G482E | 27.1 | 0 |
| Kronos | 17, 18 | G5522A | Intron | | |
| Express | 17, 18 | G5534A | Intron | | |
| Express | 17, 18 | G5655A | Intron | | |
| Express | 17, 18 | C5712T | T488I | 16.9 | 0 |
| Express | 17, 18 | C5712T | T488I | 16.9 | 0 |
| Express | 17, 18 | C5719T | N490= | | |
| Express | 17, 18 | G5736A | G496E | 22.1 | 0 |
| Express | 17, 18 | C5745T | T499I | 15.8 | 0.02 |
| Express | 17, 18 | G5753A | D502N | 17.1 | 0.01 |
| Express | 17, 18 | G5756A | A503T | 19.8 | 0 |
| Express | 17, 18 | C5757T | A503V | 19.2 | 0 |
| Express | 17, 18 | G5783A | D512N | 7.8 | 0.18 |
| Kronos | 17, 18 | C5801T | H518Y | −8.3 | 1 |
| Express | 17, 18 | C5804T | P519S | 26.7 | 0 |
| Express | 17, 18 | C5811T | A521V | 6.3 | 0.21 |
| Express | 17, 18 | C5811T | A521V | 6.3 | 0.21 |
| Express | 17, 18 | G5831A | Splice Junction | | |
| Express | 17, 18 | G5852A | Intron | | |
| Express | 17, 18 | C5921T | Intron | | |
| Express | 17, 18 | G5956A | Intron | | |
| Express | 17, 18 | G5956A | Intron | | |

In one embodiment, the invention relates to a polynucleotide of the SBEIIa gene in the A genome with one or more non-transgenic mutations listed in Table 1 and corresponding to SEQ ID NO: 1. In another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% identical to SEQ ID NO: 1. In yet another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% similar to SEQ ID NO: 1.

In still another embodiment, the polynucleotide with one or more non-transgenic mutation listed in Table 1 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 2. In still another embodiment, the polynucleotide with one or more non-transgenic mutation listed in Table 1 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 2.

Examples of mutations created and identified in SBEIIa in the B genome of wheat plants are provided in Table 2. Nucleotide and amino acid changes are identified according to their positions in SEQ ID NOs: 3 and 4, respectively.

TABLE 2

Representative mutations in the SBEIIa gene in the B genome

| Variety | Primer SEQ IDs. | Nucleotide Mutation | A.A. Mutation | PSSM | SIFT |
|---|---|---|---|---|---|
| Express | 23, 24 | C4792T | Intron | | |
| Express | 23, 24 | G4830A | Intron | | |
| Express | 23, 24 | C4878T | Intron | | |
| Kronos | 23, 24 | C4881T | Intron | | |
| Express | 23, 24 | C4937T | Intron | | |
| Express | 23, 24 | C4960T | T410I | 4.8 | 0.25 |
| Express | 23, 24 | C4960A | T410N | 13.9 | 0.02 |
| Express | 23, 24 | C4961T | T410= | | |
| Express | 23, 24 | G4978A | G416D | 14.5 | 0.73 |
| Express | 23, 24 | G4987A | G419D | 16.8 | 0.01 |
| Express | 23, 24 | G4987A | G419D | 16.8 | 0.01 |
| Express | 23, 24 | C4990T | T420I | 21.4 | 0 |
| Express | 23, 24 | C4998T | H423Y | 15.5 | 0.59 |
| Express | 23, 24 | C5006T | F425= | | |
| Kronos | 23, 24 | G5011A | G427D | −0.4 | 0.5 |
| Express | 23, 24 | C5017T | P429L | 14.1 | 0.11 |
| Express | 23, 24 | G5020A | R430H | 21.4 | 0 |
| Kronos | 23, 24 | G5020A | R430H | 21.4 | 0 |
| Kronos | 23, 24 | G5020A | R430H | 21.4 | 0 |
| Kronos | 23, 24 | G5020A | R430H | 21.4 | 0 |
| Kronos | 23, 24 | G5022A | G431S | 25.2 | 0 |
| Kronos | 23, 24 | C5025T | H432Y | −3.6 | 1 |
| Express | 23, 24 | G5032A | W434* | | |
| Kronos | 23, 24 | G5033A | W434* | | |
| Express | 23, 24 | G5036A | M435I | 15 | 0.03 |
| Express | 23, 24 | G5038A | W436* | | |
| Express | 23, 24 | G5038A | W436* | | |
| Kronos | 23, 24 | G5040A | D437N | 19.9 | 0.01 |
| Express | 23, 24 | G5040A | D437N | 19.9 | 0.01 |
| Express | 23, 24 | C5044T | S438F | 12.1 | 0.01 |
| Express | 23, 24 | G5062A | G444E | 17 | 0 |
| Kronos | 23, 24 | G5062A | G444E | 17 | 0 |
| Kronos | 23, 24 | G5062A | G444E | 17 | 0 |
| Kronos | 23, 24 | G5063A | G444= | | |
| Kronos | 23, 24 | G5065A | S445N | −4.7 | 1 |
| Express | 23, 24 | G5068A | W446* | | |
| Express | 23, 24 | G5069A | W446* | | |
| Express | 23, 24 | G5069A | W446* | | |
| Kronos | 23, 24 | G5069A | W446* | | |
| Express | 23, 24 | G5069A | W446* | | |
| Express | 23, 24 | G5069A | W446* | | |
| Express | 23, 24 | G5069A | W446* | | |
| Express | 23, 24 | G5070A | E447K | 9.3 | 0.02 |
| Express | 23, 24 | G5070A | E447K | 9.3 | 0.02 |
| Kronos | 23, 24 | G5073A | Splice Junction | | |
| Kronos | 23, 24 | G5080A | Intron | | |
| Express | 23, 24 | C5081T | Intron | | |
| Express | 23, 24 | G5083A | Intron | | |
| Kronos | 23, 24 | C5087T | Intron | | |
| Express | 23, 24 | C5090T | Intron | | |
| Kronos | 23, 24 | C5090T | Intron | | |
| Kronos | 23, 24 | C5090T | Intron | | |
| Express | 23, 24 | C5090T | Intron | | |
| Express | 23, 24 | G5092A | Intron | | |
| Kronos | 23, 24 | G5105A | Intron | | |
| Express | 23, 24 | G5112A | Intron | | |
| Kronos | 23, 24 | G5112A | Intron | | |
| Kronos | 23, 24 | C5129T | Intron | | |
| Kronos | 23, 24 | C5129T | Intron | | |
| Express | 23, 24 | C5158T | Intron | | |
| Express | 23, 24 | G5160A | Splice Junction | | |
| Express | 23, 24 | G5161A | V448I | | 0.01 |
| Express | 23, 24 | G5161A | V448I | | 0.01 |
| Express | 23, 24 | G5161A | V448I | | 0.01 |
| Express | 23, 24 | G5168A | R450K | 19 | 0.01 |
| Express | 23, 24 | G5168A | R450K | 19 | 0.01 |
| Kronos | 23, 24 | G5168A | R450K | 19 | 0.01 |
| Express | 23, 24 | C5172T | F451= | | |
| Express | 23, 24 | G5185A | A456T | 13.3 | 0.11 |
| Express | 23, 24 | G5185A | A456T | 13.3 | 0.11 |
| Kronos | 23, 24 | G5189A | R457K | 19 | 0.01 |
| Express | 23, 24 | G5193A | W458* | | |
| Express | 23, 24 | C5197T | L460F | 11.7 | 0.02 |

TABLE 2-continued

Representative mutations in the SBEIIa gene in the B genome

| Variety | Primer SEQ IDs. | Nucleotide Mutation | A.A. Mutation | PSSM | SIFT |
|---|---|---|---|---|---|
| Express | 23, 24 | G5200A | E461K | 18.3 | 0.01 |
| Kronos | 23, 24 | G5203A | E462K | 18.3 | 0 |
| Kronos | 23, 24 | G5203A | E462K | 18.3 | 0 |
| Kronos | 23, 24 | G5211A | K464= | | |
| Kronos | 23, 24 | G5211A | K464= | | |
| Express | 23, 24 | G5219A | G467E | 27.7 | 0 |
| Kronos | 23, 24 | G5219A | G467E | 27.7 | 0 |
| Kronos | 23, 24 | G5219A | G467E | 27.7 | 0 |
| Kronos | 23, 24 | G5219A | G467E | 27.7 | 0 |
| Kronos | 23, 24 | T5223C | F468= | | |
| Express | 23, 24 | C5224T | R469* | | |
| Kronos | 23, 24 | G5233A | G472R | 27.3 | 0 |
| Kronos | 23, 24 | G5234A | G472E | 27.7 | 0 |
| Kronos | 23, 24 | G5234A | G472E | 27.7 | 0 |
| Express | 23, 24 | G5234A | G472E | 27.7 | 0 |
| Kronos | 23, 24 | C5240T | T474I | 21.9 | 0 |
| Kronos | 23, 24 | C5244T | S475= | | |
| Express | 23, 24 | C5255T | T479I | 9.8 | 0.55 |
| Express | 23, 24 | G5264A | G482E | 27.7 | 0 |
| Express | 23, 24 | G5272A | Splice Junction | | |
| Express | 23, 24 | G5272A | Splice Junction | | |
| Kronos | 23, 24 | G5272A | Splice Junction | | |
| Kronos | 23, 24 | G5276A | Intron | | |
| Express | 23, 24 | G5284A | Intron | | |
| Express | 23, 24 | G5286A | Intron | | |
| Express | 23, 24 | G5287A | Intron | | |
| Kronos | 23, 24 | G5287A | Intron | | |
| Kronos | 23, 24 | C5297T | Intron | | |
| Kronos | 23, 24 | C5297T | Intron | | |
| Kronos | 23, 24 | G5306A | Intron | | |
| Express | 23, 24 | C5330T | Intron | | |
| Express | 23, 24 | G5338A | Intron | | |
| Express | 23, 24 | G5350A | Intron | | |
| Express | 23, 24 | G5350A | Intron | | |
| Express | 23, 24 | C5353T | Intron | | |
| Express | 23, 24 | G5364A | Intron | | |
| Express | 23, 24 | G5364A | Intron | | |
| Express | 23, 24 | G5372A | Intron | | |
| Express | 23, 24 | G5372A | Intron | | |
| Express | 23, 24 | C5379T | Intron | | |
| Express | 23, 24 | C5395T | Intron | | |
| Express | 23, 24 | G5409A | Intron | | |
| Express | 23, 24 | G5421A | Intron | | |
| Express | 23, 24 | C5448T | Intron | | |
| Express | 23, 24 | T5450C | Intron | | |
| Kronos | 23, 24 | C5469T | Intron | | |
| Express | 23, 24 | G5472A | Splice Junction | | |
| Express | 23, 24 | G5475A | M485I | | 0.18 |
| Express | 23, 24 | G5495A | G492D | −0.8 | 0.39 |
| Express | 23, 24 | T5522A | V501D | 8.3 | 0.08 |
| Express | 23, 24 | C5528A | A503E | 19.9 | 0 |
| Express | 23, 24 | G5530A | V504M | 7.8 | 0.04 |
| Express | 23, 24 | C5553T | N511= | | |
| Express | 23, 24 | G5566A | G516R | 5.2 | 0.32 |
| Express | 23, 24 | C5575T | P519S | 17.4 | 0.02 |
| Kronos | 23, 24 | C5582T | A521V | 4.8 | 0.33 |
| Kronos | 23, 24 | C5582T | A521V | 4.8 | 0.33 |
| Express | 23, 24 | C5589T | S523= | | |
| Express | 23, 24 | G5606A | Intron | | |
| Express | 23, 24 | G5646A | Intron | | |
| Express | 23, 24 | C5662T | Intron | | |
| Express | 23, 24 | C5662T | Intron | | |
| Express | 23, 24 | G5675A | Intron | | |
| Express | 23, 24 | G5675A | Intron | | |
| Express | 23, 24 | G5835A | Intron | | |
| Express | 23, 24 | C4960T | T410I | 4.8 | 0.25 |
| Express | 23, 24 | G4987A | G419D | 16.8 | 0.01 |
| Express | 23, 24 | G5185A | A456T | 13.3 | 0.11 |
| Express | 23, 24 | C5243T | S475F | 26.4 | 0 |
| Express | 23, 24 | C5255T | T479I | 9.8 | 0.55 |
| Express | 21, 22 | G2386A | G233D | | 0 |
| Express | 21, 22 | G2456A | K256= | | |
| Express | 21, 22 | G2464A | Intron | | |
| Express | 21, 22 | G2483A | Intron | | |
| Express | 21, 22 | C2509T | Intron | | |
| Express | 21, 22 | C2518T | Intron | | |
| Express | 21, 22 | G2606A | A279T | 3.1 | 0.14 |
| Express | 21, 22 | C2610T | P280L | 5.1 | 0.47 |
| Express | 21, 22 | G2613A | G281D | 2.7 | 0.36 |
| Express | 21, 22 | G2613A | G281D | 2.7 | 0.36 |
| Express | 21, 22 | C2648T | P293S | | 0.08 |
| Express | 21, 22 | G2661A | Intron | | |
| Express | 21, 22 | G2661A | Intron | | |
| Express | 21, 22 | G2689A | Intron | | |
| Express | 21, 22 | G2945A | Splice Junction | | |
| Express | 21, 22 | C2967T | P303S | 8.4 | 0.17 |
| Express | 21, 22 | C2967T | P303S | 8.4 | 0.17 |
| Express | 21, 22 | G2456A | K256= | | |
| Express | 21, 22 | C2518T | Intron | | |
| Express | 21, 22 | G2606A | A279T | 3.1 | 0.14 |
| Express | 21, 22 | G2606A | A279T | 3.1 | 0.14 |
| Express | 21, 22 | C2648T | P293S | | 0.08 |
| Express | 21, 22 | G2661A | Intron | | |
| Express | 21, 22 | C2967T | P303S | 8.4 | 0.17 |

In one embodiment, the invention relates to a polynucleotide of the SBEIIa gene in the B genome with one or more non-transgenic mutations listed in Table 2 and corresponding to SEQ ID NO: 3. In another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical to SEQ ID NO: 3. In yet another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% similar to SEQ ID NO: 3.

In still another embodiment, the polynucleotide with one or more non-transgenic mutation listed in Table 2 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 4. In still another embodiment, the polynucleotide with one or more non-transgenic mutations listed in Table 2 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 4.

Examples of mutations created and identified in SBEIIa in the D genome of wheat plants are provided in Table 3. Nucleotide and amino acid changes are identified according to their positions in SEQ ID NOs: 5 and 6, respectively.

TABLE 3

Representative mutations in SBEIIa gene in the D genome

| Variety | Primer SEQ IDs. | Nucleotide Mutation | A.A. Mutation | PSSM | SIFT |
|---|---|---|---|---|---|
| Express | 25, 26 | C1708T | P60S | 13.4 | 0.03 |
| Express | 25, 26 | G1721A | S64N | −16.8 | 0.76 |
| Express | 25, 26 | G1753A | E75K | | 0.74 |
| Express | 25, 26 | G1753A | E75K | | 0.74 |
| Express | 25, 26 | G1761A | Q77= | | |

TABLE 3-continued

Representative mutations in SBEIIa gene in the D genome

| Variety | Primer SEQ IDs. | Nucleotide Mutation | A.A. Mutation | PSSM | SIFT |
|---|---|---|---|---|---|
| Express | 25, 26 | G1761A | Q77= | | |
| Express | 25, 26 | G1762A | Splice Junction | | |
| Express | 25, 26 | G1762A | Splice Junction | | |
| Express | 25, 26 | G1780A | Intron | | |
| Express | 25, 26 | G1962A | Intron | | |
| Express | 25, 26 | G2037A | Splice Junction | | |
| Express | 25, 26 | G1962A | Intron | | |
| Express | 25, 26 | G2037A | Splice Junction | | |
| Express | 25, 26 | C1999T | Intron | | |
| Express | 25, 26 | G2185A | E127K | | 0.79 |
| Express | 25, 26 | C1999T | Intron | | |
| Express | 25, 26 | C2011T | Intron | | |
| Express | 25, 26 | C2028T | Intron | | |
| Express | 25, 26 | C2028T | Intron | | |
| Express | 25, 26 | C2032T | Intron | | |
| Express | 25, 26 | G2065A | A87T | | 0.59 |
| Express | 25, 26 | G2065A | A87T | | 0.59 |
| Express | 25, 26 | G2065A | A87T | | 0.59 |
| Express | 25, 26 | G2079A | M91I | | 0.76 |
| Express | 25, 26 | G2086A | G94R | | 0.15 |
| Express | 25, 26 | G2087A | G94E | | 0.43 |
| Express | 25, 26 | G2126A | G107D | | 0.53 |
| Express | 25, 26 | G2131A | V109M | | 0.14 |
| Express | 25, 26 | G2134A | E110K | | 0.64 |
| Express | 25, 26 | G2149A | G115S | | 0.37 |
| Express | 25, 26 | G2149A | G115S | | 0.37 |
| Express | 25, 26 | G2183A | G126E | | 1 |
| Express | 25, 26 | G2187A | E127= | | |
| Express | 25, 26 | G2220A | G138= | | |
| Express | 25, 26 | C2266T | H154Y | 16.9 | 0.03 |
| Express | 25, 26 | C2286T | Intron | | |
| Express | 25, 26 | C2303T | Intron | | |
| Express | 27, 28 | C3589T | S242= | | |
| Express | 27, 28 | C3602T | H247Y | 23.2 | 0 |
| Express | 27, 28 | C3607A | G248= | | |
| Express | 27, 28 | C3611G | R250G | 16 | 0.01 |
| Express | 27, 28 | G3649A | Intron | | |
| Express | 27, 28 | G3677A | Intron | | |
| Express | 27, 28 | G3677A | Intron | | |
| Express | 27, 28 | C3743T | S266F | 16.9 | 0 |
| Express | 27, 28 | C3753T | I269= | | |
| Express | 27, 28 | C3772T | P276S | 9.5 | 0.35 |
| Express | 27, 28 | G3793A | G283S | 10.9 | 0.08 |
| Express | 27, 28 | G3794A | G283D | 16.3 | 0.01 |
| Express | 27, 28 | G3824A | Intron | | |
| Express | 27, 28 | G4083A | Intron | | |
| Express | 27, 28 | C4119T | F296= | | |
| Express | 27, 28 | C4126T | P299S | 9 | 0.15 |
| Express | 27, 28 | C4127T | P299L | 18.1 | 0.01 |
| Express | 29, 30 | G4818A | E320K | 7.9 | 0.11 |
| Express | 29, 30 | G4839A | A327T | 9.2 | 0.24 |
| Express | 29, 30 | G4850A | R330= | | |
| Express | 29, 30 | G4850A | R330= | | |
| Express | 29, 30 | G4851A | D331N | 13 | 0.02 |
| Express | 29, 30 | G4939A | G360E | 24.5 | 0 |
| Express | 29, 30 | C5118T | Y361= | | |
| Express | 29, 30 | G5144A | S370N | 22.9 | 0 |
| Express | 29, 30 | G5156A | G374E | 24.5 | 0 |
| Express | 29, 30 | G5156A | G374E | 24.5 | 0 |
| Express | 29, 30 | G5166A | E377= | | |
| Express | 29, 30 | C5169T | D378= | | |
| Express | 29, 30 | G5204A | G390D | 22.8 | 0 |
| Express | 29, 30 | G5258A | Intron | | |
| Express | 29, 30 | C5267T | Intron | | |
| Express | 29, 30 | C5275T | Intron | | |
| Express | 29, 30 | G5299A | Intron | | |
| Express | 31, 32 | G6793A | A499T | 18.7 | 0 |
| Express | 31, 32 | C6163T | Intron | | |
| Express | 31, 32 | G6793A | A499T | 18.7 | 0 |
| Express | 31, 32 | C6163T | Intron | | |
| Express | 31, 32 | G6793A | A499T | 18.7 | 0 |
| Express | 31, 32 | C6163T | Intron | | |
| Express | 31, 32 | G6174A | Intron | | |
| Express | 31, 32 | C6183T | Intron | | |
| Express | 31, 32 | C6227T | T406= | | |
| Express | 31, 32 | G6258A | D417N | 6.8 | 0.15 |
| Express | 31, 32 | G6258A | D417N | 6.8 | 0.15 |
| Express | 31, 32 | C6275T | H422= | | |
| Express | 31, 32 | G6277A | G423D | 0.6 | 0.45 |
| Express | 31, 32 | G6277A | G423D | 0.6 | 0.45 |
| Express | 31, 32 | G6286A | R426H | 21.5 | 0 |
| Express | 31, 32 | G6286A | R426H | 21.5 | 0 |
| Express | 31, 32 | G6305A | W432* | | |
| Express | 31, 32 | G6306A | D433N | 20.1 | 0.01 |
| Express | 31, 32 | G6306A | D433N | 20.1 | 0.01 |
| Express | 31, 32 | C6320T | F437= | | |
| Express | 31, 32 | G6327A | G440R | 17.2 | 0 |
| Express | 31, 32 | G6328A | G440E | 17.3 | 0 |
| Express | 31, 32 | G6329A | G440= | | |
| Express | 31, 32 | G6335A | W442* | | |
| Express | 31, 32 | G6336A | E443K | 9.4 | 0.02 |
| Express | 31, 32 | C6418T | Intron | | |
| Express | 31, 32 | G6426A | Splice Junction | | |
| Express | 31, 32 | C6442T | L449= | | |
| Express | 31, 32 | C6442T | L449= | | |
| Express | 31, 32 | G6451A | A452T | 13.2 | 0.08 |
| Express | 31, 32 | G6459A | W454* | | |
| Express | 31, 32 | C6463T | L456F | 11.6 | 0.02 |
| Express | 31, 32 | C6496A | D467N | 23.2 | 0 |
| Express | 31, 32 | C6525T | H476= | | |
| Express | 31, 32 | C6526T | H477Y | 21.5 | 0 |
| Express | 31, 32 | G6538A | Splice Junction | | |
| Express | 31, 32 | G6761A | G488D | −0.9 | 0.32 |
| Express | 31, 32 | G6761A | G488D | −0.9 | 0.32 |
| Express | 31, 32 | G6793A | A499T | 18.7 | 0 |
| Express | 31, 32 | G6796A | V500I | 5.8 | 0.15 |
| Express | 31, 32 | C6844A | D516N | 1.2 | 0.42 |
| Express | 31, 32 | C6854T | S519F | 11.1 | 0 |
| Express | 31, 32 | G6860A | G521D | 15.5 | 0 |
| Express | 31, 32 | G6860A | G521D | 15.5 | 0 |
| Express | 31, 32 | G6862A | E522K | 20.2 | 0 |
| Express | 31, 32 | G6881A | Intron | | |
| Express | 31, 32 | C6898T | Intron | | |

In one embodiment, the invention relates to a polynucleotide of the SBEIIa gene of the D genome with one or more non-transgenic mutations listed in Table 3 and corresponding to SEQ ID NO: 5. In another embodiment, the polynucleotide with one or more non-transgenic mutations listed in Table 3 is 85%, 86%, 87%, 88%, 89%, 90%, 91%, 92%, 93%, 94%, 95%, 96%, 97%, 98%, 99% or greater than 99% identical to SEQ ID NO: 5. In yet another embodiment, the polynucleotide with one or more non-transgenic mutations listed in Table 3 is 85%, 86%, 87%, 88%, 89%, 90%, 91%, 92%, 93%, 94%, 95%, 96%, 97%, 98%, 99% or greater than 99% similar to SEQ ID NO: 5.

In still another embodiment, the polynucleotide with one or more non-transgenic mutation listed in Table 3 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 6. In still another embodiment, the polynucleotide with one or more non-transgenic mutation listed in Table 3 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 6.

2. SBEIIb Genes

In another embodiment, one or more non-transgenic mutations are in the SBEIIb gene. In one embodiment, the invention relates to multiple non-transgenic mutations in the SBEIIb gene including but not limited to 1, 2, 3, 4, 5, 6, 7, 8, 9, 10, and greater than 10 mutations.

In still another embodiment, one or more mutations are in the SBEIIb gene of the A genome. In another embodiment, one or more mutations are in the SBEIIb gene of the B genome. In still another embodiment, one or more mutations are in the SBEIIb gene of the D genome. In yet another embodiment, one or more mutations are in the SBEIIb genes of the A and B genomes. In still another embodiment, one or more mutations are in the SBEIIb genes of the A and D genomes. In another embodiment, one or more mutations are in the SBEIIb genes of the B and D genomes. In yet another embodiment, one or more mutations are in the SBEIIb genes of the A, B, and D genomes.

In one embodiment, one or more non-transgenic mutations are in both alleles of the SBEIIb gene in the A genome. In another embodiment, the non-transgenic mutations are identical in both alleles of the SBEIIb gene of the A genome.

In one embodiment, one or more non-transgenic mutations are in both alleles of the SBEIIb gene in the B genome. In another embodiment, the non-transgenic mutations are identical in both alleles of the SBEIIb gene of the B genome.

In one embodiment, one or more non-transgenic mutations are in both alleles of the SBEIIb gene in the D genome. In another embodiment, the non-transgenic mutations are identical in both alleles of the SBEIIb gene of the D genome.

Examples of mutations created and identified in SBEIIb in the A genome of wheat plants are provided in Table 4. Nucleotide and amino acid changes are identified according to their positions in SEQ ID NOs: 7 and 8, respectively.

TABLE 4

Representative Mutations in SBEIIb in the A genome

| Variety | Primer SEQ IDs. | Nucleotide Mutation | A.A. Mutation | PSSM | SIFT |
|---|---|---|---|---|---|
| Express | 33, 34 | G211A | Intron | | |
| Express | 33, 34 | G278A | W59* | | |
| Express | 33, 34 | G298A | G66D | 6.1 | 0.03 |
| Express | 33, 34 | G310A | G70E | 2.1 | 0.83 |
| Express | 33, 34 | G310A | G70E | 2.1 | 0.83 |
| Express | 33, 34 | C437T | Intron | | |
| Express | 33, 34 | G485A | Intron | | |
| Express | 33, 34 | G547A | V99I | | 0.84 |
| Express | 33, 34 | G565A | E105K | | 0.11 |
| Express | 33, 34 | G678A | T142= | | |
| Express | 33, 34 | G680A | G143E | | 1 |
| Express | 33, 34 | G709A | G153R | 8.6 | 0.03 |
| Express | 33, 34 | C739T | P163S | 10.2 | 0.09 |
| Express | 33, 34 | C743T | T164M | -3.4 | 0.21 |
| Express | 33, 34 | G769A | E173K | -4.1 | 0.56 |
| Express | 35, 36 | G1237A | E201K | 16.7 | 0.21 |
| Express | 35, 36 | C1307T | Intron | | |
| Express | 35, 36 | C1319T | Intron | | |
| Express | 35, 36 | C1322T | Intron | | |
| Express | 35, 36 | G1341A | G211S | 14.9 | 0.02 |
| Express | 35, 36 | G1356A | E216K | 22.3 | 0 |
| Express | 35, 36 | C1857T | Intron | | |
| Express | 37, 38 | C2021T | Intron | | |
| Express | 37, 38 | C2021T | Intron | | |
| Express | 35, 36 | G2031A | Intron | | |
| Express | 37, 38 | C2072T | Intron | | |
| Express | 37, 38 | C2124T | S259L | | 0.03 |
| Express | 37, 38 | C2126T | P260S | | 0.23 |
| Express | 37, 38 | G2142A | G265D | 3.6 | 0.17 |
| Express | 37, 38 | G2142A | G265D | 3.6 | 0.17 |
| Express | 37, 38 | G2142A | G265D | 3.6 | 0.17 |

TABLE 4-continued

Representative Mutations in SBEIIb in the A genome

| Variety | Primer SEQ IDs. | Nucleotide Mutation | A.A. Mutation | PSSM | SIFT |
|---|---|---|---|---|---|
| Express | 37, 38 | G2156A | Splice Junction | | |
| Express | 37, 38 | C2169T | Intron | | |
| Express | 37, 38 | C2174T | Intron | | |
| Express | 37, 38 | G2244A | G273S | 0.6 | 0.31 |
| Express | 37, 38 | G2245A | G273D | -9.5 | 1 |
| Express | 37, 38 | C2250T | P275S | 11.4 | 0.13 |
| Express | 37, 38 | G2282A | W285* | | |
| Express | 37, 38 | G2282A | W285* | | |
| Express | 37, 38 | G2282A | W285* | | |
| Express | 37, 38 | C2293T | S289F | 8.4 | 0.02 |
| Express | 37, 38 | C2340T | P305S | 15.8 | 0 |
| Express | 37, 38 | C2344T | P306L | 17.3 | 0 |
| Express | 37, 38 | C2344T | P306L | 17.3 | 0 |
| Express | 37, 38 | G2349A | E308K | | 0.07 |
| Express | 37, 38 | A2441T | Intron | | |
| Express | 37, 38 | C2484T | Intron | | |
| Express | 37, 38 | G2525A | Intron | | |
| Express | 37, 38 | G2535A | E309K | | 0.03 |
| Express | 37, 38 | G2540A | K310= | | |
| Express | 37, 38 | C2556T | P316S | 11.5 | 0.07 |
| Express | 37, 38 | C2606T | G332= | | |
| Express | 37, 38 | C2606T | G332= | | |
| Express | 37, 38 | C2617T | P336L | 18.2 | 0.01 |
| Express | 37, 38 | C2642T | Intron | | |
| Express | 37, 38 | G2697A | Intron | | |

In one embodiment, the invention relates to a polynucleotide of the SBEIIb gene of the A genome with one or more non-transgenic mutations listed in Table 4 and corresponding to SEQ ID NO: 7. In another embodiment, the polynucleotide with one or more non-transgenic mutations listed in Table 4 is 85%, 86%, 87%, 88%, 89%, 90%, 91%, 92%, 93%, 94%, 95%, 96%, 97%, 98%, 99% or greater than 99% identical to SEQ ID NO: 7. In yet another embodiment, the polynucleotide with one or more non-transgenic mutations listed in Table 4 is 85%, 86%, 87%, 88%, 89%, 90%, 91%, 92%, 93%, 94%, 95%, 96%, 97%, 98%, 99% or greater than 99% similar to SEQ ID NO: 7.

In still another embodiment, the polynucleotide with one or more non-transgenic mutation listed in Table 4 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 8. In still another embodiment, the polynucleotide with one or more non-transgenic mutation listed in Table 4 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 8.

Examples of mutations created and identified in SBEIIb in the B genome of wheat plants are provided in Table 5. Nucleotide and amino acid changes are identified according to their positions in SEQ ID NOs: 9 and 10, respectively.

TABLE 5

Representative mutations in the SBEIIb gene in the B genome

| Variety | Primer SEQ IDs. | Nucleotide Mutation | A.A. Mutation | PSSM | SIFT |
|---|---|---|---|---|---|
| Express | 41, 42 | G371A | G58R | | 0.26 |
| Express | 41, 42 | C422T | P75S | 20.4 | 0.02 |
| Express | 41, 42 | G435A | S79N | | 0.31 |

TABLE 5-continued

Representative mutations in the SBEIIb gene in the B genome

| Variety | Primer SEQ IDs. | Nucleotide Mutation | A.A. Mutation | PSSM | SIFT |
|---|---|---|---|---|---|
| Express | 41, 42 | C1033T | Intron | | |
| Express | 41, 42 | C1102T | Intron | | |
| Express | 41, 42 | C1102T | Intron | | |
| Express | 41, 42 | G1209A | D129N | 0.48 | |
| Express | 41, 42 | C1246T | S141F | | 0.07 |
| Express | 41, 42 | G1254A | E144K | | 0.91 |
| Express | 43, 44 | G1916A | S208N | | |
| Express | 43, 44 | C2196T | Intron | | |
| Express | 43, 44 | C2206T | Intron | | |
| Express | 43, 44 | G2221A | A225T | 6.9 | 0.21 |
| Express | 45, 46 | C2669T | Intron | | |
| Express | 45, 46 | C2776T | P260S | 10.4 | 0.21 |
| Express | 45, 46 | C2786T | P263L | 25.5 | 0.00 |
| Express | 45, 46 | C2786T | P263L | 25.5 | 0.00 |
| Express | 45, 46 | C2919T | S281L | 9.9 | 0.09 |
| Express | 45, 46 | C2786T | P263L | 25.5 | 0.00 |
| Express | 45, 46 | G3216A | K319= | | |
| Express | 45, 46 | C3232T | R325W | 27.3 | 0.00 |
| Express | 45, 46 | G3260A | S334N | 21.8 | 0.00 |
| Express | 47, 48 | C3478T | Intron | | |
| Express | 47, 48 | G3519A | Intron | | |
| Express | 47, 48 | G3678A | Intron | | |
| Express | 47, 48 | G3814A | Intron | | |
| Express | 47, 48 | C3884T | Intron | | |
| Express | 47, 48 | C3993T | L357F | 8.5 | 0.11 |
| Express | 47, 48 | G4087A | Intron | | |
| Express | 47, 48 | C4419T | Intron | | |
| Express | 47, 48 | G4280A | Intron | | |
| Express | 47, 48 | C4298T | Intron | | |
| Express | 47, 48 | C4374T | Intron | | |
| Express | 47, 48 | C4374T | Intron | | |
| Express | 47, 48 | C4422T | Intron | | |
| Express | 47, 48 | C4489T | Intron | | |

In one embodiment, the invention relates to a polynucleotide of the SBEIIb gene of the B genome with one or more non-transgenic mutations listed in Table 5 and corresponding to SEQ ID NO: 9. In another embodiment, the polynucleotide with one or more non-transgenic mutations listed in Table 5 is 85%, 86%, 87%, 88%, 89%, 90%, 91%, 92%, 93%, 94%, 95%, 96%, 97%, 98%, 99% or greater than 99% identical to SEQ ID NO: 9. In yet another embodiment, the polynucleotide with one or more non-transgenic mutations listed in Table 5 is 85%, 86%, 87%, 88%, 89%, 90%, 91%, 92%, 93%, 94%, 95%, 96%, 97%, 98%, 99% or greater than 99% similar to SEQ ID NO: 9.

In still another embodiment, the polynucleotide with one or more non-transgenic mutation listed in Table 5 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 10. In still another embodiment, the SBEIIb protein with one or more non-transgenic mutations is 85%, 86%, 87%, 88%, 89%, 90%, 91%, 92%, 93%, 94%, 95%, 96%, 97%, 98%, 99% or greater than 99% similar to SEQ ID NO: 10.

Examples of mutations created and identified in SBEIIb in the D genome of wheat plants are provided in Table 6. Nucleotide and amino acid changes are identified according to their positions in SEQ ID NOs: 11 and 12, respectively.

TABLE 6

Representative mutations in SBEIIb in the D genome

| Variety | Primer SEQ IDs. | Nucleotide Mutation | A.A. Mutation | PSSM | SIFT |
|---|---|---|---|---|---|
| Express | 49, 50 | G1691A | G58E | | 0.76 |
| Express | 49, 50 | C1742T | P75L | 17 | 0.01 |
| Express | 49, 50 | A1753G | S79G | 8.8 | 0.17 |
| Express | 49, 50 | T1770C | P84= | | |
| Express | 49, 50 | C1784T | P89L | | 0.28 |
| Express | 49, 50 | C1831T | Intron | | |
| Express | 49, 50 | G1840A | Intron | | |
| Express | 49, 50 | C1844T | Intron | | |
| Express | 49, 50 | C1844T | Intron | | |
| Express | 49, 50 | C2438T | Intron | | |
| Express | 49, 50 | C2438T | Intron | | |
| Express | 49, 50 | C2463T | Intron | | |
| Express | 49, 50 | C2479T | P100S | | 0.32 |
| Express | 49, 50 | T2511A | D110E | | 0.98 |
| Express | 49, 50 | C2548T | Q123* | | |
| Express | 49, 50 | G2575A | D132N | | 0.39 |
| Express | 49, 50 | G2649A | Q156= | | |
| Express | 49, 50 | C2672T | T164M | −5.3 | 0.46 |
| Express | 49, 50 | C2676T | L165= | | |
| Express | 51, 52 | C3142T | Intron | | |
| Express | 51, 52 | C3146T | Intron | | |
| Express | 51, 52 | G3159A | Intron | | |
| Express | 51, 52 | G3185A | R180K | | 1 |
| Express | 51, 52 | G3188A | R181K | | 0.81 |
| Express | 51, 52 | G3226A | D194N | 7 | 0.07 |
| Express | 51, 52 | G3226A | D194N | 7 | 0.07 |
| Express | 51, 52 | G3226A | D194N | 7 | 0.07 |
| Express | 51, 52 | G3229A | V195I | 5.1 | 0.13 |
| Express | 51, 52 | C3237T | S197= | | |
| Express | 51, 52 | C3246T | Y200= | | |
| Express | 51, 52 | G3266A | R207H | 8.9 | 0.52 |
| Express | 51, 52 | G3270A | Splice Junction | | |
| Express | 51, 52 | C3279T | Intron | | |
| Express | 51, 52 | C3292T | Intron | | |
| Express | 51, 52 | C3303T | Intron | | |
| Express | 51, 52 | C3318T | Intron | | |
| Express | 51, 52 | C3330T | Intron | | |
| Express | 51, 52 | C3332T | Intron | | |
| Express | 51, 52 | G3345A | A209T | 5.3 | 0.49 |
| Express | 51, 52 | G3345A | A209T | 5.3 | 0.49 |
| Express | 51, 52 | C3346T | A209V | 9.8 | 0.25 |
| Express | 51, 52 | C3346T | A209V | 9.8 | 0.25 |
| Express | 51, 52 | C3346T | A209V | 9.8 | 0.25 |
| Express | 51, 52 | G3364A | R215Q | 17.7 | 0.01 |
| Express | 51, 52 | C3410T | Intron | | |
| Express | 51, 52 | C3410T | Intron | | |
| Express | 51, 52 | C3416T | Intron | | |
| Express | 51, 52 | G3571A | A224T | 16.7 | 0.01 |
| Express | 51, 52 | G3599A | W233* | | |
| Express | 51, 52 | G3628A | Splice Junction | | |
| Express | 51, 52 | C3662T | Intron | | |
| Express | 51, 52 | C3662T | Intron | | |
| Express | 53, 54 | C4138T | G265= | | |
| Express | 53, 54 | C4060T | Intron | | |
| Express | 53, 54 | G4080A | G246D | | 0 |
| Express | 53, 54 | C4124T | P261S | | 0.07 |
| Express | 53, 54 | C4142T | R267W | 18 | 0 |
| Express | 53, 54 | G4144A | R267= | | |
| Express | 53, 54 | C4159T | Intron | | |
| Express | 53, 54 | C4197A | Intron | | |
| Express | 53, 54 | C4213T | Intron | | |
| Express | 53, 54 | G4229A | Splice Junction | | |
| Express | 53, 54 | G4229A | Splice Junction | | |
| Express | 53, 54 | C4246T | P275L | 16.1 | 0.05 |
| Express | 53, 54 | C4246T | P275L | 16.1 | 0.05 |
| Express | 53, 54 | G4260A | D280N | 15.8 | 0.07 |
| Express | 53, 54 | C4280T | I286= | | |
| Express | 53, 54 | G4290A | V290M | 13.3 | 0.01 |
| Express | 53, 54 | C4299T | P293S | 8.1 | 0.29 |
| Express | 53, 54 | G4303A | G294E | 4 | 0.25 |
| Express | 53, 54 | C4311T | P297S | 17.3 | 0.07 |

TABLE 6-continued

Representative mutations in SBEIIb in the D genome

| Variety | Primer SEQ IDs. | Nucleotide Mutation | A.A. Mutation | PSSM | SIFT |
|---|---|---|---|---|---|
| Express | 53, 54 | G4347A | Splice Junction | | |
| Express | 53, 54 | C4361T | Intron | | |
| Express | 53, 54 | G4515A | Intron | | |
| Express | 53, 54 | C4546T | P316S | 9.2 | 0.13 |
| Express | 53, 54 | C4546T | P316S | 9.2 | 0.13 |
| Express | 53, 54 | C4546T | P316S | 9.2 | 0.13 |
| Express | 53, 54 | C4546T | P316S | 9.2 | 0.13 |
| Express | 53, 54 | C4547T | P316L | 18.1 | 0.01 |
| Express | 53, 54 | C4573T | R325W | 22.1 | 0 |
| Express | 53, 54 | C4605T | S335= | | |
| Express | 53, 54 | G4609A | Splice Junction | | |
| Express | 53, 54 | G4609A | Splice Junction | | |
| Express | 53, 54 | C4618T | Intron | | |
| Express | 57, 58 | C7427T | D425= | | |
| Express | 57, 58 | C7450T | T433M | 12.8 | 0 |
| Express | 57, 58 | G7471A | G440D | 2.1 | 0.26 |
| Express | 57, 58 | C7488T | H446Y | 23.3 | 0 |
| Express | 57, 58 | C7506T | R452C | 25.4 | 0 |
| Express | 57, 58 | C7506T | R452C | 25.4 | 0 |
| Express | 57, 58 | G7537A | Intron | | |
| Express | 57, 58 | C7597T | Intron | | |
| Express | 57, 58 | G7635A | R463= | | |
| Express | 57, 58 | G7655A | R470K | 13.6 | 0.05 |
| Express | 57, 58 | G7669A | E475K | 17.2 | 0 |
| Express | 57, 58 | G7685A | G480D | 26 | 0 |
| Express | 57, 58 | C7689T | F481= | | |
| Express | 57, 58 | G7700A | G485D | 26 | 0 |
| Express | 57, 58 | G7702A | A486T | 5.3 | 0 |
| Express | 57, 58 | C7758T | Intron | | |
| Express | 57, 58 | C7886T | Intron | | |
| Express | 57, 58 | G7897A | V498I | | 0.13 |
| Express | 57, 58 | C7917T | Y504= | | |
| Express | 57, 58 | C7952T | A516V | 18.5 | 0 |
| Express | 57, 58 | G7968A | M521I | 18.9 | 0 |
| Express | 57, 58 | G8056A | Intron | | |

In one embodiment, the invention relates to a polynucleotide of the SBEIIb gene of the D genome with one or more non-transgenic mutations listed in Table 6 and corresponding to SEQ ID NO: 11. In another embodiment, the polynucleotide with one or more non-transgenic mutations listed in Table 6 is 85%, 86%, 87%, 88%, 89%, 90%, 91%, 92%, 93%, 94%, 95%, 96%, 97%, 98%, 99% or greater than 99% identical to SEQ ID NO: 11. In yet another embodiment, the polynucleotide with one or more non-transgenic mutations listed in Table 6 is 85%, 86%, 87%, 88%, 89%, 90%, 91%, 92%, 93%, 94%, 95%, 96%, 97%, 98%, 99% or greater than 99% similar to SEQ ID NO: 11.

In still another embodiment, the polynucleotide with one or more non-transgenic mutation listed in Table 6 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 12. In still another embodiment, the SBEIIb protein with one or more non-transgenic mutations is 85%, 86%, 87%, 88%, 89%, 90%, 91%, 92%, 93%, 94%, 95%, 96%, 97%, 98%, 99% or greater than 99% similar to SEQ ID NO: 12.

3. Mutations in Both SBEIIa and SBEIIb Genes

In one embodiment, the invention relates to multiple non-transgenic mutations in the SBEIIa gene including but not limited to 1, 2, 3, 4, 5, 6, 7, 8, 9, 10, and greater than 10 mutations and multiple non-transgenic mutations in the SBEIIb gene including but not limited to 1, 2, 3, 4, 5, 6, 7, 8, 9, 10, and greater than 10 mutations.

In still another embodiment, one or more mutations are in each of the SBEIIa and SBEIIb genes of the A genome. In one embodiment, the invention relates to multiple non-transgenic mutations in the SBEIIa gene including but not limited to 1, 2, 3, 4, 5, 6, 7, 8, 9, 10, and greater than 10 mutations and multiple non-transgenic mutations in the SBEIIb gene including but not limited to 1, 2, 3, 4, 5, 6, 7, 8, 9, 10, and greater than 10 mutations.

In another embodiment, one or more mutations are in each of the SBEIIa and SBEIIb genes of the B genome. In still another embodiment, one or more mutations are in each of the SBEIIa and SBEIIb genes of the D genome. In yet another embodiment, one or more mutations are in each of the SBEIIa and SBEIIb genes of the A and B genomes. In still another embodiment, one or more mutations are in each of the SBEIIa and SBEIIb genes of the A and D genomes. In another embodiment, one or more mutations are in each of the SBEIIa and SBEIIb genes of the B and D genomes. In yet another embodiment, one or more mutations are in each of the SBEIIa and SBEIIb genes of the A, B, and D genomes. In yet another embodiment, one or more mutations are in each of the SBEIIa genes of the A, B, and D genomes and additional mutations are in more or more of the SBEIIb genes of the A, B, and D genomes.

B. SBEII Proteins

Starch is a mixture of amylose and amylopectin, both of which are Glc polymers. Amylose is a mostly linear polymer of 200 to 2000 α-1,4-bonded Glc moieties with rare α-1,6 branch points (for reviews, see Martin and Smith, 1995; Ball et al., 1996). Amylopectin is highly α-1,6-branched, with a complex structure of $10^6$ to $10^8$ $M_r$ and up to $3 \times 10^6$ Glc subunits, making it one of the largest biological molecules in nature.

In the plant, starch is deposited as starch granules in chloroplasts of photosynthetic tissues or in amyloplasts of endosperm, embryos, tubers, and roots. In most plants, starch consists of 20% to 30% amylose and 70% to 80% amylopectin. In photosynthetic and nonphotosynthetic tissues the Glc moiety of ADP-Glc is incorporated in the growing amylose polymer with the help of starch synthases. The formation of α-1,6 linkages in amylopectin is catalyzed by SBEs.

In yet another embodiment, the invention relates to one or more non-trangenic mutations in the SBEII gene (as discussed above in the section entitled SBEII Mutations) that result in an SBEII protein with one or more mutations as compared to wild type SBEII protein. In one embodiment, the non-trangenic mutations include but are not limited to the mutations recited in Tables 1-6 and 8-12, corresponding mutations in homoeologues, and combinations thereof.

In another embodiment, the invention relates to one or more non-trangenic mutations in the SBEII gene that inhibits production of the SBEII protein. In some embodiments, a mutation in the SBEII gene inhibits expression of the SBEII protein. In other embodiments, a mutation in the SBEII gene creates an unstable or reduced function SBEII protein.

In another embodiment, the expression level of SBEII protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type SBEII protein.

In yet another embodiment, the expression level of SBEIIa protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type SBEIIa protein.

In still another embodiment, the expression level of SBEIIb protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type SBEIIb protein.

In yet another embodiment, the activity of the SBEII protein with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and greater than 99% of the activity level of the wild type SBEII protein. In another embodiment, the SBEII protein with one or more mutations disclosed herein has no activity or zero activity as compared to wild type SBEII protein.

In still another embodiment, the activity of the SBEIIa protein with one or more mutations disclosed herein is reduced to 0-1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and greater than 99% of the activity level of the wild type SBEIIa protein. In another embodiment, the SBEIIa protein with one or more mutations disclosed herein has no activity or zero activity as compared to wild type SBEIIa protein.

In yet another embodiment, the activity of the SBEIIb protein with one or more mutations disclosed herein is reduced to 0-1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and greater than 99% of the activity level of the wild type SBEIIb protein. In another embodiment, the SBEIIb protein with one or more mutations disclosed herein has no activity or zero activity as compared to wild type SBEIIb protein.

C. Wheat Cultivars

In one embodiment, a wheat cultivar having at least one SBEII gene that is diploid, polyploid, tertraploid, and hexaploid may be used.

In another embodiment, the wheat is *Triticum aestivum*.

In one embodiment, any cultivar of wheat can be used to create mutations in an SBEII gene. In one embodiment, any cultivar of wheat can be used to create mutations in an SBEIIa gene. In another embodiment, any cultivar of wheat can be used to create mutations in an SBEIIb gene.

In one embodiment, any cultivar of wheat can be used as lines to cross SBEII mutations into different cultivars. In still another embodiment, any cultivar of wheat can be used as lines to cross SBEIIa mutations into different cultivars. In another embodiment, any cultivar of wheat can be used as lines to cross SBEIIb mutations into different cultivars.

In another embodiment, any cultivar of wheat having at least one SBEII gene may be used including but not limited to hard red spring wheat, hard white wheat, durum wheat, soft white spring wheat, soft white winter wheat, hard red winter wheat, common wheat, splelt wheat, emmer wheat, pasta wheat and turgidum wheat.

In one embodiment, hard red spring wheat includes but is not limited to Bullseye, Cabernet, Cal Rojo, Hank, Joaquin, Kelse, Lariat, Lassik, Malbec, Mika, PR 1404, Redwing, Summit 515, SY 314, Triple IV, Ultra, WB-Patron, WB-Rockland, Yecora Rojo, Accord, Aim, Anza, Baker, Beth Hashita, Bonus, Borah, Brim, Brooks, Buck Pronto, Butte 86, Cavalier, Challenger, Chief, Ciano T79, Colusa, Companion, Copper, Cuyama, Dash 12, Eldon, Enano, Express, Expresso, Jefferson, Genero F81, Grandin, Helena 554, Hollis, Imuris T79, Inia 66R, Jerome, Kern, Len, Marshall, McKay, Nomad, Northwest 10, Oslo, Pavon F76, Pegasus, Pitic 62, Poco Red, Powell, Probrand 711, Probrand 751, Probrand 771, Probrand 775, Probred, Prointa Queguay, Prointa Quintal, Rich, RSI 5, Sagittario, Scarlet, Serra, Shasta, Solano, Spillman, Sprite, Stander, Stellar, Stoa, Success, Summit, Sunstar 2, Sunstar King, Tadinia, Tammy, Tanori 71, Tara 2000, Tempo, Tesia T79, Topic, UI Winchester, Vance, Vandal, W444, Wampum, Wared, WB-Fuzion, Westbred 906R, Westbred 911, Westbred 926, Westbred 936, Westbred Discovery, Westbred Rambo, Yolo, and Zeke.

In another embodiment, hard white wheat includes but is not limited to Blanca Fuerte, Blanca Grande 515, Blanca Royale, Clear White, Patwin, Patwin 515, WB-Cristallo, WB-Paloma, WB-Perla, Alta Blanca, Blanca Grande, Delano, Golden Spike, ID377S, Klasic, Lochsa, Lolo, Macon, Otis, Phoenix, Pima 77, Plata, Pristine, Ramona 50, Siete Cerros 66, Vaiolet, and Winsome.

In yet another embodiment, durum wheat includes but is not limited to Crown, Desert King, Desert King HP, Duraking, Fortissimo, Havasu, Kronos, Maestrale, Normanno, Orita, Platinum, Q-Max, RSI 59, Saragolla, Tango, Tipai, Topper, Utopia, Volante, WB-Mead, Westmore, Aldente, Aldura, Altar 84, Aruba, Bittern, Bravadur, Candura, Cortez, Deluxe, Desert Titan, Durex, Durfort, Eddie, Germains 5003D, Imperial, Kofa, Levante, Matt, Mead, Mexicali 75, Minos, Modoc, Mohawk, Nudura, Ocotillo, Produra, Reva, Ria, Septre, Sky, Tacna, Titan, Trump, Ward, Westbred 803, Westbred 881, Westbred 883, Westbred 1000D, Westbred Laker, Westbred Turbo, and Yavaros 79.

In another embodiment, soft white spring wheat includes but is not limited to Alpowa, Alturas, Babe, Diva, JD, New Dirkwin, Nick, Twin, Whit, Blanca, Bliss, Calorwa, Centennial, Challis, Dirkwin, Eden, Edwall, Fielder, Fieldwin, Jubilee, Louise, Owens, Penawawa, Pomerelle, Sterling, Sunstar Promise, Super Dirkwin, Treasure, UI Cataldo, UI Pettit, Urquie, Vanna, Waduel, Waduel 94, Wakanz, Walladay, Wawawai, Whitebird, and Zak.

In still another embodiment, soft white winter wheat includes but is not limited to AP Badger, AP Legacy, Brundage 96, Bruneau, Cara, Goetze, Legion, Mary, Skiles, Stephens, SY Ovation, Tubbs, WB-Junction, WB-528, Xerpha, Yamhill, Barbee, Basin, Bitterroot, Bruehl, Castan, Chukar, Coda, Daws, Edwin, Eltan, Faro, Finch, Foote, Gene, Hill 81, Hiller, Hubbard, Hyak, Hyslop, Idaho 587, Kmor, Lambert, Lewjain, MacVicar, Madsen, Malcolm, Masami, McDermid, Moro, Nugaines, ORCF-101, ORCF-102, ORCF-103, Rod, Rohde, Rulo, Simon, Salute, Temple, Tres, Tubbs 06, UICF-Brundage, WB-523, and Weatherford.

In another embodiment, hard red winter wheat includes but is not limited to Andrews, Archer, Batum, Blizzard, Bonneville, Boundary, Declo, Deloris, Finley, Garland, Hatton, Hoff, Longhorn, Manning, Meridian, Promontory, Vona, Wanser, Winridge.

In another embodiment, common wheat (hexaploid, free threshing), *Triticum aestivum* ssp *aestivum* includes but is not limited to Sonora, Wit Wolkoring, Chiddam Blanc De Mars, India-Jammu, Foisy.

In still another embodiment, spelt wheat (hexaploid, not free threshing), *Triticum aestivum* ssp *spelta* includes but is not limited to Spanish Spelt, Swiss Spelt.

In yet another embodiment, Emmer Wheat (tetraploid), *Triticum turgidum* ssp. *dicoccum* includes but is not limited to Ethiopian Blue Tinge.

In another embodiment, pasta wheat (tetraploid, free threshing), *Triticum turgidum* ssp durum includes but is not limited to Blue Beard, Durum-Iraq.

In yet another embodiment, *Turgidum* Wheat (tetraploid, free threshing), *Triticum turgidum* ssp *turgidum* includes but is not limited to Akmolinka, Maparcha.

In one embodiment, a cultivar of wheat having at least one SBEII gene with substantial percent identity to SEQ ID NO: 1, SEQ ID NO: 3, SEQ ID NO: 5, SEQ ID NO: 7, SEQ ID NO: 9, or SEQ ID NO: 11 may be used in the invention.

As used herein with regard to the wheat cultivars, "substantial percent identity" means that the DNA sequence of the gene is sufficiently similar to SEQ ID NO: 1, 3, 5, 7, 9, or 11 at the nucleotide level to code for a substantially similar protein, allowing for allelic differences (or alternate mRNA splicing) between cultivars. In accordance with one embodiment of the invention, "substantial percent identity" may be present when the percent identity in the coding region between the SBEII gene and SEQ ID NO: 1, 3, 5, 7, 9, or 11 is as low as about 85%, provided that the percent identity in the conserved regions of the gene is higher (e.g., at least about 90%). Preferably the percent identity in the coding region is 85-90%, more preferably 90-95%, and optimally, it is above 95%. Thus, one of skill in the art may prefer to utilize a wheat cultivar having commercial popularity or one having specific desired characteristics in which to create the SBEII-mutated wheat plants, without deviating from the scope and intent of the present invention. Alternatively, one of skill in the art may prefer to utilize a wheat cultivar having few polymorphisms, such as an in-bred cultivar, in order to facilitate screening for mutations within one or more SBEII genes in accordance with the present invention.

Representative Methodology for Identification of SBEII Mutations

In order to create and identify the SBEII mutations and wheat plants of the invention, a method known as TILLING was utilized. See McCallum et al., *Nature Biotechnology* 18:455-457, 2000; McCallum et al., *Plant Physiology*, 123: 439-442, 2000; U.S. Publication No. 20040053236; and U.S. Pat. No. 5,994,075, all of which are incorporated herein by reference. In the basic TILLING methodology, plant materials, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

The hexaploid cultivar Express and the tetraploid cultivar Kronos were used.

In one embodiment, seeds from wheat are mutagenized and then grown into M1 plants. The M1 plants are then allowed to self-pollinate and seeds from the M1 plant are grown into M2 plants, which are then screened for mutations in their SBEII loci. While M1 plants can be screened for mutations in accordance with alternative embodiments of the invention, one advantage of screening the M2 plants is that all somatic mutations correspond to germline mutations.

One of skill in the art will understand that a variety of wheat plant materials, including, but not limited to, seeds, pollen, plant tissue or plant cells, may be mutagenized in order to create the SBEII-mutated wheat plants of the invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for SBEII mutations instead of waiting until the M2 generation.

Mutagens that create primarily point mutations and short deletions (about 1 to about 30 nucleotides), insertions, transversions, and or transitions, such as chemical mutagens or radiation, may be used to create the mutations. Mutagens conforming with the method of the invention include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino] acridine dihydrochloride (ICR-170), and formaldehyde. Spontaneous mutations in an SBEII gene that may not have been directly caused by the mutagen can also be identified.

Any suitable method of plant DNA preparation now known or hereafter devised may be used to prepare the wheat plant DNA for SBEIIa and SBEIIb mutation screening. For example, see Chen & Ronald, *Plant Molecular Biology Reporter* 17:53-57, 1999; Stewart and Via, *Bio Techniques* 14:748-749, 1993. Additionally, several commercial kits designed for this purpose are available, including kits from Qiagen (Valencia, CA) and Qbiogene (Carlsbad, CA).

In one embodiment, prepared DNA from individual wheat plants are pooled in order to expedite screening for mutations in one or more SBEII genes of the entire population of plants originating from the mutagenized plant tissue. The size of the pooled group may be dependent upon the sensitivity of the screening method used. Preferably, groups of two or more individual wheat plants are pooled.

In another embodiment, after the DNA samples are pooled, the pools are subjected to SBEIIa or SBEIIb sequence-specific amplification techniques, such as Polymerase Chain Reaction (PCR). For a general overview of PCR, see *PCR Protocols: A Guide to Methods and Applications* (Innis, Gelfand, Sninsky, and White, eds.), Academic Press, San Diego, 1990.

Any primer specific to an SBEIIa locus or an SBEIIb locus or the sequences immediately adjacent to one of these loci may be utilized to amplify the SBEII sequences within the pooled DNA sample. Preferably, the primer is designed to amplify the regions of the SBEII locus where useful mutations are most likely to arise. Most preferably, the primer is designed to detect exonic regions of one or more SBEII genes. Additionally, it is preferable for the primer to target known polymorphic sites to design genome specific primers in order to ease screening for point mutations in a particular genome. To facilitate detection of PCR products on a gel, the PCR primer may be labeled using any conventional or hereafter devised labeling method.

In one embodiment, primers are designed based upon the SBEIIa and SBEIIb homoeologs (SEQ ID NOs: 1, 3, 5, 7, 9, and 11). Exemplary primers (SEQ ID NOs: 13-58) that have proven useful in identifying useful mutations within the SBEIIa and SBEIIb sequences are shown below in Table 1. These primers are also detailed in the Sequence Listing appended hereto.

TABLE 7

Exemplary Primers

| SEQ ID NO | Region Screened | Sequence |
|---|---|---|
| 13 | Sbe2a_A_Exon2-3 | ACGGCTTTGATCATCTCCTCCCA |
| 14 | Sbe2a_A_Exon2-3 | TTTGTCTCTTTGATGTTCCCCAAAT |
| 15 | Sbe2a_A_Exon7-9 | TATGACCAGAGTATGTCTACAGCTTGGCAAT |
| 16 | Sbe2a_A_Exon7-9 | TGCATCCTAAGTGGGAAACCCTAACCA |
| 17 | Sbe2a_A_Exon12-14 | TCAATTTGGATCAGAGGGGATAGTCCA |
| 18 | Sbe2a_A_Exon12-14 | TGACAAGGTTGCCCATTTCTAATGCAA |
| 19 | Sbe2a_B_Exon2-3 | GATAGCTGGATTAGGCGATCGCCTCAGG |
| 20 | Sbe2a_B_Exon2-3 | TTGGTAGAGGAATTAGCAAAGTAAAATCCA |
| 21 | Sbe2a_B_Exon7-9 | GGTAGAACCTTTTGCATTATGTGTGCTTTTCC |
| 22 | Sbe2a_B_Exon7-9 | GCTACCTCGAAATGCAATGGAAATCTTAGAGAC |
| 23 | Sbe2a_B_Exon12-14 | CCAAGGAGGGAGTGAGGAGCTTGACTT |
| 24 | Sbe2a_B_Exon12-14 | TGTCAGCTTGAATGCCCTTGCACTTCT |
| 25 | Sbe2a_D_Exon2-3 | GATCGCGCTTCCTGAACCTGTAT |
| 26 | Sbe2a_D_Exon2-3 | CTCAGACCACGAAGGGATCTGTATG |
| 27 | Sbe2a_D_Exon7-9 | ATGAATACGTGCAACACTCCCATCTGC |
| 28 | Sbe2a_D_Exon7-9 | GGAAGCAAAGTTTTGCACTTGCCAATATG |
| 29 | Sbe2a_D_Exon10-11 | CGTCTCCAGCAAGCCATTTCCTACCTTA |
| 30 | Sbe2a_D_Exon10-11 | TTTTGCCACTAGTTTTGCCAATTTTCC |
| 31 | Sbe2a_D_Exon12-14 | TCAATCAATTTGGATCAGAGGGAACATCA |
| 32 | Sbe2a_D_Exon12-14 | TAGCAGTGCAGGAATTTAAGTTAAACCACTATTACA |
| 33 | Sbe2b_A_Exon2-3 | CTCCCATTCTCGTTTATTCGTAGC |
| 34 | Sbe2b_A_Exon2-3 | GTTCGGTTACCATGTCACCTCAGAGC |
| 35 | Sbe2b_A_Exon4-7 | GCCAATTGAACAACAATGCCACTTCATT |
| 36 | Sbe2b_A_Exon4-7 | GAGTACCCATTCGCACCTAGATGT |
| 37 | Sbe2b_A_Exon7-9 | GCCTGTTGCACGAGCCCATTAATTACT |
| 38 | Sbe2b_A_Exon7-9 | TTCGAACAAATGGACACCAGCTTTTGAT |
| 39 | Sbe2b_A_Exon10-11 | TTATATATCAACTTATGAATCCTGAACG |
| 40 | Sbe2b_A_Exon10-11 | GTAAAGTGTTCTTTTAGCAATTTATACAAAC |
| 41 | Sbe2b_B_Exon1-3 | GCCTCCTCATTTCGCTCGCGTGGGTTTAAG |
| 42 | Sbe2b_B_Exon1-3 | AGTGACTATGAACTTCAAGAATTTCGTGATACATCA |
| 43 | Sbe2b_B_Exon4-6 | CTACAAAAAATTGAACAACGATGCCACTTCAT |
| 44 | Sbe2b_B_Exon4-6 | CCAACTATATTTACAGCTCAACTCTGG |
| 45 | Sbe2b_B_Exon7-9 | ACTGATTTGTTCTTGCAAGACATTCA |
| 46 | Sbe2b_B_Exon7-9 | CAAATGGACACCAGCTTTTGATGC |
| 47 | Sbe2b_B_Exon10-11 | AAAGTTAGCTATATGCAGTTTAAGTTAATTTACAGGT |
| 48 | Sbe2b_B_Exon10-11 | TGTAAGATGTTCTTTCAGCAATTTATACTA |
| 49 | Sbe2b_D_Exon2-3 | ACGACGCGTGCCGATTCCGTAT |

TABLE 7-continued

Exemplary Primers

| SEQ ID NO | Region Screened | Sequence |
|---|---|---|
| 50 | Sbe2b_D_Exon2-3 | GCCATTCACATCTTATCAAAGACTGTAAATTGTTT |
| 51 | Sbe2b_D_Exon4-7 | ATCCTACAAAAAATTGAACAACAATGCCACTTTC |
| 52 | Sbe2b_D_Exon4-7 | ACATGGAGCTACAGTTCAGATGTGC |
| 53 | Sbe2b_D_Exon7-9 | GCCTGTTGCACGAGCCCATTACTAGAT |
| 54 | Sbe2b_D_Exon7-9 | GGCAATTACTTGTTTCTTTGTGCAATTACTTGTT |
| 55 | Sbe2b_D_Exon10-11 | GTTTTGAATGCTCAAGAGAAGTACTAGT |
| 56 | Sbe2b_D_Exon10-11 | TGTAAGATGTTCTTTCAGCAATTTATACTA |
| 57 | Sbe2b_D_Exon12-14 | TTATGTCTTGGTCCAAAGCCCCTTTTTG |
| 58 | Sbe2b_D_Exon12-14 | TCCACGTCAGGAACTTAGACATGCAACTAT |

In another embodiment, the PCR amplification products may be screened for SBEII mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al., *Electrophoresis* 23(10):1499-1511, 2002), or by fragmentation using enzymatic cleavage, such as used in the high throughput method described by Colbert et al., *Plant Physiology* 126:480-484, 2001. Preferably, the PCR amplification products are incubated with an endonuclease that preferentially cleaves mismatches in heteroduplexes between wild type and mutant sequences.

In another embodiment, cleavage products are electrophoresed using an automated sequencing gel apparatus, and gel images are analyzed with the aid of a standard commercial image-processing program.

In yet another embodiment, once an M2 plant having a mutated SBEII gene sequence is identified, the mutations are analyzed to determine their effect on the expression, translation, and/or activity of an SBEII enzyme. In one embodiment, the PCR fragment containing the mutation is sequenced, using standard sequencing techniques, in order to determine the exact location of the mutation in relation to the overall SBEII sequence. Each mutation is evaluated in order to predict its impact on protein function (i.e., from completely tolerated to causing loss-of-function) using bioinformatics tools such as SIFT (Sorting Intolerant from Tolerant; Ng and Henikoff, *Nucleic Acids Research* 31:3812-3814, 2003), PSSM (Position-Specific Scoring Matrix; Henikoff and Henikoff, *Computer Applications in the Biosciences* 12:135-143, 1996) and PARSESNP (Taylor and Greene, *Nucleic Acids Research* 31:3808-3811, 2003). For example, a SIFT score that is less than 0.05 and a large change in PSSM score (e.g., roughly 10 or above) indicate a mutation that is likely to have a deleterious effect on protein function. These programs are known to be predictive, and it is understood by those skilled in the art that the predicted outcomes are not always accurate.

In another embodiment, if the initial assessment of a mutation in the M2 plant indicates it to be of a useful nature and in a useful position within an SBEII gene, then further phenotypic analysis of the wheat plant containing that mutation may be pursued. In hexaploid wheat, mutations in each of the A, B and D genomes usually must be combined before a phenotype can be detected. In tetraploid wheat, A and B genome mutations are combined. In addition, the mutation containing plant can be backcrossed or outcrossed two times or more in order to eliminate background mutations at any generation. Then the backcrossed or outcrossed plant can be self-pollinated or crossed in order to create plants that are homozygous for the SBEII mutations.

Several physical characteristics of these homozygous SBEII mutant plants are assessed to determine if the mutation results in a useful phenotypic change in the wheat plant without resulting in undesirable negative effects, such as significantly reduced seed yields.

Methods of Producing a Wheat Plant

In another embodiment, the invention relates to a method for producing a wheat plant with increased resistant starch levels. In another embodiment, the invention relates to a method for producing a wheat plant with an increased proportion of amylose in the starch.

In another embodiment, the invention relates to a method of out-crossing SBEII gene mutations to wild type wheat. In another embodiment, the invention relates to a method of out-crossing SBEIIa gene mutations to wild type wheat. In another embodiment, the invention relates to a method of out-crossing SBEIIb gene mutations to wild type wheat.

In another embodiment, the invention relates to a method for producing a wheat plant having increased amylose content. In still another embodiment, the invention relates to a method for producing a wheat plant having reduced activity of one or more SBEII enzymes compared to the wild type wheat plants.

In one embodiment, the method comprises inducing at least one non-transgenic mutation in at least one copy of an SBEII gene in plant material or plant parts from a parent wheat plant; growing or using the mutagenized plant material to produce progeny wheat plants; analyzing mutagenized plant material and/or progeny wheat plants to detect at least one mutation in at least one copy of a SBEII gene; and selecting progeny wheat plants that have at least one mutation in at least one copy of an SBEII gene.

In another embodiment, the method further comprises crossing progeny wheat plants that have at least one mutation in at least one copy of an SBEII gene with other progeny wheat plants that have at least one mutation in a different copy of an SBEII gene. The process of identifying progeny wheat plants with mutations and crossing said progeny wheat plants with other progeny wheat plants, which have mutations, can be repeated to produce progeny wheat plants with reduced SBEII enzyme activity.

In another embodiment, the level of activity of the SBEII protein in the wheat plant is reduced and selected from the group consisting of 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, 95-99% of the level of activity of the SBEII protein in the wild type plant.

In still another embodiment, the level of activity of the SBEIIa protein in the wheat plant is reduced compared to the wild type plant and is selected from the group consisting of 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, 95-99% of the level of activity of the SBEIIa protein in the wild type plant.

In yet another embodiment, the level of activity of the SBEIIb protein in the wheat plant is reduced and selected from the group consisting of 0-2% 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, 95-99% of the level of activity of the SBEIIb protein in the wild type plant.

A. Methods of Producing a Wheat Plant with One or More Mutations in the SBEIIa Gene in More than One Genome In still another embodiment, the invention relates to a method for producing a wheat plant comprising inducing at least one non-transgenic mutation in at least one copy of an SBEIIa gene in plant material from a parent wheat plant that comprises a mutation in an SBEIIa gene; growing or using the mutagenized plant material to produce progeny wheat plants; and selecting progeny wheat plants that have at least one mutation in at least two copies of an SBEIIa gene.

For example, the parent wheat plant may have a mutation in an SBEIIa gene of the A genome. The selected progeny wheat plants may have a mutation in an SBEIIa gene of the A genome and one or more mutations in the SBEIIa gene of the B genome. This example is provided merely for clarification and should not limit the methods disclosed herein.

In yet another embodiment, the invention relates to a method for producing a wheat plant comprising inducing at least one non-transgenic mutation in at least one copy of an SBEIIa gene in plant material from a parent wheat plant that comprises at least one mutation in two SBEIIa genes; growing or using the mutagenized plant material to produce progeny wheat plants; and selecting progeny wheat plants that have at least one mutation in three copies of an SBEIIa gene. In this embodiment, there would be at least one mutation in the SBEIIa gene of the A, B and D genomes.

In another embodiment, the invention relates to a method for producing a wheat plant comprising crossing a first wheat plant that has at least one non-transgenic mutation in a first SBEIIa gene with a second wheat plant that has at least one non-transgenic mutation in a second SBEIIa gene; and selecting progeny wheat plants that have at least one mutation in at least two copies of an SBEIIa gene.

In another embodiment, the invention relates to a method for producing a wheat plant comprising crossing a first wheat plant that has at least one non-transgenic mutation in a first and second SBEIIa gene with a second wheat plant that has at least one non-transgenic mutation in a third SBEIIa gene; and selecting progeny wheat plants that have at least one mutation in all three copies of an SBEIIa gene.

In this embodiment, there would be at least one mutation in the SBEIIa gene of the A, B and D genomes.

In another embodiment, the grain of the wheat plant produced according to the methods disclosed herein comprises starch, and the proportion of amylose in the starch is selected from the group consisting of at least 30%, 30-35%, 35-40%, 40-45%, 45-50%, 50-55%, 55-60%, and 60-65% (w/w). In one embodiment, the proportion of amylose in the starch is 47-60% (w/w).

B. Methods of Producing a Wheat Plant with Mutations in the SBEIIb Gene in More than One Genome In still another embodiment, the invention relates to a method for producing a wheat plant comprising inducing at least one non-transgenic mutation in at least one copy of an SBEIIb gene in plant material from a parent wheat plant that comprises a mutation in an SBEIIb gene; growing or using the mutagenized plant material to produce progeny wheat plants; and selecting progeny wheat plants that have at least one mutation in at least two copies of an SBEIIb gene.

For example, the parent wheat plant may have a mutation in an SBEIIb gene of the A genome. The selected progeny wheat plants may have a mutation in an SBEIIb gene of the A genome and one or more mutations in the SBEIIb gene of the B genome. This example is provided merely for clarification and should not limit the methods disclosed herein.

In yet another embodiment, the invention relates to a method for producing a wheat plant comprising inducing at least one non-transgenic mutation in at least one copy of an SBEIIb gene in plant material from a parent wheat plant that comprises at least one mutation in two SBEIIb genes; growing or using the mutagenized plant material to produce progeny wheat plants; and selecting progeny wheat plants that have at least one mutation in three copies of an SBEIIb gene. In this embodiment, there would be at least one mutation in the SBEIIb gene of the A, B and D genomes.

In another embodiment, the invention relates to a method for producing a wheat plant comprising crossing a first wheat plant that has at least one non-transgenic mutation in a first SBEIIb gene with a second wheat plant that has at least one non-transgenic mutation in a second SBEIIb gene; and selecting progeny wheat plants that have at least one mutation in at least two copies of an SBEIIb gene.

In another embodiment, the invention relates to a method for producing a wheat plant comprising crossing a first wheat plant that has at least one non-transgenic mutation in a first and second SBEIIb gene with a second wheat plant that has at least one non-transgenic mutation in a third SBEIIb gene; and selecting progeny wheat plants that have at least one mutation in all three copies of an SBEIIb gene. In this embodiment, there would be at least one mutation in the SBEIIb gene of the A, B and D genomes.

In another embodiment, the grain of the wheat plant produced according to the methods disclosed herein comprises starch, and the proportion of amylose in the starch is selected from the group consisting of at least 30%, 30-35%, 35-40%, 40-45%, 45-50%, 55-60%, 60-65%, 65-70%, 70-75%, 75-80%, 80-85%, 85-90%, 90-95%, and greater than 95% (w/w).

C. Methods of Producing a Wheat Plant with One or More Mutations in the SBEIIa Gene and SBEIIb Gene in More than One Genome In one embodiment, the invention relates to a method of producing a wheat plant with one or more mutations in the SBEIIa gene and one or more mutations in the SBEIIb gene in one or more than one genome.

In one embodiment, the wheat plant may comprise one mutation in the SBEIIa gene and 1, 2, 3, 4, 5, 6, 7, 8, 9, 10, or more than 10 mutations in the SBEIIb gene. In one embodiment, the wheat plant may comprise 2 mutations in the SBEIIa gene and 1, 2, 3, 4, 5, 6, 7, 8, 9, 10, or more than 10 mutations in the SBEIIb gene.

In one embodiment, the wheat plant may comprise 3 mutations in the SBEIIa gene and 1, 2, 3, 4, 5, 6, 7, 8, 9, 10, or more than 10 mutations in the SBEIIb gene. In one embodiment, the wheat plant may comprise 4 mutations in the SBEIIa gene and 1, 2, 3, 4, 5, 6, 7, 8, 9, 10, or more than 10 mutations in the SBEIIb gene. In one embodiment, the wheat plant may comprise 5 mutations in the SBEIIa gene and 1, 2, 3, 4, 5, 6, 7, 8, 9, 10, or more than 10 mutations in the SBEIIb gene. In one embodiment, the wheat plant may comprise 6 mutations in the SBEIIa gene and 1, 2, 3, 4, 5, 6, 7, 8, 9, 10, or more than 10 mutations in the SBEIIb gene.

In one embodiment, the wheat plant may comprise 7 mutations in the SBEIIa gene and 1, 2, 3, 4, 5, 6, 7, 8, 9, 10, or more than 10 mutations in the SBEIIb gene. In one embodiment, the wheat plant may comprise 8 mutations in the SBEIIa gene and 1, 2, 3, 4, 5, 6, 7, 8, 9, 10, or more than 10 mutations in the SBEIIb gene. In one embodiment, the wheat plant may comprise 9 mutations in the SBEIIa gene and 1, 2, 3, 4, 5, 6, 7, 8, 9, 10, or more than 10 mutations in the SBEIIb gene. In one embodiment, the wheat plant may comprise 10 mutations in the SBEIIa gene and 1, 2, 3, 4, 5, 6, 7, 8, 9, 10, or more than 10 mutations in the SBEIIb gene.

In one embodiment, the invention relates to a method for producing a wheat plant comprising inducing at least one non-transgenic mutation in at least one copy of an SBEIIa and SBEIIb gene in plant material from a parent wheat plant that comprises a mutation in an SBEIIa and SBEIIb genes; growing or using the mutagenized plant material to produce progeny wheat plants; and selecting progeny wheat plants that have at least one mutation in at least two SBEIIa genes and at least one mutation in at least two SBEIIb genes.

For example, the parent wheat plant may have a mutation in SBEIIa and SBEIIb genes of the A genome. The selected progeny wheat plants may have a mutation in an SBEIIa and SBEIIb gene of the A genome and one or more mutations in the SBEIIa and SBEIIb genes of the B genome. This example is provided merely for clarification and should not limit the methods disclosed herein.

In yet another embodiment, the invention relates to a method for producing a wheat plant comprising inducing at least one non-transgenic mutation in at least one copy of SBEIIa and SBEIIb genes in plant material from a parent wheat plant that comprises at least one mutation in two SBEIIa genes and at least one mutation in two SBEIIb genes; growing or using the mutagenized plant material to produce progeny wheat plants; and selecting progeny wheat plants that have at least one mutation in three copies of an SBEIIa gene and at least one mutation in three copies of an SBEIIb gene. In this embodiment, there would be at least one mutation in the SBEIIa gene of the A, B and D genomes and at least one mutation in the SBEIIb gene of the A, B and D genomes.

In another embodiment, the invention relates to a method for producing a wheat plant comprising crossing a first wheat plant that has at least one non-transgenic mutation in a first SBEIIa gene and a first SBEIIb gene with a second wheat plant that has at least one non-transgenic mutation in a second SBEIIa gene and a second SBEIIb gene; and selecting progeny wheat plants that have at least one mutation in at least two copies of an SBEIIa and SBEIIb gene.

In another embodiment, the invention relates to a method for producing a wheat plant comprising crossing a first wheat plant that has at least one non-transgenic mutation in a first and second SBEIIa gene and at least one non-transgenic mutation in a first and second SBEIIb gene with a second wheat plant that has at least one non-transgenic mutation in a third SBEIIa and at least one non-transgenic mutation in a third SBEIIb gene; and selecting progeny wheat plants that have at least one mutation in all three copies of an SBEIIa and SBEIIb gene. In this embodiment, there would be at least one mutation in the SBEIIb gene of the A, B and D genomes.

In another embodiment, the grain of the wheat plant produced according to the methods disclosed herein comprises starch, and the proportion of amylose in the starch is selected from the group consisting of at least 30%, 30-35%, 35-40%, 40-45%, 45-50%, and 50-55% (w/w).

Wheat Plant, Wheat Seed and Parts of Wheat Plant

In one embodiment, a wheat plant is produced according to the methods disclosed herein. In another embodiment, the wheat plant, wheat seed or parts of a wheat plant have one or more mutations in an SBEII gene. In another embodiment, the wheat plant, wheat seed or parts of a wheat plant have one or more mutations in SBEII genes.

In another embodiment, the invention relates to a wheat plant, wheat seed or parts of a wheat plant comprising one or more non-transgenic mutations in the SBEIIa gene. In another embodiment, the invention relates to a wheat plant, wheat seed or parts of a wheat plant comprising at least one non-transgenic mutation in the SBEIIa gene in each of two genomes. In still another embodiment, the invention relates to a wheat plant, wheat seed or parts of a wheat plant comprising at least one non-transgenic mutation in the SBEIIa gene in each of three genomes.

In one embodiment, the wheat plant, wheat seed or parts of a wheat plant comprises one or more non-transgenic mutations in both alleles of the SBEIIa gene in the A genome. In another embodiment, the non-transgenic mutations are identical in both alleles of the SBEIIa gene of the A genome.

In one embodiment, the wheat plant, wheat seed or parts of a wheat plant comprises one or more non-transgenic mutations in both alleles of the SBEIIa gene in the B genome. In another embodiment, the non-transgenic mutations are identical in both alleles of the SBEIIa gene of the B genome.

In one embodiment, the wheat plant, wheat seed or parts of a wheat plant comprises one or more non-transgenic mutations in both alleles of the SBEIIa gene in the D genome. In another embodiment, the non-transgenic mutations are identical in both alleles of the SBEIIa gene of the D genome.

In one embodiment, the invention relates to a wheat plant, wheat seed or parts of a wheat plant comprising a polynucleotide of the SBEIIa gene in the A genome with one or more non-transgenic mutations listed in Table 1 and corresponding to SEQ ID NO: 1. In another embodiment, the wheat plant, wheat seed or parts of the wheat plant comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, the wheat plant, wheat seed or parts of a wheat plant comprise a polynucleotide with one or more non-transgenic mutations listed in Table 1 that codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 2.

In one embodiment, the invention relates to a wheat plant, wheat seed or parts of a wheat plant comprising a polynucleotide of the SBEIIa gene in the B genome with one or more non-transgenic mutations listed in Table 2 and corresponding to SEQ ID NO: 3. In another embodiment, the wheat plant, wheat seed or parts of a wheat plant comprises a polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical or similar to SEQ ID NO: 3.

In still another embodiment, wheat plant, wheat seed or parts of a wheat plant comprises a polynucleotide with one or more non-transgenic mutations listed in Table 2 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 4.

In one embodiment, the invention relates to a wheat plant, wheat seed or parts of a wheat plant comprising a polynucleotide of the SBEIIa gene of the D genome with one or more non-transgenic mutations listed in Table 3 and corresponding to SEQ ID NO: 5. In another embodiment, the wheat plant, wheat seed or parts of a wheat plant comprise a polynucleotide with one or more non-transgenic mutations listed in Table 3 and is 85%, 86%, 87%, 88%, 89%, 90%, 91%, 92%, 93%, 94%, 95%, 96%, 97%, 98%, 99% or greater than 99% identical or similar to SEQ ID NO: 5.

In still another embodiment, the wheat plant, wheat seed or parts of a wheat plant comprises a polynucleotide with one or more non-transgenic mutations listed in Table 3 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In still another embodiment, the invention relates to a wheat plant, wheat seed or parts of a wheat plant comprising one or more non-transgenic mutations in the SBEIIb gene. In another embodiment, the invention relates to a wheat plant, wheat seed or parts of a wheat plant comprising at least one non-transgenic mutation in the SBEIIb gene in each of two genomes. In still another embodiment, the invention relates to a wheat plant, wheat seed or parts of a wheat plant comprising at least one non-transgenic mutation in the SBEIIb gene in each of three genomes.

In one embodiment, the wheat plant, wheat seed or parts of a wheat plant comprises one or more non-transgenic mutations in both alleles of the SBEIIb gene. In one embodiment, the wheat plant, wheat seed or parts of a wheat plant comprises one or more non-transgenic mutations in both alleles of the SBEIIb gene of the A genome. In another embodiment, the non-transgenic mutations are identical in both alleles of the SBEIIb gene of the A genome.

In one embodiment, the wheat plant, wheat seed or parts of a wheat plant comprises one or more non-transgenic mutations in both alleles of the SBEIIb gene of the B genome. In another embodiment, the non-transgenic mutations are identical in both alleles of the SBEIIb gene of the B genome.

In one embodiment, the wheat plant, wheat seed or parts of a wheat plant comprises one or more non-transgenic mutations in both alleles of the SBEIIb gene of the D genome. In another embodiment, the non-transgenic mutations are identical in both alleles of the SBEIIb gene of the D genome.

In one embodiment, the invention relates to a wheat plant, wheat seed or parts of a wheat plant comprising a polynucleotide of the SBEIIb gene of the A genome with one or more non-transgenic mutations listed in Table 4 and corresponding to SEQ ID NO: 7. In another embodiment, the wheat plant, wheat seed or parts of a wheat plant comprises a polynucleotide with one or more non-transgenic mutations listed in Table 4 and is 85%, 86%, 87%, 88%, 89%, 90%, 91%, 92%, 93%, 94%, 95%, 96%, 97%, 98%, 99% or greater than 99% identical or similar to SEQ ID NO: 7.

In still another embodiment, the wheat plant, wheat seed or parts of a wheat plant comprise a polynucleotide with one or more non-transgenic mutations listed in Table 4 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 8.

In one embodiment, the invention relates to a wheat plant, wheat seed or parts of a wheat plant comprising a polynucleotide of the SBEIIb gene of the B genome with one or more non-transgenic mutations listed in Table 5 and corresponding to SEQ ID NO: 9. In another embodiment, the wheat plant, wheat seed or parts of a wheat plant comprise a polynucleotide with one or more non-transgenic mutations listed in Table 5 and is 85%, 86%, 87%, 88%, 89%, 90%, 91%, 92%, 93%, 94%, 95%, 96%, 97%, 98%, 99% or greater than 99% identical or similar to SEQ ID NO: 9.

In still another embodiment, the wheat plant, wheat seed or parts of a wheat plant comprise a polynucleotide with one or more non-transgenic mutations listed in Table 5 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 10.

In one embodiment, the invention relates to wheat plant, wheat seed or parts of a wheat plant comprising a polynucleotide of the SBEIIb gene of the D genome with one or more non-transgenic mutations listed in Table 6 and corresponding to SEQ ID NO: 11. In another embodiment, the wheat plant, wheat seed or parts of a wheat plant comprise a polynucleotide with one or more non-transgenic mutations listed in Table 6 and is 85%, 86%, 87%, 88%, 89%, 90%, 91%, 92%, 93%, 94%, 95%, 96%, 97%, 98%, 99% or greater than 99% identical or similar to SEQ ID NO: 11.

In still another embodiment, the wheat plant, wheat seed or parts of a wheat plant comprise a polynucleotide with one or more non-transgenic mutations listed in Table 6 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 12.

In another embodiment, the invention relates to a wheat plant, wheat seed or parts of a wheat plant comprising one or more non-transgenic mutations in the SBEIIa and SBEIIb genes. In another embodiment, the invention relates to a wheat plant, wheat seed or parts of a wheat plant comprising at least one non-transgenic mutation in the SBEIIa and SBEIIb genes in each of two genomes. In still another embodiment, the invention relates to a wheat plant, wheat seed or parts of a wheat plant comprising at least one non-transgenic mutation in the SBEIIa and SBEIIb genes in each of three genomes.

In still another embodiment, the invention relates to a wheat plant, wheat seed or parts of a wheat plant comprising at least one non-transgenic mutation in the SBEIIa gene in each of three genomes and one or more non-transgenic mutation in the SBEIIb gene.

In another embodiment, the wheat plant, wheat seed or parts of a wheat plant has one or more mutations in the SBEII gene including but not limited to one or more mutations enumerated in Tables 1-6 and 8-12 and corresponding mutations in the homoeologues. A wheat plant, wheat seed or parts of a wheat plant can be generated having 1, 2, 3, 4, 5, 6, 7, 8, 9, 10, 11, 12, 13, 14, 15, 16, 17, 18, 19, 20, 21, 22, 23, 24, 25 or greater than 25 of the mutations disclosed herein including but not limited to the mutations disclosed in Tables 1-6 and 8-12, as well as mutations in the corresponding homoeologues.

In another embodiment, a wheat plant, wheat seed or parts of a wheat plant comprising one or more non-transgenic mutations in an SBEII gene, including but not limited to the mutation listed in Tables 1-6 and 8-12 and the mutations in the corresponding homoeologues, has an increased proportion of amylose in starch as compared to the same wheat cultivar without the mutations in the SBEII gene. In yet another embodiment, the proportion of amylose in the starch is selected from the group consisting of at least 10-15%, 16-20%, 21-25%, 26-30%, 31-35%, 36-40%, 41-45%, 46-50%, 51-55%, 56-60%, 61-65%, 66-70%, 71-75%, 76-80%, 81-85%, 86-90%, 91-95%, 96%, 97%, 98%, 99%, and greater than 99% (w/w).

Grain, Flour and Starch

In another embodiment, the invention relates to a wheat grain, flour or starch comprising one or more non-transgenic mutations in the SBEII gene. In another embodiment, the invention relates to wheat grain comprising an embryo, wherein the embryo comprises one or more non-transgenic mutations in an SBEII gene.

In another embodiment, the wheat grain, flour or starch comprises one or more non-transgenic mutations in the SBEIIa and/or the SBEIIb genes including but not limited to the mutations recited in Tables 1-6 and 8-12 and the corresponding mutations in homoeologues.

In still another embodiment, the invention relates to a wheat grain, flour or starch comprising one or more non-transgenic mutations in the SBEIIa gene. In another embodiment, the invention relates to a wheat grain or flour comprising at least one non-transgenic mutation in the SBEIIa gene in each of two genomes. In still another embodiment, the invention relates to a wheat grain or flour comprising at least one non-transgenic mutation in the SBEIIa gene in each of three genomes.

In one embodiment, the wheat grain, flour or starch comprises one or more non-transgenic mutations in both alleles of the SBEIIa gene in the A genome. In another embodiment, the non-transgenic mutations are identical in both alleles of the SBEIIa gene of the A genome.

In one embodiment, the wheat grain, flour or starch comprises one or more non-transgenic mutations in both alleles of the SBEIIa gene in the B genome. In another embodiment, the non-transgenic mutations are identical in both alleles of the SBEIIa gene of the B genome.

In one embodiment, the wheat grain, flour or starch comprises one or more non-transgenic mutations in both alleles of the SBEIIa gene in the D genome. In another embodiment, the non-transgenic mutations are identical in both alleles of the SBEIIa gene of the D genome.

In one embodiment, the invention relates to wheat grain, wheat flour or starch comprising a polynucleotide of the SBEIIa gene in the A genome with one or more non-transgenic mutations listed in Table 1 and corresponding to SEQ ID NO: 1. In another embodiment, the wheat grain or wheat flour comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, wheat grain, wheat flour or starch comprise a polynucleotide with one or more non-transgenic mutations listed in Table 1 that codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 2.

In one embodiment, the invention relates to wheat grain, wheat flour or starch comprising a polynucleotide of the SBEIIa gene in the B genome with one or more non-transgenic mutations listed in Table 2 and corresponding to SEQ ID NO: 3. In another embodiment, the wheat grain or wheat flour comprises a polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical or similar to SEQ ID NO: 3.

In still another embodiment, wheat grain, wheat flour or starch comprise a polynucleotide with one or more non-transgenic mutations listed in Table 2 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 4.

In one embodiment, the invention relates to wheat grain, wheat flour or starch comprising a polynucleotide of the SBEIIa gene of the D genome with one or more non-transgenic mutations listed in Table 3 and corresponding to SEQ ID NO: 5. In another embodiment, the wheat grain or wheat flour comprise a polynucleotide with one or more non-transgenic mutations listed in Table 3 and is 85%, 86%, 87%, 88%, 89%, 90%, 91%, 92%, 93%, 94%, 95%, 96%, 97%, 98%, 99% or greater than 99% identical or similar to SEQ ID NO: 5.

In still another embodiment, wheat grain, wheat flour or starch comprise a polynucleotide with one or more non-transgenic mutations listed in Table 3 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In still another embodiment, the invention relates to a wheat grain, flour or starch comprising one or more non-transgenic mutations in the SBEIIb gene. In another embodiment, the invention relates to a wheat plant comprising at least one non-transgenic mutation in the SBEIIb gene in each of two genomes. In still another embodiment, the invention relates to a wheat plant comprising at least one non-transgenic mutation in the SBEIIb gene in each of three genomes.

In one embodiment, the wheat grain, flour or starch comprises one or more non-transgenic mutations in both alleles of the SBEIIb gene. In one embodiment, the wheat grain, flour or starch comprises one or more non-transgenic mutations in both alleles of the SBEIIb gene in each of two genomes. In one embodiment, the wheat grain, flour or starch comprises one or more non-transgenic mutations in both alleles of the SBEIIb gene in each of three genomes.

In one embodiment, the wheat grain, flour or starch comprises one or more non-transgenic mutations in both alleles of the SBEIIb gene. In one embodiment, the wheat grain, flour or starch comprises one or more non-transgenic mutations in both alleles of the SBEIIb gene of the A genome. In another embodiment, the non-transgenic mutations are identical in both alleles of the SBEIIb gene of the A genome.

In one embodiment, the wheat grain, flour or starch comprises one or more non-transgenic mutations in both alleles of the SBEIIb gene of the B genome. In another embodiment, the non-transgenic mutations are identical in both alleles of the SBEIIb gene of the B genome.

In one embodiment, the wheat grain, flour or starch comprises one or more non-transgenic mutations in both alleles of the SBEIIb gene of the D genome. In another embodiment, the non-transgenic mutations are identical in both alleles of the SBEIIb gene of the D genome.

In one embodiment, the invention relates to a wheat grain, wheat flour or starch comprising a polynucleotide of the SBEIIb gene of the A genome with one or more non-transgenic mutations listed in Table 4 and corresponding to SEQ ID NO: 7. In another embodiment, the wheat grain, wheat flour or starch comprises a polynucleotide with one or more non-transgenic mutations listed in Table 4 and is 85%, 86%, 87%, 88%, 89%, 90%, 91%, 92%, 93%, 94%, 95%, 96%, 97%, 98%, 99% or greater than 99% identical or similar to SEQ ID NO: 7.

In still another embodiment, the wheat grain, wheat flour or starch comprise a polynucleotide with one or more non-transgenic mutations listed in Table 4 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 8.

In one embodiment, the invention relates to wheat grain, wheat flour or starch comprising a polynucleotide of the SBEIIb gene of the B genome with one or more non-transgenic mutations listed in Table 5 and corresponding to SEQ ID NO: 9. In another embodiment, the wheat grain, wheat flour or starch comprise a polynucleotide with one or more non-transgenic mutations listed in Table 5 and is 85%, 86%, 87%, 88%, 89%, 90%, 91%, 92%, 93%, 94%, 95%, 96%, 97%, 98%, 99% or greater than 99% identical or similar to SEQ ID NO: 9.

In still another embodiment, the wheat grain, wheat flour or starch comprise a polynucleotide with one or more non-transgenic mutations listed in Table 5 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 10.

In one embodiment, the invention relates to wheat grain, wheat flour or starch comprising a polynucleotide of the SBEIIb gene of the D genome with one or more non-transgenic mutations listed in Table 6 and corresponding to SEQ ID NO: 11. In another embodiment, the wheat grain, wheat flour or starch comprise a polynucleotide with one or more non-transgenic mutations listed in Table 6 and is 85%, 86%, 87%, 88%, 89%, 90%, 91%, 92%, 93%, 94%, 95%, 96%, 97%, 98%, 99% or greater than 99% identical or similar to SEQ ID NO: 11.

In still another embodiment, the wheat grain, wheat flour or starch comprise a polynucleotide with one or more non-transgenic mutations listed in Table 6 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 12.

In another embodiment, the invention relates to a wheat grain, flour or starch comprising one or more non-transgenic mutations in the SBEIIa gene and one or more non-transgenic mutations in the SBEIIb genes. In another embodiment, the invention relates to a wheat grain, flour or starch comprising at least one non-transgenic mutation in the SBEIIa and SBEIIb genes in each of two genomes. In still another embodiment, the invention relates to a wheat grain, flour or starch comprising at least one non-transgenic mutation in the SBEIIa and SBEIIb genes in each of three genomes.

In still another embodiment, the invention relates to a wheat grain, flour or starch comprising at least one non-transgenic mutation in the SBEIIa gene in each of three genomes and one or more non-transgenic mutation in the SBEIIb gene.

In one embodiment, the wheat grain, flour or starch comprises one or more non-transgenic mutations in both alleles of the SBEIIa gene and the SBEIIb gene of the A genome. In another embodiment, the non-transgenic mutations are identical in both alleles of the SBEIIa gene and the SBEIIb gene of the A genome.

In one embodiment, the wheat grain, flour or starch comprises one or more non-transgenic mutations in both alleles of the SBEIIa gene and the SBEIIb gene of the B genome. In another embodiment, the non-transgenic mutations are identical in both alleles of the SBEIIa gene and the SBEIIb gene of the B genome.

In one embodiment, the wheat grain, flour or starch comprises one or more non-transgenic mutations in both alleles of the SBEIIa gene and the SBEIIb gene of the D genome. In another embodiment, the non-transgenic mutations are identical in both alleles of the SBEIIa gene and the SBEIIb gene of the D genome.

In still another embodiment, the invention relates to wheat grain or flour comprising an endosperm and a reduced gene expression level, activity or expression level and activity of the SBEII gene as compared to wild type wheat grain or flour.

In still another embodiment, the invention relates to wheat grain or flour comprising an endosperm and a reduced expression level, activity or expression level and activity of the SBEII protein as compared to wild type wheat grain or flour. In still another embodiment, the invention relates to wheat grain or flour comprising an endosperm and a reduced expression level, activity or expression level and activity of the SBEIIa protein as compared to wild type wheat grain or flour. In yet another embodiment, the invention relates to wheat grain or flour comprising an endosperm and a reduced expression level, activity or expression level and activity of the SBEIIb protein as compared to wild type wheat grain or flour.

In yet another embodiment, the invention relates to wheat grain or flour comprising an altered starch component as compared to starch from wild type wheat grain or flour. In another embodiment, the wheat grain or flour comprises starch with a percentage of amylose selected from the group consisting of: 25-30%, 30-35%, 35-40%, 45-50%, 50-55%, 55-60%, 60-65%, 65-70%, 70-75%, 75-80%, 80-85%, 85-90%, 90-95%, and greater than 95% as compared to wild type grain or flour.

Food Products

In one embodiment, the invention is directed to a flour or other product produced from the grain or flour discussed above. In another embodiments, the flour, the coarse fraction or purified starch may be a component of a food product.

The food product includes but is not limited to a bagel, a biscuit, a bread, a bun, a croissant, a dumpling, an English muffin, a muffin, a pita bread, a quickbread, a refrigerated/frozen dough products, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In one embodiment, the flour is a whole grain flour (ex.—an ultrafine-milled whole grain flour, such as an ultrafine-milled whole grain wheat flour). In one embodiment, the whole grain flour includes a refined flour constituent (ex.—refined wheat flour or refined flour) and a coarse fraction (ex.—an ultrafine-milled coarse fraction). Refined wheat flour may be flour which is prepared, for example, by grinding and bolting (sifting) cleaned wheat. The Food and Drug Administration (FDA) requires flour to meet certain particle size standards in order to be included in the category of refined wheat flour. The particle size of refined wheat flour is described as flour in which not less than 98% passes through a cloth having openings not larger than those of woven wire cloth designated "212 micrometers (U.S. Wire 70)."

In another embodiment, the coarse fraction includes at least one of: bran and germ. For instance, the germ is an embryonic plant found within the wheat kernel. The germ includes lipids, fiber, vitamins, protein, minerals and phytonutrients, such as flavonoids. The bran may include several cell layers and has a significant amount of lipids, fiber, vitamins, protein, minerals and phytonutrients, such as flavonoids.

For example, the coarse fraction or whole grain flour or refined flour of the present invention may be used in various amounts to replace refined or whole grain flour in baked goods, snack products, and food products. The whole grain flour (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In another embodiment, the whole grain flour or coarse fraction or refined flour may be a component of a nutritional supplement. The nutritional supplement may be a product that is added to the diet containing one or more ingredients, typically including: vitamins, minerals, herbs, amino acids, enzymes, antioxidants, herbs, spices, probiotics, extracts, prebiotics and fiber.

In a further embodiment, the nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. Because of the high nutritional content of the endosperm of the present invention, there may be many uses that confer numerous benefits to an individual, including, delivery of fiber and other essential nutrients, increased digestive function and health, weight management, blood sugar management, heart health, diabetes risk reduction, potential arthritis risk reduction, and overall health and wellness for an individual.

In still another embodiments, the whole grain flour or coarse fraction or refined flour may be a component of a dietary supplement. The Code of Federal Regulations defines a dietary supplement as a product that is intended to supplement the diet and contains one or more dietary ingredients including: vitamins, minerals, herbs, botanicals, amino acids, and other substances or their constituents; is intended to be taken by mouth as a pill, capsule, tablet, or liquid; and is labeled on the front panel as being a dietary supplement.

In yet another embodiment, the whole grain flour or coarse fraction or refined flour may be a fiber supplement or a component thereof. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage.

In another embodiment, the whole grain flour or coarse fraction or refined flour may be included as a component of a digestive supplement. The whole grain flour or coarse fraction or refined flour may be a component of a digestive supplement alone or in combination with one or more prebiotic compounds and/or probiotic organisms. Prebiotic compounds are non-digestible food ingredients that may beneficially affect the host by selectively stimulating the growth and/or the activity of a limited number of microorganisms in the colon. Examples of prebiotic compounds within the scope of the invention, may include, but are not limited to: oligosaccharides and inulins.

Probiotics are microorganisms which, when administered in adequate amounts, confer a health benefit on the host. Probiotic organisms include, but are not limited to: *Lactobacillus, Bifidobacteria, Escherichia, Clostridium, Lactococcus, Streptococcus, Enterococcus*, and *Saccharomyces*.

In yet another embodiment, the whole grain flour or coarse fraction or refined flour may be included as a component of a functional food. The Institute of Food Technologists defines functional foods as, foods and food components that provide a health benefit beyond basic nutrition. This includes conventional foods, fortified, enriched, or enhanced foods, and dietary supplements. The whole grain flour and coarse fraction or refined flour include numerous vitamins and minerals, have high oxygen radical absorption capacities, and are high in fiber, making them ideally suited for use in/as a functional food.

In another embodiment, the whole grain flour or coarse fraction or refined flour may be used in medical foods. Medical food is defined as a food that is formulated to be consumed or administered entirely under the supervision of a physician and which is intended for the specific dietary management of a disease or condition for which distinctive nutritional requirements, based on recognized scientific principles, are established by medical evaluation. The nutrient contents and antioxidant capacities of the whole grain flour and coarse fraction or refined flour make them ideal for use in medical foods.

In yet another embodiment, the whole grain flour or coarse fraction or refined flour may also be used in pharmaceuticals. The whole grain flour and coarse fraction or refined flour are high in fiber and have a very fine granulation making them suitable for use as a carrier in pharmaceuticals.

In still another embodiment, delivery of the whole grain flour or coarse fraction or refined flour as a nutritional supplement, dietary supplement or digestive supplement is contemplated via delivery mechanisms where the whole grain flour or coarse fraction is the single ingredient or one of many nutritional ingredients. Examples of delivery mechanisms include but are not limited to: instant beverage mixes, ready-to-drink beverages, nutritional bars, wafers, cookies, crackers, gel shots, capsules, and chews.

In yet another embodiment, a milling process may be used to make a multi-wheat flour, or a multi-grain coarse fraction. In one embodiment, bran and germ from one type of wheat may be ground and blended with ground endosperm or whole grain wheat flour of another type of wheat. Alternatively bran and germ of one type of grain may be ground and blended with ground endosperm or whole grain flour of another type of grain.

In still another embodiment, bran and germ from a first type of wheat or grain may be blended with bran and germ from a second type of wheat or grain to produce a multi-grain coarse fraction. It is contemplated that the invention encompasses mixing any combination of one or more of bran, germ, endosperm, and whole grain flour of one or more grains. This multi-grain, multi-wheat approach may be used to make custom flour and capitalize on the qualities and nutritional contents of multiple types of grains or wheats to make one flour.

The whole grain flour of the invention may be produced via a variety of milling processes. One exemplary process involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like.

After grinding, the grain is discharged and conveyed to a sifter. Any sifter known in the art for sifting a ground particle may be used. Material passing through the screen of the sifter is the whole grain flour of the invention and requires no further processing. Material that remains on the screen is referred to as a second fraction. The second fraction requires additional particle reduction. Thus, this second fraction may be conveyed to a second passage grinder.

After grinding, the second fraction may be conveyed to a second sifter. Material passing through the screen of the second sifter is the whole grain flour. The material that remains on the screen is referred to as the fourth fraction and requires further processing to reduce the particle size. The fourth fraction on the screen of the second sifter is conveyed back into either the first passage grinder or the second passage grinder for further processing via a feedback loop.

It is contemplated that the whole grain flour, coarse fraction, purified starch and/or grain products of the invention may be produced by a number of milling processes known in the art.

Plant Breeding

In another embodiment, this invention is directed to methods for plant breeding using wheat plants and plant parts with one or more non-transgenic mutations in the SBEII gene. One such embodiment is the method of crossing wheat variety with one or more non-transgenic mutations in the SBEII gene with another variety of wheat to form a first generation population of F1 plants. The population of first generation F1 plants produced by this method is also an embodiment of the invention. This first generation population of F1 plants will comprise an essentially complete set of the alleles of wheat variety with one or more non-transgenic mutations in the SBEII gene. One of ordinary skill in the art can utilize either breeder books or molecular methods to identify a particular F1 plant produced using wheat variety with one or more non-transgenic mutations in the SBEII gene, and any such individual plant is also encompassed by this invention. These embodiments also cover use of transgenic or backcross conversions of wheat varieties with one or more mutations in the SBEII gene to produce first generation F1 plants.

In another embodiment, the invention relates to a method of developing a progeny wheat plant. A method of developing a progeny wheat plant comprises crossing a wheat variety with one or more non-transgenic mutations in the SBEII gene with a second wheat plant and performing a breeding method. A specific method for producing a line derived from wheat variety with one or more non-transgenic mutations in the SBEII gene is as follows.

One of ordinary skill in the art would cross wheat variety with one or more non-transgenic mutations in the SBEII gene with another variety of wheat, such as an elite variety. The F1 seed derived from this cross would be grown to form a homogeneous population. The F1 seed would contain one set of the alleles from wheat variety with one or more non-transgenic mutations in the SBEII gene and one set of the alleles from the other wheat variety.

The F1 genome would be made-up of 50% wheat variety with one or more non-transgenic mutations in the SBEII gene and 50% of the other elite variety. The F1 seed would be grown to form F2 seed. The F1 seed could be allowed to self, or bred with another wheat cultivar.

On average the F2 seed would have derived 50% of its alleles from wheat variety with one or more non-transgenic mutations in the SBEII gene and 50% from the other wheat variety, but various individual plants from the population would have a much greater percentage of their alleles derived from wheat variety with one or more non-transgenic mutations in the SBEII gene (Wang J. and R. Bernardo, 2000, Crop Sci. 40:659-665 and Bernardo, R. and A. L. Kahler, 2001, Theor. Appl. Genet. 102:986-992).

The F2 seed would be grown and selection of plants would be made based on visual observation and/or measurement of traits and/or marker assisted selection. The wheat variety with one or more non-transgenic mutations in the SBEII gene-derived progeny that exhibit one or more of the desired wheat variety with one or more non-transgenic mutations in the SBEII gene-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable wheat variety with one or more non-transgenic mutations in the SBEII gene-derived traits.

The process of growing and selection would be repeated any number of times until a homozygous wheat variety with one or more non-transgenic mutations in the SBEII gene-derived wheat plant is obtained. The homozygous wheat variety with one or more non-transgenic mutations in the SBEII gene-derived wheat plant would contain desirable traits derived from wheat variety with one or more non-transgenic mutations in the SBEII gene, some of which may not have been expressed by the other original wheat variety to which wheat variety with one or more non-transgenic mutations in the SBEII gene was crossed and some of which may have been expressed by both wheat varieties but now would be at a level equal to or greater than the level expressed in wheat variety with one or more non-transgenic mutations in the SBEII gene.

The breeding process, of crossing, selfing, and selection may be repeated to produce another population of wheat variety with one or more non-transgenic mutations in the SBEII gene-derived wheat plants with, on average, 25% of their genes derived from wheat variety with one or more non-transgenic mutations in the SBEII gene, but various individual plants from the population would have a much greater percentage of their alleles derived from wheat variety with one or more non-transgenic mutations in the SBEII gene. Another embodiment of the invention is a homozygous wheat variety with one or more non-transgenic mutations in the SBEII gene-derived wheat plant that has received wheat variety with one or more non-transgenic mutations in the SBEII gene-derived traits.

The invention is further described by the following paragraphs.

1. A polynucleotide encoding an SBEIIa polypeptide comprising a tryptophan to a stop mutation at an amino acid corresponding to amino acid position 436 of SEQ ID NO: 2.

2. The polynucleotide of paragraph 1, wherein the SBEIIa polypeptide further comprises an amino acid sequence having at least 95% identity or similarity to SEQ ID NO: 2.

3. The polynucleotide of any of paragraphs 1-2, wherein the SBEIIa polypeptide further comprises an amino acid sequence having at least 97% identity or similarity to SEQ ID NO: 2.

4. The polynucleotide of any of paragraphs 1-3, wherein the SBEIIa polypeptide further comprises an amino acid sequence having at least 99% identity or similarity to SEQ ID NO: 2.

5. The polynucleotide of any of paragraphs 1-4 comprising a guanine to adenine mutation at a nucleotide position corresponding to nucleotide position 5267 of SEQ ID NO: 1.

6. The polynucleotide of any of paragraphs 1-5 further comprising at least 95% identity or similarity to SEQ ID NO: 1.

7. The polynucleotide of any of paragraphs 1-6 further comprising at least 97% identity or similarity to SEQ ID NO: 1.

8. The polynucleotide o any of paragraphs 1-7 further comprising at least 99% identity or similarity to SEQ ID NO: 1.

9. A polypeptide comprising an amino acid sequence having at least 95% identity or similarity to SEQ ID NO:2, wherein the polypeptide further comprises a tryptophan to a stop mutation at amino acid position 436 of SEQ ID NO: 2.

10. The polypeptide of paragraph 9 further comprising an amino acid sequence having at least 97% sequence identity or similarity to SEQ ID NO:2.

11. The polypeptide of any of paragraphs 9-10 further comprising an amino acid sequence having at least 99% sequence identity or similarity to SEQ ID NO:2.

12. The polypeptide of any of paragraphs 9-11 further comprising an amino acid sequence of SEQ ID NO:2 with a tryptophan to a stop mutation at amino acid position 436 or a fragment thereof having starch branching enzyme activity.

13. The polypeptide of any of paragraphs 1-12 further comprising an amino acid sequence of SEQ ID NO:2 with a tryptophan to a stop mutation at amino acid position 436.

14. A polynucleotide encoding an SBEIIa polypeptide comprising a tryptophan to a stop mutation at an amino acid corresponding to amino acid position 436 of SEQ ID NO: 4.

15. The polynucleotide of paragraph 14, wherein the SBEIIa polypeptide further comprises an amino acid sequence having at least 95% identity or similarity to SEQ ID NO: 4.

16. The polynucleotide of any of paragraphs 14-15, wherein the SBEIIa polypeptide further comprises an amino acid sequence having at least 97% identity or similarity to SEQ ID NO: 4.

17. The polynucleotide of any of paragraphs 14-16, wherein the SBEIIa polypeptide further comprises an amino acid sequence having at least 99% identity or similarity to SEQ ID NO: 4.

18. The polynucleotide of any of paragraphs 14-17 comprising a guanine to adenine mutation at a nucleotide position corresponding to nucleotide position 5038 of SEQ ID NO: 3.

19. The polynucleotide of any of paragraphs 14-18 further comprising at least 95% identity or similarity to SEQ ID NO: 3.

20. The polynucleotide of any of paragraphs 14-19 further comprising at least 97% identity or similarity to SEQ ID NO: 3.

21. The polynucleotide of any of paragraphs 14-20 further comprising at least 99% identity or similarity to SEQ ID NO: 3.

22. A polypeptide comprising an amino acid sequence having at least 95% identity or similarity to SEQ ID NO:4, wherein the polypeptide further comprises a tryptophan to a stop mutation at amino acid position 436 of SEQ ID NO: 4.

23. The polypeptide of paragraph 22 further comprising an amino acid sequence having at least 97% sequence identity or similarity to SEQ ID NO:4.

24. The polypeptide of any of paragraphs 22-23 further comprising an amino acid sequence having at least 99% sequence identity or similarity to SEQ ID NO:4.

25. The polypeptide of any of paragraphs 22-24 comprising an amino acid sequence of SEQ ID NO:4 with a tryptophan to a stop mutation at amino acid position 436 or a fragment thereof having starch branching enzyme activity.

26. The polypeptide of any of paragraphs 22-25 comprising an amino acid sequence of SEQ ID NO:4 with a tryptophan to a stop mutation at amino acid position 436.

27. A polynucleotide encoding an SBEIIa polypeptide comprising a tryptophan to a stop mutation at an amino acid corresponding to amino acid position 432 of SEQ ID NO: 6.

28. The polynucleotide of paragraph 27, wherein the SBEIIa polypeptide further comprises an amino acid sequence having at least 95% identity or similarity to SEQ ID NO: 6.

29. The polynucleotide of any of paragraphs 27-28, wherein the SBEIIa polypeptide further comprises an amino acid sequence having at least 97% identity or similarity to SEQ ID NO: 6.

30. The polynucleotide of any of paragraphs 27-29, wherein the SBEIIa polypeptide further comprises an amino acid sequence having at least 99% identity or similarity to SEQ ID NO: 6.

31. The polynucleotide of any of paragraphs 27-30 comprising a guanine to adenine mutation at a nucleotide position corresponding to nucleotide position 6305 of SEQ ID NO: 5.

32. The polynucleotide of any of paragraphs 27-31 further comprising at least 95% identity or similarity to SEQ ID NO: 5.

33. The polynucleotide of any of paragraphs 27-32 further comprising at least 97% identity or similarity to SEQ ID NO: 5.

34. The polynucleotide of any of paragraphs 27-33 further comprising at least 99% identity or similarity to SEQ ID NO: 5.

35. A polypeptide comprising an amino acid sequence having at least 95% identity or similarity to SEQ ID NO:6, wherein the polypeptide further comprises a tryptophan to a stop mutation at amino acid position 432 of SEQ ID NO: 6.

36. The polypeptide of paragraph 35 further comprising an amino acid sequence having at least 97% sequence identity or similarity to SEQ ID NO:6.

37. The polypeptide of any of paragraphs 35-36 further comprising an amino acid sequence having at least 99% sequence identity or similarity to SEQ ID NO:6.

38. The polypeptide of any of paragraphs 35-37 comprising an amino acid sequence of SEQ ID NO:6 with a tryptophan to a stop mutation at amino acid position 432 or a fragment thereof having starch branching enzyme activity.

39. The polypeptide of any of paragraphs 35-38 comprising an amino acid sequence of SEQ ID NO:6 with a tryptophan to a stop mutation at amino acid position 432.

40. A polynucleotide encoding an SBEIIa polypeptide comprising a tryptophan to a stop mutation at an amino acid corresponding to amino acid position 446 of SEQ ID NO: 4.

41. The polynucleotide of paragraph 40, wherein the SBEIIa polypeptide further comprises an amino acid sequence having at least 95% identity or similarity to SEQ ID NO: 4.

42. The polynucleotide of any of paragraphs 40-41, wherein the SBEIIa polypeptide further comprises an amino acid sequence having at least 97% identity or similarity to SEQ ID NO: 4.

43. The polynucleotide of any of paragraphs 40-42, wherein the SBEIIa polypeptide further comprises an amino acid sequence having at least 99% identity or similarity to SEQ ID NO: 4.

44. The polynucleotide of any of paragraphs 40-43 comprising a guanine to adenine mutation at a nucleotide position corresponding to nucleotide position 5069 of SEQ ID NO: 3.

45. The polynucleotide of any of paragraphs 40-44 further comprising at least 95% identity or similarity to SEQ ID NO: 3.

46. The polynucleotide of any of paragraphs 40-45 further comprising at least 97% identity or similarity to SEQ ID NO: 3.

47. The polynucleotide of any of paragraphs 40-46 further comprising at least 99% identity or similarity to SEQ ID NO: 3.

48. A polypeptide comprising an amino acid sequence having at least 95% identity or similarity to SEQ ID NO:4, wherein the polypeptide further comprises a tryptophan to a stop mutation at amino acid position 446 of SEQ ID NO: 4.

49. The polypeptide of paragraph 48 further comprising an amino acid sequence having at least 97% sequence identity or similarity to SEQ ID NO:4.

50. The polypeptide of paragraphs 48-49 further comprising an amino acid sequence having at least 99% sequence identity or similarity to SEQ ID NO:4.

51. The polypeptide of any of paragraphs 48-50 comprising an amino acid sequence of SEQ ID NO:4 with a tryptophan to a stop mutation at amino acid position 446 or a fragment thereof having starch branching enzyme activity.

52. The polypeptide of any of paragraphs 48-51 comprising an amino acid sequence of SEQ ID NO:4 with a tryptophan to a stop mutation at amino acid position 446.

53. An SBEIIa polynucleotide comprising a guanine to adenine mutation at a nucleotide position corresponding to nucleotide position 5073 of SEQ ID NO: 3.

54. The polynucleotide of paragraph 53 further comprising at least 95% identity or similarity to SEQ ID NO: 3.

55. The polynucleotide of any of paragraph 53-54 further comprising at least 97% identity or similarity to SEQ ID NO: 3.

56. The polynucleotide of any of paragraphs 53-55 further comprising at least 99% identity or similarity to SEQ ID NO: 3.

57. A polynucleotide encoding an SBEIIa polypeptide comprising a glycine to a glutamate mutation at an amino acid corresponding to amino acid position 467 of SEQ ID NO: 4.

58. The polynucleotide of paragraph 57, wherein the SBEIIa polypeptide further comprises an amino acid sequence having at least 95% identity or similarity to SEQ ID NO: 4.

59. The polynucleotide of any of paragraphs 57-58, wherein the SBEIIa polypeptide further comprises an amino acid sequence having at least 97% identity or similarity to SEQ ID NO: 4.

60. The polynucleotide of any of paragraphs 57-59, wherein the SBEIIa polypeptide further comprises an amino acid sequence having at least 99% identity or similarity to SEQ ID NO: 4.

61. The polynucleotide of any of paragraphs 57-60 comprising a guanine to adenine mutation at a nucleotide position corresponding to nucleotide position 5219 of SEQ ID NO: 3.

62. The polynucleotide of any of paragraphs 57-61 further comprising at least 95% identity or similarity to SEQ ID NO: 3.

63. The polynucleotide of any of paragraphs 57-62 further comprising at least 97% identity or similarity to SEQ ID NO: 3.

64. The polynucleotide of any of paragraphs 57-63 further comprising at least 99% identity or similarity to SEQ ID NO: 3.

65. A polypeptide comprising an amino acid sequence having at least 95% identity or similarity to SEQ ID NO:4, wherein the polypeptide further comprises a glycine to a glutamate mutation at amino acid position 467 of SEQ ID NO: 4.

66. The polypeptide of paragraph 65 further comprising an amino acid sequence having at least 97% sequence identity or similarity to SEQ ID NO:4.

67. The polypeptide of any of paragraphs 65-66 further comprising an amino acid sequence having at least 99% sequence identity or similarity to SEQ ID NO:4.

68. The polypeptide of any of paragraphs 65-67 comprising an amino acid sequence of SEQ ID NO:4 with a glycine to a glutamate mutation at amino acid position 467 or a fragment thereof having starch branching enzyme activity.

69. The polypeptide of any of paragraphs 65-68 comprising an amino acid sequence of SEQ ID NO:4 with a glycine to a glutamate mutation at amino acid position 467.

70. A polynucleotide encoding an SBEIIa polypeptide comprising a tryptophan to a stop mutation at an amino acid corresponding to amino acid position 442 of SEQ ID NO: 6.

71. The polynucleotide of paragraph 70, wherein the SBEIIa polypeptide further comprises an amino acid sequence having at least 95% identity or similarity to SEQ ID NO: 6.

72. The polynucleotide of any of paragraphs 70-71, wherein the SBEIIa polypeptide further comprises an amino acid sequence having at least 97% identity or similarity to SEQ ID NO: 6.

73. The polynucleotide of any of paragraphs 70-72, wherein the SBEIIa polypeptide further comprises an amino acid sequence having at least 99% identity or similarity to SEQ ID NO: 6.

74. The polynucleotide of any of paragraphs 70-73 comprising a guanine to adenine mutation at a nucleotide position corresponding to nucleotide position 6335 of SEQ ID NO: 5.

75. The polynucleotide of any of paragraphs 70-74 further comprising at least 95% identity or similarity to SEQ ID NO: 5.

76. The polynucleotide of any of paragraphs 70-75 further comprising at least 97% identity or similarity to SEQ ID NO: 5.

77. The polynucleotide of any of paragraphs 70-76 further comprising at least 99% identity or similarity to SEQ ID NO: 5.

78. A polypeptide comprising an amino acid sequence having at least 95% identity or similarity to SEQ ID NO:6, wherein the polypeptide further comprises a tryptophan to a stop mutation at amino acid position 442 of SEQ ID NO: 6.

79. The polypeptide of paragraph 78 further comprising an amino acid sequence having at least 97% sequence identity or similarity to SEQ ID NO:6.

80. The polypeptide of any of paragraphs 78-79 further comprising an amino acid sequence having at least 99% sequence identity or similarity to SEQ ID NO:6.

81. The polypeptide of any of paragraphs 78-80 further comprising an amino acid sequence of SEQ ID NO:6 with a tryptophan to a stop mutation at amino acid position 442 or a fragment thereof having starch branching enzyme activity.

82. The polypeptide of any of paragraphs 78-81 comprising an amino acid sequence of SEQ ID NO:6 with a tryptophan to a stop mutation at amino acid position 442.

83. A polynucleotide encoding an SBEIIb polypeptide comprising a tryptophan to a stop mutation at an amino acid corresponding to amino acid position 285 of SEQ ID NO: 8.

84. The polynucleotide of paragraph 83, wherein the SBEIIb polypeptide further comprises an amino acid sequence having at least 95% identity or similarity to SEQ ID NO: 8.

85. The polynucleotide of any of paragraphs 83-84, wherein the SBEIIb polypeptide further comprises an amino acid sequence having at least 97% identity or similarity to SEQ ID NO: 8.

86. The polynucleotide of any of paragraphs 83-85, wherein the SBEIIb polypeptide further comprises an amino acid sequence having at least 99% identity or similarity to SEQ ID NO: 8.

87. The polynucleotide of any of paragraphs 83-86 comprising a guanine to adenine mutation at a nucleotide position corresponding to nucleotide position 2282 of SEQ ID NO: 7.

88. The polynucleotide of any of paragraphs 83-87 further comprising at least 95% identity or similarity to SEQ ID NO: 7.

89. The polynucleotide of any of paragraphs 83-88 further comprising at least 97% identity or similarity to SEQ ID NO: 7.

90. The polynucleotide of any of paragraphs 83-89 further comprising at least 99% identity or similarity to SEQ ID NO: 7.

91. A polypeptide comprising an amino acid sequence having at least 95% identity or similarity to SEQ ID NO:8, wherein the polypeptide further comprises a tryptophan to a stop mutation at amino acid position 285 of SEQ ID NO: 8.

92. The polypeptide of paragraph 91 further comprising an amino acid sequence having at least 97% sequence identity or similarity to SEQ ID NO:8.

93. The polypeptide of any of paragraphs 91-92 further comprising an amino acid sequence having at least 99% sequence identity or similarity to SEQ ID NO:8.

94. The polypeptide of any of paragraphs 91-93 further comprising an amino acid sequence of SEQ ID NO:8 with a tryptophan to a stop mutation at amino acid position 285 or a fragment thereof having starch branching enzyme activity.

95. The polypeptide of any of paragraphs 91-94 comprising an amino acid sequence of SEQ ID NO:8 with a tryptophan to a stop mutation at amino acid position 285.

96. A wheat plant comprising a polynucleotide of any of paragraphs 1-8, 14-21, 27-34, 40-47, 53-56, 57-64, 70-77, and 83-90.

97. A wheat plant comprising at least two non-transgenic mutations in an SBEII gene, wherein at least one mutation is in the SBEIIa gene as recited in any of paragraphs 1-8, 14-21, 27-34, 40-47, 53-56, 57-64, and 70-77.

98. The wheat plant of any of paragraphs 96-97, wherein a second non-transgenic mutation is in the SBEIIb gene. The SBEIIb mutations may be as recited in paragraphs 83-90.

99. The wheat plant of any of paragraphs 96-98, wherein the first and second mutations are in the SBEIIa gene.

100. The wheat plant of any of paragraphs 96-99, wherein the first and second mutations are in the same genome.

101. The wheat plant of any of paragraphs 96-100, wherein the first and second mutations are in different genomes.

102. The wheat plant of any of paragraphs 96-101, further comprising at least three non-transgenic mutations in the SBEII gene.

103. The wheat plant of any of paragraphs 96-102, wherein two mutations are in the same genome.

104. The wheat plant of any of paragraphs 96-103, wherein three mutations are in different genomes.

105. The wheat plant of any of paragraphs 96-104, wherein the three mutations are in each of the A genome, B genome and D genome. Any number of mutations are possible including 1, 2, 3, 4, 5, 6, 7, 8, 9, 10, and greater than 10 mutations in the SBEIIa gene and including 1, 2, 3, 4, 5, 6, 7, 8, 9, 10, and greater than 10 mutations in the SBEIIb gene.

106. A wheat plant comprising at least two polynucleotides as recited in any of paragraphs 1-8, 14-21, 27-34, 40-47, 53-56, 57-64, 70-77, and 83-90

107. A wheat plant comprising a polypeptide of any of paragraphs 9-13, 22-26, 35-39, 48-52, 65-69, 78-82, and 91-95.

108. The wheat plant of any of paragraphs 96-107, wherein the wheat is diploid, tetraploid or hexaploid.

109. A hexaploid wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

110. A hexaploid wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

111. A hexaploid wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5. 112. A wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

113. A wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

114. A wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

115. A wheat seed comprising a polynucleotide of any of paragraphs 1-8, 14-21, 27-34, 40-47, 53-56, 57-64, 70-77, and 83-90.

116. A wheat seed comprising at least two non-transgenic mutations in an SBEII gene, wherein at least one mutation is in the SBEIIa gene as recited in any of paragraphs 1-8, 14-21, 27-34, 40-47, 53-56, 57-64, 70-77, and 83-90.

117. The wheat seed of any of paragraphs 115-115, wherein a second non-transgenic mutation is in the SBEIIb gene.

118. The wheat seed of any of paragraphs 115-117, wherein the first and second mutations are in the SBEIIa gene.

119. The wheat seed of any of paragraphs 115-118, wherein the first and second mutations are in the same genome.

120. The wheat seed of any of paragraphs 115-119, wherein the first and second mutations are in different genomes.

121. The wheat seed of any of paragraphs 115-120 further comprising at least three non-transgenic mutations in the SBEII gene.

122. The wheat seed of any of paragraphs 115-121, wherein three mutations are in the same genome.

123. The wheat seed of any of paragraphs 115-122, wherein three mutations are in different genomes.

124. The wheat seed of any of paragraphs 115-123, wherein the three mutations are in each of the A genome, B genome and D genome.

125. A wheat seed comprising at least two polynucleotides as recited in any of paragraphs 1-8, 14-21, 27-34, 40-47, 53-56, 57-64, 70-77, and 83-90.

126. A wheat seed comprising a polypeptide of any of paragraphs 9-13, 22-26, 35-39, 48-52, 65-69, 78-82, and 91-95.

127. The wheat seed of any of paragraphs 115-126, wherein the wheat is diploid, tetraploid or hexaploid.

128. A hexaploid wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

129. A hexaploid wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

130. A hexaploid wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5.

131. A wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

132. A wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

133. A wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

134. Wheat grain comprising a polynucleotide of any of paragraphs 1-8, 14-21, 27-34, 40-47, 53-56, 57-64, 70-77, and 83-90.

135. Wheat grain comprising at least two non-transgenic mutations in an SBEII gene, wherein one mutation is in the SBEIIa gene as recited in any of paragraphs 1-8, 14-21, 27-34, 40-47, 53-56, 57-64, 70-77, and 83-90.

136. The wheat grain of any of paragraphs 134-135, wherein a second non-transgenic mutation is in the SBEIIb gene.

137. The wheat grain of any of paragraphs 134-136, wherein the first and second mutations are in the SBEIIa gene.

138. The wheat grain of any of paragraphs 134-137, wherein the first and second mutations are in the same genome.

139. The wheat grain of any of paragraphs 134-138, wherein the first and second mutations are in different genomes.

140. The wheat grain of any of paragraphs 134-139, further comprising at least three non-transgenic mutations in the SBEII gene.

141 The wheat grain of any of paragraphs 134-140, wherein the three mutations are in the same genome.

142. The wheat grain of any of paragraphs 134-141, wherein the three mutations are in different genomes.

143. The wheat grain of any of paragraphs 134-142, wherein the three mutations are in each of the A genome, B genome and D genome.

144. Wheat grain comprising at least two polynucleotides as recited in any of paragraphs 1-8, 14-21, 27-34, 40-47, 53-56, 57-64, 70-77, and 83-90.

145. Wheat grain comprising a polypeptide of any of paragraphs 9-13, 22-26, 35-39, 48-52, 65-69, 78-82, and 91-95.

146. Wheat grain of any of paragraphs 134-145, wherein the wheat is diploid, tetraploid or hexaploid.

147. A hexaploid wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

148. A hexaploid wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

149. A hexaploid wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5.

150. A wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

151. A wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

152. A wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

153. Wheat flour comprising a polynucleotide of any of paragraphs 1-8, 14-21, 27-34, 40-47, 53-56, 57-64, 70-77, and 83-90.

154. Wheat flour comprising at least two non-transgenic mutations in an SBEII gene, wherein one mutation is in the SBEIIa gene as recited in any of paragraphs 1-8, 14-21, 27-34, 40-47, 53-56, 57-64, 70-77, and 83-90.

155. The wheat flour of any of paragraphs 153-154, wherein a second non-transgenic mutation is in the SBEIIb gene.

156. The wheat flour of any of paragraphs 153-155, wherein the first and second mutations are in the SBEIIa gene.

157. The wheat flour of any of paragraphs 153-156, wherein the first and second mutations are in the same genome.

158. The wheat flour of any of paragraphs 153-157, wherein the first and second mutations are in different genomes.

159. The wheat flour of any of paragraphs 153-158, further comprising at least three non-transgenic mutations in the SBEII gene.

160. The wheat flour of any of paragraphs 153-159, wherein the three mutations are in the same genome.

161. The wheat flour of any of paragraphs 153-160, wherein the three mutations are in different genomes.

162. The wheat flour of any of paragraphs 153-161, wherein the three mutations are in each of the A genome, B genome and D genome.

163. Wheat flour comprising at least two polynucleotides as recited in any of paragraphs 1-8, 14-21, 27-34, 40-47, 53-56, 57-64, 70-77, and 83-90.

164. Wheat flour comprising a polypeptide of any of paragraphs 9-13, 22-26, 35-39, 48-52, 65-69, 78-82, and 91-95.

165. Wheat flour of any of paragraphs 153-164, wherein the wheat is diploid, tetraploid or hexaploid.

166. A hexaploid wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

167. A hexaploid wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

168. A hexaploid wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5.

169. A wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

170. A wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

171. A wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

172. A food product comprising the wheat grain of any of paragraphs 134-152.

173. A food product comprising the wheat flour of any of paragraphs 153-171.

174. Use of a polynucleotide according to any of paragraphs 1-8, 14-21, 27-34, 40-47, 53-56, 57-64, 70-77, and 83-90 for the production of wheat having increased amylose levels compared to wild type wheat, wherein said polynucleotide contributes to the increased amylose levels.

175. Use of a polynucleotide according to any of paragraphs 1-8, 14-21, 27-34, 40-47, 53-56, 57-64, 70-77, and 83-90 for the selection of wheat having increased amylose levels compared to wild type wheat, wherein genomic DNA is isolated from the wheat and a segment of said SBEII gene is amplified and the presence of said gene is detected.

176. Use of a polypeptide according to any of paragraphs 9-13, 22-26, 35-39, 48-52, 65-69, 78-82, and 91-95 for the production of wheat having increased amylose levels compared to wild type wheat, wherein said polynucleotide contributes to the increased amylose levels.

177. Use of a polypeptide according to any of paragraphs 9-13, 22-26, 35-39, 48-52, 65-69, 78-82, and 91-95 for the selection of wheat having increased amylose levels compared to wild type wheat, wherein genomic DNA is isolated from the wheat and a segment of said SBEII gene is amplified and the presence of said gene is detected.

EXAMPLE 1

Mutagenesis

In accordance with one exemplary embodiment of the present invention, wheat seeds of the hexaploid cultivar (*Triticum aestivum*) Express and of the tetraploid cultivar (*Triticum turgidum*, Durum) Kronos were vacuum infiltrated in $H_2O$ (approximately 1,000 seeds/100 ml $H_2O$ for approximately 4 minutes). The seeds were then placed on a shaker (45 rpm) in a fume hood at room temperature. The mutagen ethyl methanesulfonate (EMS) was added to the imbibing seeds to final concentrations ranging from about 0.75% to about 1.2% (v/v). Following an 18-hour incubation period, the EMS solution was replaced 4 times with fresh $H_2O$. The seeds were then rinsed under running water for about 4-8 hours. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from the M2 plants produced in accordance with the above description was extracted and prepared in order to identify which M2 plants carried a mutation at one or more of their SBEII loci. The M2 plant DNA was prepared using the methods and reagents contained in the Qiagen® (Valencia, CA) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next, 400 µl of solution AP1 [Buffer AP1, solution DX and RNAse (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5,600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5,600×g. Next, 800 µl of Buffer AW was added to each well of the filter plate, sealed and spun for 15 minutes at 5,600×g in the square well block. The filter plate was then placed on a new set of sample tubes and 80 µl of Buffer AE was applied to the filter. It was capped and incubated at room temperature for 1 minute and then spun for 2 minutes at 5600×g. This step was repeated with an additional 80 µl Buffer AE.

The filter plate was removed and the tubes containing the pooled filtrates were capped. The individual samples were then normalized to a DNA concentration of 5 to 10 ng/μl.

Tilling

The M2 DNA was pooled into groups of two individual plants. The DNA concentration for each individual within the pool was approximately 0.8 ng/μl with a final concentration of 1.6 ng/μl for the entire pool. Then, 5 μl of the pooled DNA samples (or 8 ng wheat DNA) was arrayed on microtiter plates and subjected to gene-specific PCR.

PCR amplification was performed in 15 μl volumes containing 2.5 ng pooled DNA, 0.75×ExTaq buffer (Panvera, Madison, WI), 2.6 mM MgCl$_2$, 0.3 mM dNTPs, 0.3 μM primers, and 0.05U Ex-Taq (Panvera) DNA polymerase. PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63-61° C. for 30 seconds, ramp 0.5° C./sec to 72° C., 72° C. for 1 minute; 72° C. for 8 minutes; 98° C. for 8 minutes; 80° C. for 20 seconds; 60 cycles of 80° C. for 7 seconds −0.3 degrees/cycle.

The PCR primers (MWG Biotech, Inc., High Point, NC) were mixed as follows:

2.5 μl 100 μM IRD-700 labeled left primer
7.5 μl 100 μM left primer
9.0 μl 100 μM IRD-800 labeled right primer
1.0 μl 100 μM right primer A label can be attached to each primer as described or to only one of the primers. Alternatively, Cy5.5 modified primers could be used. The label was coupled to the oligonucleotide using conventional phosphoramidite chemistry.

PCR products (15 μl) were digested in 96-well plates. Next, 30 μl of a solution containing 10 mM HEPES [4-(2-hydroxyethyl)-1-piperazineethanesulfonic acid] (pH 7.5), 10 mM MgSO$_4$, 0.002% (w/v) Triton® X-100, 20 ng/ml of bovine serum albumin, and Surveyor® endonuclease (Transgenomic, Inc.; 1:100,000 dilution) was added with mixing on ice, and the plate was incubated at 45° C. for 15 minutes. The specific activity of the Surveyor enzyme was 800 units/μl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 μl of a 2.5 M NaCl solution with 0.5 mg/ml blue dextran and 75 mM EDTA, followed by the addition of 80 μl isopropanol. The reactions were precipitated at room temperature, spun at 4,000 rpm for 30 minutes in an Eppendorf Centrifuge 5810. Pellets were resuspended in 8 μl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), electrophoresed for 10 min, and removed. Electrophoresis was continued for 4 hours at 1,500-V, 40-W, and 40-mA limits at 50° C.

During electrophoresis, the gel was imaged using a LI-COR® (Lincoln, NE) scanner which was set at a channel capable of detecting the IR Dye 700 and 800 labels. The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products. Plants carrying mutations confirmed by sequencing were grown up as described above (e.g., the M2 plant could be backcrossed or outcrossed twice in order to eliminate background mutations and self-pollinated in order to create a plant that was homozygous for the mutation) or crossed to another plant containing SBEII mutations in a different homoeolog.

Plants that were identified with severe mutations in SBEIIa of the A, B, or D genome were crossed with other plants that contained severe mutations in SBEIIa in other genomes. Severe mutations included those mutations that were predicted to have a deleterious effect on protein function by their SIFT and PSSM, as well as those mutations that resulted in the introduction of a stop codon (truncation mutation) or a mutation at a splice junction. Table 8 shows examples of crosses that were made.

With regard to Tables 8-12, nucleic acid designations of the mutations in SBEIIa of the A genome correspond to the position in the reference sequence SEQ ID NO: 1. Amino acid designations of the SBEIIa polypeptide of the A genome correspond to the amino acid position of reference sequence SEQ ID NO: 2. Nucleic acid designations of the mutations in SBEIIa of the B genome correspond to the position in the reference sequence SEQ ID NO: 3. Amino acid designations of the SBEIIa polypeptide of the B genome correspond to the amino acid position of reference sequence SEQ ID NO: 4. Nucleic acid designations of the mutations in SBEIIa of the D genome correspond to the position in the reference sequence SEQ ID NO: 5. Amino acid designations of the SBEIIa polypeptide of the A genome correspond to the amino acid position of reference sequence SEQ ID NO: 6. Nucleic acid designations of the mutations in SBEIIb of the A genome correspond to the position in the reference sequence SEQ ID NO: 7. Amino acid designations of the SBEIIb polypeptide of the A genome correspond to the amino acid position of reference sequence SEQ ID NO: 8. Nucleic acid designations of the mutations in SBEIIb of the B genome correspond to the position in the reference sequence SEQ ID NO: 9. Amino acid designations of the SBEIIb polypeptide of the B genome correspond to the amino acid position of reference sequence SEQ ID NO: 10. Nucleic acid designations of the mutations in SBEIIb of the D genome correspond to the position in the reference sequence SEQ ID NO: 11. Amino acid designations of the SBEIIb polypeptide of the A genome correspond to the amino acid position of reference sequence SEQ ID NO: 12.

TABLE 8

Examples of wheat plants identified which had a mutation in SBEIIa that was predicted to be severe and the crosses that were made to plants with severe SBEIIa mutations in a different genome.

| Cross | Variety | Gene | Nucleotide Mutation | A.A. Mutation |
|---|---|---|---|---|
| 1 | Express | SBEIIaA | G5267A | W436* |
|   | Express | SBEIIaB | G5038A | W436* |
|   | Express | SBEIIaD | G6305A | W432* |
| 2 | Express | SBEIIaA | G5267A | W436* |
|   | Express | SBEIIaB | G5069A | W446* |
|   | Express | SBEIIaD | G6335A | W442* |
| 3 | Express | SBEIIaA | G5267A | W436* |
|   | Express | SBEIIaB | G5193A | W458* |
|   | Express | SBEIIaD | G6305A | W432* |
| 4 | Kronos | SBEIIaA | G5267A | W436* |
|   | Kronos | SBEIIaB | G5073A | Splice Junction |

TABLE 8-continued

Examples of wheat plants identified which had a mutation in SBEIIa that was predicted to be severe and the crosses that were made to plants with severe SBEIIa mutations in a different genome.

| Cross | Variety | Gene | Nucleotide Mutation | A.A. Mutation |
|---|---|---|---|---|
| 5 | Kronos | SBEIIaA | G5267A | W436* |
|   | Kronos | SBEIIaB | G5219A | G467E |
| 6 | Kronos | SBEIIaA | G5267A | W436* |
|   | Kronos | SBEIIaB | G5033A | W434* |

Additionally, Express wheat plants identified as containing mutations in SBEIIa were rescreened for mutations in SBEIIb of the same genome using homoeologue specific primers. Plants with mutations in both SBEIIa and SBEIIb of each genome were sequenced and the plants containing severe mutations in both linked genes of the same genome were grown up and self-pollinated to obtain homozygous lines and confirm linkage of the mutations in SBEIIa and SBEIIb. Plants with mutations in both SBEIIa and SBEIIb in the same genome were crossed to plants with linked SBEII mutations in other genomes to obtain wheat lines with linked mutations in all three genomes.

TABLE 9: Examples of twelve Express wheat plants identified which had severe mutations in both SBEIIa and SBEIIb of the same genome (i.e., linked mutations) are shown in Table 9. The SBEIIa and SBEIIb genes are located close together on the chromosome and mutation segregation studies showed that these mutations were linked and were not inherited independently. It would be obvious to one skilled in the art that an alternative approach to identify linked mutations in both genes would be to first identify plants with mutations in their SBEIIb genomes and then rescreen these individuals for mutations in their SBEIIa genomes. It would also be obvious to one skilled in the art that an alternative approach to obtain linked mutations in both genes would be to identify plants in which recombination has occurred between mutations in SBEIIa and SBEIIb.

TABLE 9

Wheat plants with mutations in both SBEIIa and SBEIIb of the same genome

| Plant | Gene | Nucleotide Mutation | A.A. Mutation | Gene | Nucleotide Mutation | A.A. Mutation |
|---|---|---|---|---|---|---|
| 1 | SBEIIaA | C5804T | P519S | SBEIIbA | C2617T | P336L |
| 2 | SBEIIaA | G5463A | G472E | SBEIIbA | G2282A | W285* |
| 3 | SBEIIaA | G5463A | G472E | SBEIIbA | G2282A | W285* |
| 4 | SBEIIaA | G5463A | G472E | SBEIIbA | G2282A | W285* |
| 5 | SBEIIaA | G2605A | G264D | SBEIIbA | G1356A | E216K |
| 6 | SBEIIaA | C5757T | A503V | SBEIIbA | G278A | W59* |
| 7 | SBEIIaD | G6306A | D433N | SBEIIbD | C4573T | R325W |
| 8 | SBEIIaD | G5156A | G374E | SBEIIbD | C4246T | P275L |
| 9 | SBEIIaD | G5156A | G374E | SBEIIbD | C4246T | P275L |
| 10 | SBEIIaD | C3743T | S266F | SBEIIbD | G4290A | V290M |
| 11 | SBEIIaB | G5219A | G467E | SBEIIbB | C3232T | R325W |
| 12 | SBEIIaB | G2386A | G233D | SBEIIbB | C2786T | P263L |

Plants that were homozygous for severe linked mutations (SBEIIa and SBEIIb) in each genome were crossed with plants containing severe linked mutations in other genomes to create plants that had linked SBEIIa and SBEIIb mutations in all three genomes. Multiple combinations of mutations within genomes were produced during the crossing.

TABLE 10

Examples of wheat plants identified that had a severe mutation in SBEIIa and SBEIIb of each genome and crosses to achieve plants with mutations in both SBEIIa and SBEIIb of all three genomes.

| Cross | Gene | Nucleotide Mutation | A.A. Mutation | Gene | Nucleotide Mutation | A.A. Mutation |
|---|---|---|---|---|---|---|
| 1 | SBEIIaA | G2605A | G264D | SBEIIbA | G1356A | E216K |
|   | SBEIIaB | G2386A | G233D | SBEIIbB | C2786T | P263L |
|   | SBEIIaD | G6306A | D433N | SBEIIbD | C4573T | R325W |
| 2 | SBEIIaA | G2605A | G264D | SBEIIbA | G1356A | E216K |
|   | SBEIIaB | G2386A | G233D | SBEIIbB | C2786T | P263L |
|   | SBEIIaD | G5156A | G374E | SBEIIbD | C4246T | P275L |
| 3 | SBEIIaA | G2605A | G264D | SBEIIbA | G1356A | E216K |
|   | SBEIIaB | G2386A | G233D | SBEIIbB | C2786T | P263L |
|   | SBEIIaD | C3743T | S266F | SBEIIbD | G4290A | V290M |
| 4 | SBEIIaA | C5804T | P519S | SBEIIbA | C2617T | P336L |
|   | SBEIIaB | G2386A | G233D | SBEIIbB | C2786T | P263L |
|   | SBEIIaD | G6306A | D433N | SBEIIbD | C4573T | R325W |
| 5 | SBEIIaA | C5804T | P519S | SBEIIbA | C2617T | P336L |
|   | SBEIIaB | G2386A | G233D | SBEIIbB | C2786T | P263L |
|   | SBEIIaD | G5156A | G374E | SBEIIbD | C4246T | P275L |
| 6 | SBEIIaA | C5804T | P519S | SBEIIbA | C2617T | P336L |
|   | SBEIIaB | G2386A | G233D | SBEIIbB | C2786T | P263L |
|   | SBEIIaD | C3743T | S266F | SBEIIbD | G4290A | V290M |
| 7 | SBEIIaA | G5463A | G472E | SBEIIbA | G2282A | W285* |
|   | SBEIIaB | G2386A | G233D | SBEIIbB | C2786T | P263L |
|   | SBEIIaD | G6306A | D433N | SBEIIbD | C4573T | R325W |
| 8 | SBEIIaA | G5463A | G472E | SBEIIbA | G2282A | W285* |
|   | SBEIIaB | G2386A | G233D | SBEIIbB | C2786T | P263L |
|   | SBEIIaD | G5156A | G374E | SBEIIbD | C4246T | P275L |
| 9 | SBEIIaA | G5463A | G472E | SBEIIbA | G2282A | W285* |
|   | SBEIIaB | G2386A | G233D | SBEIIbB | C2786T | P263L |
|   | SBEIIaD | C3743T | S266F | SBEIIbD | G4290A | V290M |
| 10 | SBEIIaA | C5757T | A503V | SBEIIbA | G278A | W59* |
|   | SBEIIaB | G2386A | G233D | SBEIIbB | C2786T | P263L |
|   | SBEIIaD | G6306A | D433N | SBEIIbD | C4573T | R325W |
| 11 | SBEIIaA | C5757T | A503V | SBEIIbA | G278A | W59* |
|   | SBEIIaB | G2386A | G233D | SBEIIbB | C2786T | P263L |
|   | SBEIIaD | G5156A | G374E | SBEIIbD | C4246T | P275L |
| 12 | SBEIIaA | C5757T | A503V | SBEIIbA | G278A | W59* |
|   | SBEIIaB | G2386A | G233D | SBEIIbB | C2786T | P263L |
|   | SBEIIaD | C3743T | S266F | SBEIIbD | G4290A | V290M |
| 13 | SBEIIaA | G2605A | G264D | SBEIIbA | G1356A | E216K |
|   | SBEIIaB | G5219A | G467E | SBEIIbB | C3232T | R325W |
|   | SBEIIaD | G6306A | D433N | SBEIIbD | C4573T | R325W |
| 14 | SBEIIaA | G2605A | G264D | SBEIIbA | G1356A | E216K |
|   | SBEIIaB | G5219A | G374E | SBEIIbB | C3232T | R325W |
|   | SBEIIaD | G5156A | G467E | SBEIIbD | C4246T | P275L |
| 15 | SBEIIaA | G2605A | G264D | SBEIIbA | G1356A | E216K |
|   | SBEIIaB | G5219A | G467E | SBEIIbB | C3232T | R325W |
|   | SBEIIaD | C3743T | S266F | SBEIIbD | G4290A | V290M |
| 16 | SBEIIaA | C5804T | P519S | SBEIIbA | C2617T | P336L |
|   | SBEIIaB | G5219A | G467E | SBEIIbB | C3232T | R325W |
|   | SBEIIaD | G6306A | D433N | SBEIIbD | C4573T | R325W |
| 17 | SBEIIaA | C5804T | P519S | SBEIIbA | C2617T | P336L |
|   | SBEIIaB | G5219A | G467E | SBEIIbB | C3232T | R325W |
|   | SBEIIaD | G5156A | G374E | SBEIIbD | C4246T | P275L |
| 18 | SBEIIaA | C5804T | P519S | SBEIIbA | C2617T | P336L |
|   | SBEIIaB | G5219A | G467E | SBEIIbB | C3232T | R325W |
|   | SBEIIaD | C3743T | S266F | SBEIIbD | G4290A | V290M |
| 19 | SBEIIaA | G5463A | G472E | SBEIIbA | G2282A | W285* |
|   | SBEIIaB | G5219A | G467E | SBEIIbB | C3232T | R325W |
|   | SBEIIaD | G6306A | D433N | SBEIIbD | C4573T | R325W |
| 20 | SBEIIaA | G5463A | G472E | SBEIIbA | G2282A | W285* |
|   | SBEIIaB | G5219A | G467E | SBEIIbB | C3232T | R325W |
|   | SBEIIaD | G5156A | G374E | SBEIIbD | C4246T | P275L |
| 21 | SBEIIaA | G5463A | G472E | SBEIIbA | G2282A | W285* |
|   | SBEIIaB | G5219A | G467E | SBEIIbB | C3232T | R325W |
|   | SBEIIaD | C3743T | S266F | SBEIIbD | G4290A | V290M |
| 22 | SBEIIaA | C5757T | A503 V | SBEIIbA | G278A | W59* |
|   | SBEIIaB | G5219A | G467E | SBEIIbB | C3232T | R325W |
|   | SBEIIaD | G6306A | D433N | SBEIIbD | C4573T | R325W |
| 23 | SBEIIaA | C5757T | A503V | SBEIIbA | G278A | W59* |
|   | SBEIIaB | G5219A | G467E | SBEIIbB | C3232T | R325W |
|   | SBEIIaD | G5156A | G374E | SBEIIbD | C4246T | P275L |

TABLE 10-continued

Examples of wheat plants identified that had a severe mutation in SBEIIa and SBEIIb of each genome and crosses to achieve plants with mutations in both SBEIIa and SBEIIb of all three genomes.

| Cross | Gene | Nucleotide Mutation | A.A. Mutation | Gene | Nucleotide Mutation | A.A. Mutation |
|---|---|---|---|---|---|---|
| 24 | SBEIIaA | C5757T | A503V | SBEIIbA | G278A | W59* |
|  | SBEIIaB | G5219A | G467E | SBEIIbB | C3232T | R325W |
|  | SBEIIaD | C3743T | S266F | SBEIIbD | G4290A | V290M |

TABLE 11

Three examples of wheat plants with other combinations of mutations of SBEIIa and SBEIIb of multiple genomes.

| Type | Gene | Nucleotide Mutation | A.A. Mutation | Gene | Nucleotide Mutation | A.A. Mutation |
|---|---|---|---|---|---|---|
| SBEIIa Only | SBEIIaA | G5267A | W436* | SBEIIbB | C2786T | P263L |
| LinkedSBEIIa & IIb | SBEIIaB | G2386A | G233D | SBEIIbD | C4573T | R325W |
| LinkedSBEIIa & IIb | SBEIIaD | G6306A | D433N |  |  |  |
| LinkedSBEIIa & IIb | SBEIIaA | G2605A | G264D | SBEIIbA | G1668A | E216K |
| SBEIIa Only | SBEIIaB | G5038A | W436* |  |  |  |
| LinkedSBEIIa & IIb | SBEIIaD | G6306A | D433N | SBEIIbD | C4573T | R325W |
| LinkedSBEIIa & IIb | SBEIIaA | G2605A | G264D | SBEIIbA | G1668A | E216K |
| LinkedSBEIIa & IIb | SBEIIaB | G2386A | G233D | SBEIIbB | C2786T | P263L |
| SBEIIa Only | SBEIIaD | G6305A | W432* |  |  |  |

TABLE 12

Additional examples of wheat plants with other combinations of mutations of SBEIIa and SBEIIb of multiple genomes.

| Combo | Type | Gene | Nucleotide Mutation | A.A. Mutation | Gene | Nucleotide Mutation | A.A. Mutation |
|---|---|---|---|---|---|---|---|
| 1 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | G3599A | W233* |
| 2 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | G3599A | W233* |
| 3 | LinkedSBEIIa & IIb | SBEIIaA | G5267A | W436* | SBEIIbA | G2282A | W285* |
|  | SBEIIa Only | SBEIIaB | G5038A | W436* | SBEIIbB |  |  |
|  | LinkedSBEIIa & IIb | SBEIIaD | G6305A | W432* | SBEIIbD | G3599A | W233* |
| 4 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | G1916A | S208N |
|  | SBEIIa Only | SBEIIaD | G6305A | W432* | SBEIIbD |  |  |
| 5 | SBEIIa Only | SBEIIaA | G5267A | W436* | SBEIIbA |  |  |
|  | SBEIIa Only | SBEIIaB | G5038A | W436* | SBEIIbB |  |  |
|  | LinkedSBEIIa & IIb | SBEIIaD | G6305A | W432* | SBEIIbD | G3599A | W233* |
| 6 | LinkedSBEIIa & IIb | SBEIIaA | G5267A | W436* | SBEIIbA | G2282A | W285* |
|  | SBEIIa Only | SBEIIaB | G5038A | W436* | SBEIIbB |  |  |
|  | SBEIIa Only | SBEIIaD | G6305A | W432* | SBEIIbD |  |  |
| 7 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | SBEIIa Only | SBEIIaD | G6305A | W432* | SBEIIbD |  |  |
| 8 | LinkedSBEIIa & IIb | SBEIIaA | G5267A | W436* | SBEIIbA | G2156A | Splice Junction |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | C4573T | R325W |
| 9 | SBEIIa Only | SBEIIaA | G5267A | W436* | SBEIIbA |  |  |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | C4573T | R325W |
| 10 | LinkedSBEIIa & IIb | SBEIIaA | G5267A | W436* | SBEIIbA | G2156A | Splice Junction |
|  | SBEIIa Only | SBEIIaB | G5038A | W436* | SBEIIbB |  |  |
|  | LinkedSBEIIa & IIb | SBEIIaD | G6305A | W432* | SBEIIbD | C4573T | R325W |
| 11 | LinkedSBEIIa & IIb | SBEIIaA | G5267A | W436* | SBEIIbA | G2156A | Splice Junction |
|  | LinkedSBEIIa & IIb | SBEIIaB | G5038A | W436* | SBEIIbB | C3232T | R325W |
|  | SBEIIa Only | SBEIIaD | G6305A | W432* | SBEIIbD |  |  |
| 12 | SBEIIa Only | SBEIIaA | G5267A | W436* | SBEIIbA |  |  |
|  | SBEIIa Only | SBEIIaB | G5038A | W436* | SBEIIbB |  |  |
|  | LinkedSBEIIa & IIb | SBEIIaD | G6305A | W432* | SBEIIbD | C4573T | R325W |
| 13 | LinkedSBEIIa & IIb | SBEIIaA | G5267A | W436* | SBEIIbA | G2156A | Splice Junction |

TABLE 12-continued

Additional examples of wheat plants with other combinations of mutations of SBEIIa and SBEIIb of multiple genomes.

| Combo | Type | Gene | Nucleotide Mutation | A.A. Mutation | Gene | Nucleotide Mutation | A.A. Mutation |
|---|---|---|---|---|---|---|---|
|  | SBEIIa Only | SBEIIaB | G5038A | W436* | SBEIIbB |  |  |
|  | SBEIIa Only | SBEIIaD | G6305A | W432* | SBEIIbD |  |  |
| 14 | SBEIIa Only | SBEIIaA | G5267A | W436* | SBEIIbA |  |  |
|  | LinkedSBEIIa & IIb | SBEIIaB | G5038A | W436* | SBEIIbB | C3232T | R325W |
|  | SBEIIa Only | SBEIIaD | G6305A | W432* | SBEIIbD |  |  |
| 15 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | C4573T | R325W |
| 16 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | G3599A | W233* |
| 17 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | C4573T | R325W |
| 18 | SBEIIa Only | SBEIIaA | G5267A | W436* | SBEIIbA |  |  |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | G3599A | W233* |
| 19 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | G3599A | W233* |
| 20 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | C4573T | R325W |
| 21 | LinkedSBEIIa & IIb | SBEIIaA | G5267A | W436* | SBEIIbA | G2282A | W285* |
|  | SBEIIa Only | SBEIIaB | G5038A | W436* | SBEIIbB |  | — |
|  | LinkedSBEIIa & IIb | SBEIIaD | G6305A | W432* | SBEIIbD | C4573T | R325W |
| 22 | LinkedSBEIIa & IIb | SBEIIaA | G5267A | W436* | SBEIIbA | G2156A | Splice Junction |
|  | SBEIIa Only | SBEIIaB | G5038A | W436* | SBEIIbB |  |  |
|  | LinkedSBEIIa & IIb | SBEIIaD | G6305A | W432* | SBEIIbD | G3599A | W233* |
| 23 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | C3232T | R325W |
|  | SBEIIa Only | SBEIIaD | G6305A | W432* | SBEIIbD |  |  |
| 24 | LinkedSBEIIa & IIb | SBEIIaA | G5267A | W436* | SBEIIbA | G2156A | Splice Junction |
|  | LinkedSBEIIa & IIb | SBEIIaB | G5038A | W436* | SBEIIbB | G1916A | S208N |
|  | SBEIIa Only | SBEIIaD | G6305A | W432* | SBEIIbD |  |  |

Mutations in SBEIIa increase amylose content and resistant starch levels in wheat seeds from (1) double homozygous Kronos wheat plants with a stop mutation in SBEIIaA (G5267A /W436*) and a splice junction mutation in SBEIIaB (G5073A/splice junction), and (2) double homozygous Kronos wheat plants with a stop mutation in SBEIIaA (G5267A/W436*) and a missense mutation in SBEIIaB (G5219A/G467E) were evaluated for amylose content using the K-AMYL kit from Megazyme (Ireland) and controls of known amylose amounts. The amylose content of whole seed milled starch was an average of 40-49% for the double homozygous mutant seeds compared to seeds from their wild type sibling controls whose amylose content was 20-25%.

Seeds from (1) triple homozygous Express wheat plants with a stop mutation in SBEIIaA (G5267A/W436*), SBEIIaB (G5038A/W436*), and SBEIIaD (G6305A/W432*), and (2) triple homozygous Express wheat plants with a stop mutation in SBEIIaA (G5267A/W436*), SBEIIaB (G5069A/W446*), and SBEIIaD (G6335A/W442*) were evaluated for amylose content using the K-AMYL kit from Megazyme (Ireland) and a controls of known amylose amounts. The amylose content of whole seed milled starch was 50-60% for the triple homozygous mutant seeds compared to seeds from their wild type sibling controls whose amylose content was 20-25%.

Flour milled from the triple homozygous mutant seed had 12-15% resistant starch content compared to flour from the wild type sibling controls, which had approximately 1% resistant starch. Bread made from the triple homozygous mutant flour had increased resistant starch levels of 6% compared to bread made from flour of wild type sibling and parental controls, which had less than 1% resistant starch. Bread made from a 50:50 blend with standard wheat flour had increased resistant starch levels of 4% compared to bread made from a 50:50 blend with sibling control flour that had resistant starch levels less than 1%.

Seeds from (1) quadruple homozygous Express wheat plants with a linked mutation in SBEIIaA (G5463A/ G472E)- and SBEIIbA (G2282A/W285*), combined with a stop mutation in SBEIIaB (G5038A/W436*), and SBEIIaD (G6305A/W432) was evaluated for amylose content using the K-AMYL kit from Megazyme (Ireland) and controls of known amylose amounts. The amylose content of whole seed milled starch was 58% for the quadruple homozygous mutant seeds compared to seeds from their wild type sibling controls whose amylose content was 20-25%.

Seeds from (2) quadruple homozygous Express wheat plants with a stop mutation in SBEIIaA (G5267A/W436*), combined with a stop mutation in SBEIIaB (G5038A/ W436*), and a linked mutation in SBEIIaD (G6306A/ D433N)- and SBEIIbD (C4573T/R325W) was evaluated for amylose content using the K-AMYL kit from Megazyme (Ireland) and controls of known amylose amounts. The amylose content of whole seed milled starch was 38% for the quadruple homozygous mutant seeds compared to seeds from their wild type sibling controls whose amylose content was 23%.

Seeds from (3) quadruple homozygous Express wheat plants with a stop mutation in SBEIIaA (G5267A/W436*), combined with a linked mutation in SBEIIaB (G5219A/G467E)- and SBEIIbB (C3232T/R325W), and a stop mutation in SBEIIaD (G6305A/W432*) were evaluated for amylose content using the K-AMYL kit from Megazyme (Ireland) and controls of known amylose amounts. The amylose content of whole seed milled starch was 38% for the quadruple homozygous mutant seeds compared to seeds from their wild type sibling controls whose amylose content was 24%.

Seeds from a sextuple homozygous Express wheat plants with linked mutations in SBEIIaA (G5463A/G472E) and SBEIIbA (G2282A/W285*), combined with linked mutations in SBEIIaB (G5219A/G467E) and SBEIIbB (C3232T/R325W), and linked mutations in SBEIIaD (G6306A/D433N) and SBEIIbD (C4573T/R325W) were evaluated for amylose content using the K-AMYL kit from Megazyme (Ireland) and controls of known amylose amounts. The amylose content of whole seed milled starch was 25-30% for the sextuple homozygous mutant seeds compared to seeds from their wild type sibling controls whose amylose content was 16%.

The above examples are provided to illustrate the invention but not limit its scope. Other variants of the invention will be readily apparent to one of ordinary skill in the art and are encompassed by the appended claims and all their equivalents. The examples above used TILLING technology to create and identify mutations in one or more SBEII genes of wheat that increase amylose levels in wheat seeds, but one of ordinary skill in the art would understand that other methods such as targeted mutagenesis (also known as site-directed mutagenesis, site-specific mutagenesis or oligonucleotide-directed mutagenesis) could be used to create the useful mutations of the present invention in one or more SBEII loci of wheat (see for example Zhang et al., *PNAS* 107(26):12028-12033, 2010; Saika et al., *Plant Physiology* 156:1269-1277, 2011). All publications, patents, and patent applications cited herein are hereby incorporated by reference.

What is claimed is:

1. *Triticum turgidum* ssp durum flour comprising one or more homozygous mutations in both SBEIIa alleles of each SBEIIa gene of the A and B genomes selected from:

(i) the one or more mutations in the SBEIIa gene of the A genome is W436* at a position corresponding to W436 of SEQ ID NO:2; and the one or more mutations in the SBEIIa gene of the B genome is a splice junction mutation at a position corresponding to G5073A of SEQ ID NO: 3; and (ii) the one or more mutations in the SBEIIa gene of the A genome is W436* at a position corresponding to W436 of SEQ ID NO:2; and the one or more mutations in the SBEIIa gene of the B genome is G467E at a position corresponding to G467 of SEQ ID NO:4;

wherein * indicates a stop codon.

2. Purified starch from the flour of claim 1.

3. A food comprising the flour of claim 1.

4. A beverage product comprising the flour of claim 1.

5. A method of making wheat grain, said method comprising:
- (a) obtaining a wheat plant of the species *Triticum turgidum* ssp durum comprising one or more homozygous mutations in both SBEIIa alleles of each SBEIIa gene of the A and B genomes, selected from:
  - (i) the one or more mutations in the SBEIIa gene of the A genome is W436* at a position corresponding to W436 of SEQ ID NO:2; and the one or more mutations in the SBEIIa gene of the B genome is a splice junction mutation at a position corresponding to G5073A of SEQ ID NO: 3; and
  - (ii) the one or more mutations in the SBEIIa gene of the A genome is W436* at a position corresponding to W436 of SEQ ID NO:2; and the one or more mutations in the SBEIIa gene of the B genome is G467E at a position corresponding to G467 of SEQ ID NO:4;
- wherein * indicates a stop codon;
- wherein the wheat plant produces wheat grain that germinates;
- wherein the wheat grain from the wheat plant has an increased amylose level as compared to wheat grain from a wild type wheat plant; and
- (b) harvesting wheat grain from the wheat plant.

6. Flour comprising the wheat grain made according to claim 5.

7. Purified starch made from the flour of claim 6.

8. A food comprising a component of the wheat grain made according to claim 5.

9. A beverage product comprising a component of the wheat grain made according to claim 5.

* * * * *